United States Patent [19]

Liburdy

[11] Patent Number: 5,190,761
[45] Date of Patent: Mar. 2, 1993

[54] ELECTROMAGNETIC FIELD TRIGGERED DRUG AND CHEMICAL DELIVERY VIA LIPOSOMES

[76] Inventor: Robert P. Liburdy, 1820 Mountain View Rd., Tiburon, Calif. 94920

[21] Appl. No.: 537,191

[22] Filed: Jun. 12, 1990

Related U.S. Application Data

[63] Continuation-in-part of Ser. No. 367,013, Jun. 16, 1989, abandoned, which is a continuation-in-part of Ser. No. 302,803, Jan. 27, 1989, abandoned, which is a continuation-in-part of Ser. No. 893,436, Aug. 5, 1986, Pat. No. 4,801,459.

[51] Int. Cl.$^5$ .................... A61K 9/127; A61K 9/133
[52] U.S. Cl. ................. 424/450; 128/804; 264/4.3; 424/1.1; 428/402.2; 436/829; 514/866
[58] Field of Search ............ 264/4.3; 428/402.2; 424/1.1, 450; 436/829; 128/804

[56] References Cited

U.S. PATENT DOCUMENTS

| | | |
|---|---|---|
| 4,235,871 | 11/1980 | Papahadjopoulos et al. ..... 424/92 X |
| 4,483,929 | 11/1984 | Szoka ................. 436/829 X |
| 4,565,696 | 1/1986 | Heath et al. ............ 424/450 |
| 4,668,638 | 5/1987 | Janoff et al. ............ 264/4.6 X |
| 4,670,386 | 6/1987 | Sugaar .................. 435/29 |
| 4,762,915 | 8/1988 | Kung et al. ............ 424/450 X |
| 4,801,459 | 1/1989 | Liburdy ............... 424/450 |

OTHER PUBLICATIONS

Liburdy, Robert P. et al., "Microwaves and the Cell Membrane II. Temperature, Plasma and Oxygen Mediate Microwave-Induced Membrane Permeability in the Erythrocyte," *Radiation Research*, 102, 190-205 (1985).
Yatvin et al., *Science* (1978) 202:1290-1293.
Weinstein et al., *Science* (1979) 204:188-191.
Liburdy et al., *Radiation Research* (1985) 103:266-275.
Ladbrooke et al., *Biochem Biophys. Acta* (1968) 150:333-340.
Blok et al., *Biochem. Biophys. Acta* (1977) 464:509-518.
Nishimura et al., *Radiation Research* (1990) 122:161-167.
Wang et al., *Proc. Natl. Acad. Sci.* (1987) 84:7851-7855.
Wang et al., *Biochemistry* (1989) 28:9508-9514.
Gregoriadis, Ed., "Liposome Technology," vol. III, CRC Press, Inc., Boca Raton, Fla. (1985) pp. 137-175.
Hahn, "Hyperthermia and Cancer" Plenum Press, New York, NY (1982) pp. 191-202.
Saalman et al., *Biochim. Biophys. Acta* (1991) 1064:124-130.

Primary Examiner—Richard D. Lovering
Attorney, Agent, or Firm—Morrison & Foerster

[57] ABSTRACT

The present invention relates to a system and to a method of delivering a drug to a preselected target body site of a patient, comprising the steps of encapsulating the chemical agent within liposomes, essentially temperature insensitive, i.e. not having a specific predetermined phase transition temperature within the specific temperature range of drug administration; administering the liposomes to the target body site; and subjecting the target body site to nonionizing electromagnetic fields in an area of the preselected target body in order to release said chemical agent from the liposomes at a temperature of between about +10 and 65° C. The invention further relates to the use of said liposomes to bind to the surface of or to enter target tissue or an organ in a living system, and, when subjected to a nonionizing field, to release a drug from the liposomes into the target site.

25 Claims, 34 Drawing Sheets

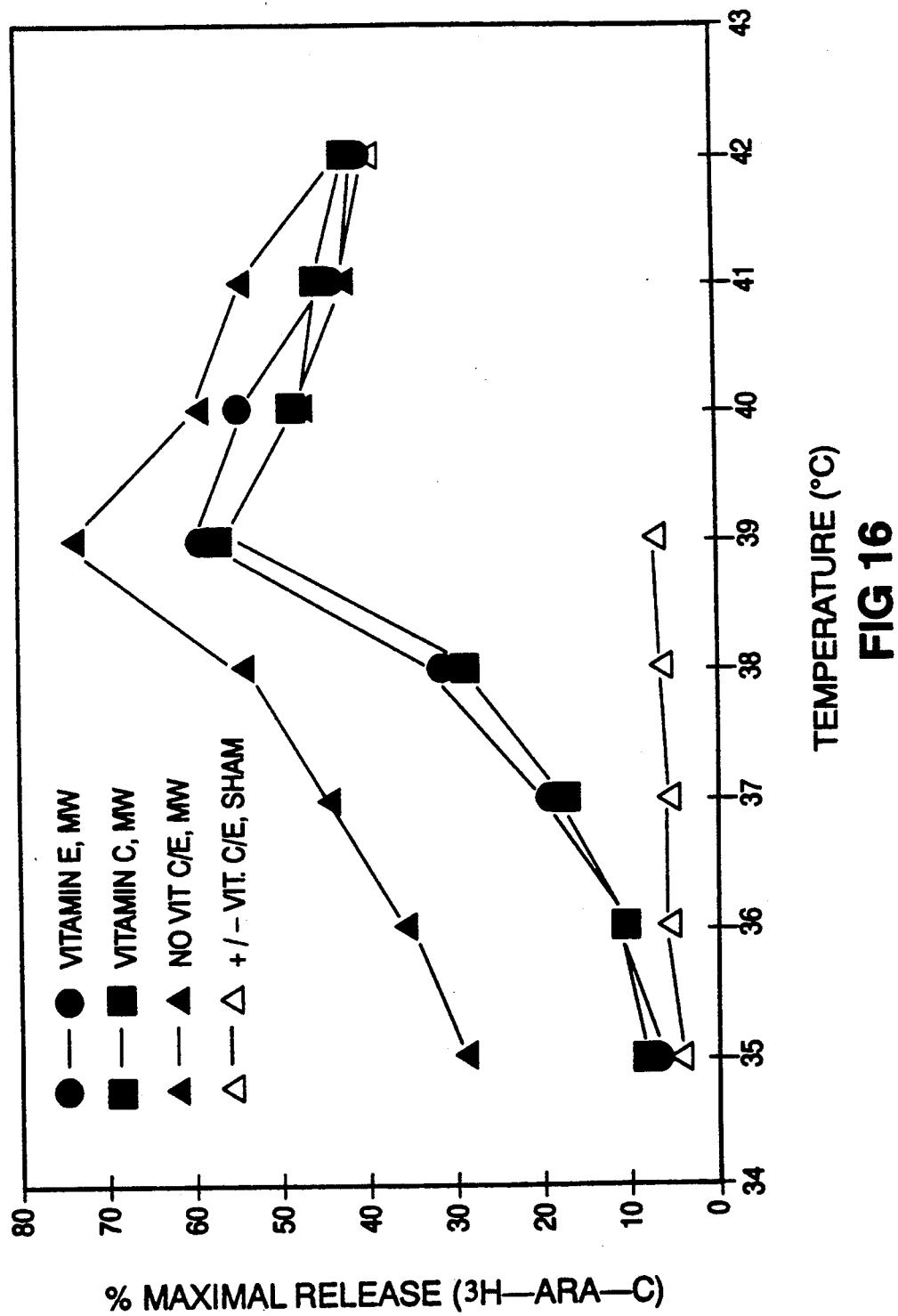

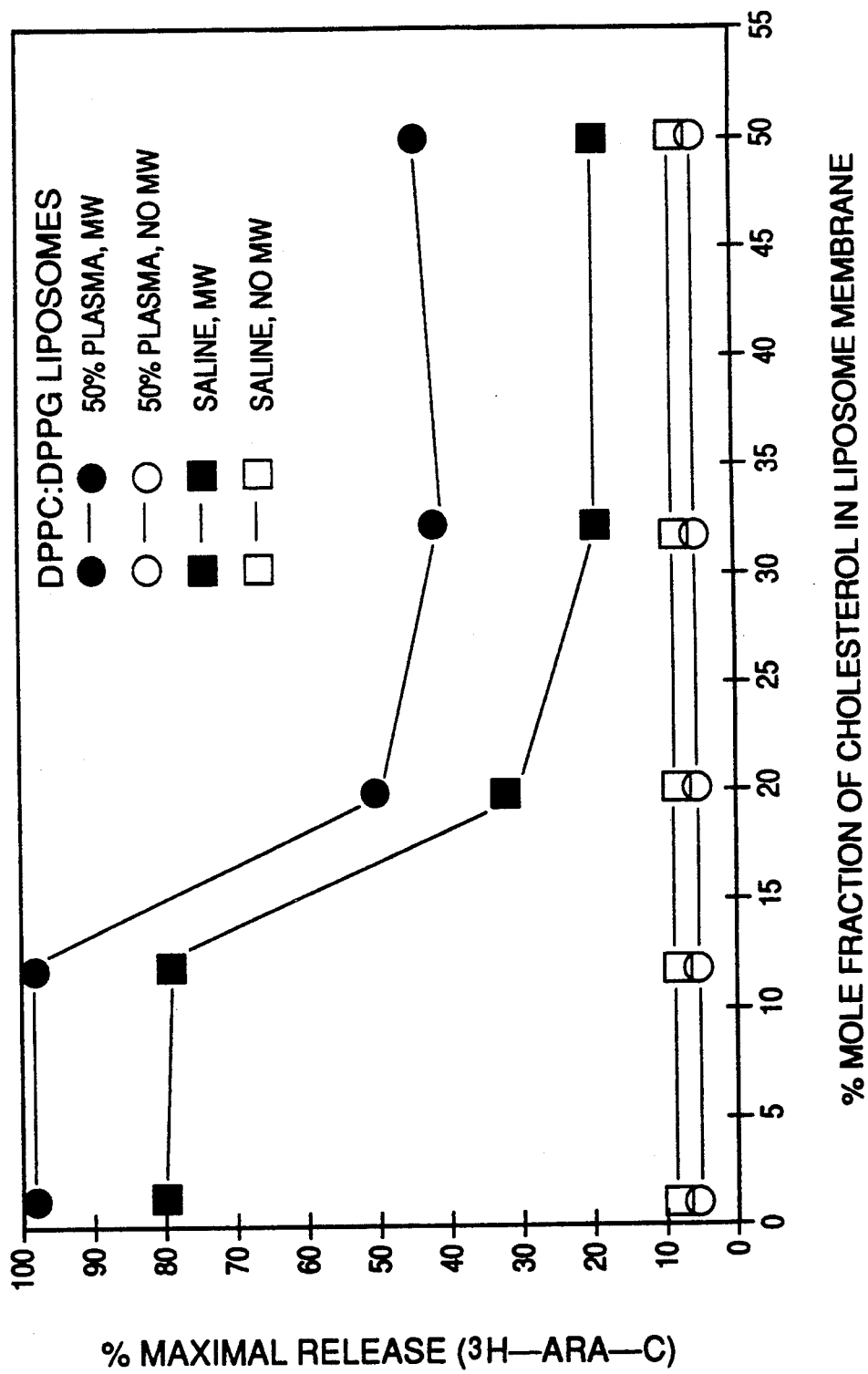

5,190,761

ELECTROMAGNETIC FIELD TRIGGERED DRUG AND CHEMICAL DELIVERY VIA LIPOSOMES

STATEMENT OF GOVERNMENT INTEREST

The government has rights to this invention pursuant to Contract No. DE-AC03-76SF00098 awarded by the U.S. Department of Energy.

BACKGROUND OF INVENTION

The present application is a continuation-in-part of U.S. patent application Ser. No. 367,013, filed Jun. 16, 1989, now abandoned which is a continuation-in-part of U.S. patent application Ser. No. 302,803, filed Jan. 27, 1989, now abandoned which is a continuation-in-part of U.S. patent application Ser. No. 893,436, filed Aug. 5, 1986, now U.S. Pat. No. 4,801,459. These applications and this issued patent are incorporated herein by reference.

This application also incorporates by reference in its entirety, the text and drawings of U.S. patent application Ser. No. 366,931, filed Jun. 16, 1989 and now abandoned.

FIELD OF INVENTION

This invention relates generally to a technique for delivering drugs and other pharmaceutically beneficial chemicals to a patient. More particularly it concerns effecting such delivery by using non-ionizing electromagnetic fields (static magnetic fields, extremely low frequency, microwave and RF electromagnetic fields) to release the drugs or chemicals from liposomes. More specifically, the present invention relates to a technique using liposomes to deliver drugs and/or chemicals to specific target cells or groups of cells such that the drug or chemical is released into the target cell or cells using a nonionizing electromagnetic field. The liposome vesicle can be employed at a temperature, T, far from its phase transition temperature, Tc, where it is naturally leaky, so that the liposome membrane is either in the fluid ($T>Tc$) or the solid ($T<Tc$) phase. This means that the liposome is stable and will not normally be permeable until exposure to the nonionizing field of choice.

RELATED DISCLOSURES

It is well recognized in the medical field that the most effective procedure in treating localized disease is to direct the pharmaceutical or drug agent (collectively "drugs") to the affected area thus avoiding undesirable toxic effects of systemic treatment. Some techniques used today to deliver drugs within the body involve the utilization of time-release capsules or gel matrices from which drugs slowly "leak", or the use of implantable "syringes" that mechanically release drugs into muscles or into the blood stream. Another, and perhaps more effective delivery system, encompasses the use of liposomes containing the appropriate drug or chemical. The liposome with encapsulated drug is directed to the specific area of interest and the drug released. This last step is the most problematic.

Liposomes are microscopic particles which are made up of one or more lipid bilayers enclosing an internal aqueous compartment. They are normally not leaky but can become leaky if a hole or pore occurs in the membrane, if the membrane is dissolved or degrades, or if the membrane temperature is increased to the phase transition temperature, Tc. As pointed out in *Science*, 202: 1290 (1978), the major barrier to the use of liposomes as drug carriers is making the liposomes release the drugs on demand at target sites. In both the above identified article and in *Science*, 204: 188 (1979), the specific use of applied heat to raise the liposome temperature to Tc to make them leaky or permeable is described.

General references of interest regarding liposomes include, for example, *Liposome Technology, Volumes I, II, and III* (G. Gregoriadis, Ed.) CRC Press, Inc., Boca Raton, Fla. (1985), and *Radiation Research*, 103: 266 (1985).

*Biochem Biophys Acta*, 150: 333 (1968), discloses the use of cholesterol to produce a solid phase liposome. *Biochem Biophys Acta*, 164: 509 (1977) discloses the effect of cholesterol incorporation on the temperature dependence of water permeation through liposome membranes prepared from phosphatidylcholine.

*Radiation Research*, 122: 161 (1990), and references therein, disclose the use of heat from a waterbath to release drugs from liposomes that possess a phase transition temperature, Tc.

None of the references cited herein individually or collectively teach or suggest the present invention. Nevertheless, all of the references cited herein are incorporated by reference in their entirety.

The currently available methods for targeted drug delivery as described above in particular in *Science*, 204: 188 (1979) and *Science*, 202: 1290 (1978) still fall short as an effective drug release methodology since the prolonged application of heat can, in itself, create problems within the human body, and, in many instances, drug release triggered from liposomes by applying significant heat can damage body tissues. In such circumstances the adverse effects of the treatment outweigh the beneficial effects of using the liposome as a drug delivery vehicle.

Therefore, it would be advantageous to have available an effective system in which drugs could be released from liposomes without the need for concomitant heating.

Current methods of drug delivery via liposomes require that the liposome carrier will ultimately become permeable and release the encapsulated drug. This can be accomplished in a passive manner in which the liposome bilayer membrane degrades over time through the action of agents in the body. Every liposome composition will have a characteristic half-life in the circulation or at other sites in the body. In contrast to passive drug release, active drug release involves using an agent to induce a permeability change in the liposome vesicle. Liposome membranes can be constructed that become destabilized when the environment becomes acidic near the liposome membrane (*Proc. Natl. Acad. Sci. USA*, 84: 7851 (1987); *Biochemistry*, 28: 9508 (1989) and references therein). For example, when liposomes are endocytosed by a target cell they can be routed to acidic endosomes which will destabilize the liposome and result in drug release. Alternatively, the liposome membrane can be chemically modified such that an enzyme is placed as a coating on the membrane which slowly destabilizes the liposome (*The FASEB Journal*, 4: 2544 (1990)). Since control of drug release depends on the amount of enzyme initially placed in the membrane, which defines the time course of liposome destabilization, there is no way to modulate or alter drug release to achieve pulsatile "on demand" drug delivery. The same problem exists for pH-sensitive liposomes in that as soon as the liposome vesicle comes into contact with a target cell they will be engulfed and a drop in pH will lead to drug release.

A third method to achieve active drug delivery is to employ a liposome having a predetermined phase transition temperature, Tc, above body temperature (see for example, *Radiation Research*, 112: 161 (1990) and references therein). This means that body temperature will maintain the liposomes below Tc so they will not become leaky when placed in the body. This mechanism for drug release is capable of "on demand" drug delivery since these liposomes experience a greatly increased membrane permeability at Tc and this enables drug or chemical release. To release drugs from such phase transition liposomes placed in the body requires the application of heat until Tc is achieved. Such liposomes, however, must be made of highly purified and expensive phase transition temperature phospholipid materials (either as a single component or multicomponent mixtures).

Thus, it would be desirable to have available a liposome system which would allow the use of cheaper lipid materials but still retain the ability to actively release drugs when triggered by some physical agent.

An additional aspect of current medical treatment of disease is the known affect of hyperthermia itself on tumor processes. As pointed out in "Hyperthermia and Cancer," by G. M. Hahn, Plenum Press, N.Y. 1982, the application of heat to elevate tumor temperatures to 42° C. renders tumor tissue inactive while leaving normal tissue relatively intact. In addition, the application of heat in the presence of drugs can lead to thermal enhancement of drug action. Thus, it would be advantageous to deliver drugs to a tumor site in a nonthermal manner, and then have the option of applying heat for hyperthermia treatment. This could be accomplished by first releasing drugs from liposome vesicles using a physical agent at nonthermal levels and subsequently using various heating modalities to achieve therapeutic levels of hyperthermia.

Within the scope of the present invention the permeability of both solid and fluid liposomes is greatly increased by non-thermal interaction with non-ionizing electromagnetic radiation at temperatures other than Tc. Thus, the present invention offers an extremely convenient, fast, effective and reasonably economical medical tool for rapid delivery of drugs and/or chemicals into localized areas such as tissues, cells or organs of the human body by utilizing drug encapsulated in liposomes made of inexpensive materials and effecting the drug release from these liposomes by applying to the preselected treatment area an electromagnetic field of intensity sufficient to effect the release of the drug from liposomes but without the need to resort to heating liposomes.

SUMMARY OF THE INVENTION

One aspect of the present invention relates to a system utilizing nonionizing electromagnetic fields to trigger the localized release of drugs from drug-containing liposomes.

Another aspect of this invention concerns drug release which occurs when liposomes with encapsulated drugs are placed in a static magnetic (0.01–7.5 Tesla) or electromagnetic field ranging between 26–2450 MHz in order to release the drugs from the liposomes. Drug release may be enhanced by oxygen, plasma, or plasma factors and is attenuated by antioxidants.

Another aspect of the present invention relates to a method using noninvasive electromagnetic fields such as microwaves to trigger the release of solute from liposomes by way of the electromagnetic fields destabilization of the bilayers resulting in coupling of dipolar groups in the bilayer with the oscillating electric or electromagnetic field.

In another aspect, the present invention relates to a method of delivering a drug to a preselected target body site, comprising the steps of:

(a) encapsulating the drug within a liposome composition, wherein the liposome composition is such that is does not display a phase transition temperature, Tc, over the range of temperatures it would experience in the body. This means that the liposome does not have a specific predetermined phase transition temperature Tc at which the liposome composition is capable of releasing the drug within this temperature range;

(b) administering the liposome composition to or into the target body site or into the circulation to enable distribution of the liposomes to target body sites; and (c) subjecting the target body site and liposome composition to nonionizing electromagnetic fields at a target site and releasing the drug from the liposomes over a temperature range of between about +10° and 65° C.

Another aspect of the present invention is to subject the preselected area for treatment to one or multiple treatments (pulses) of electromagnetic fields for periods of time as short as one nanosecond and at power levels of up to approximately 60 mW/gm.

Another aspect of this invention is the enhancement of release of drugs from drug-containing liposomes at target sites by injecting plasma, plasma factors, or by introducing oxygen into the target site.

Yet another aspect of this invention is that a liposome vesicle can be loaded with multiple drugs or chemicals to enable the delivery of a series of drugs simultaneously. In addition, liposomes could be loaded with different compounds so that when released they interact at the target site of treatment to form an active drug species, or can be activated by the application of a physical agent such as an electromagnetic field.

BRIEF DESCRIPTION OF THE DRAWINGS

FIG. 17 shows the effect of membrane cholesterol as a perturbing agent on microwave-triggered drug release from DPPC:DPPG liposomes.

DETAILED DESCRIPTION OF THE INVENTION AND PREFERRED EMBODIMENTS

Definitions

Figure 2:
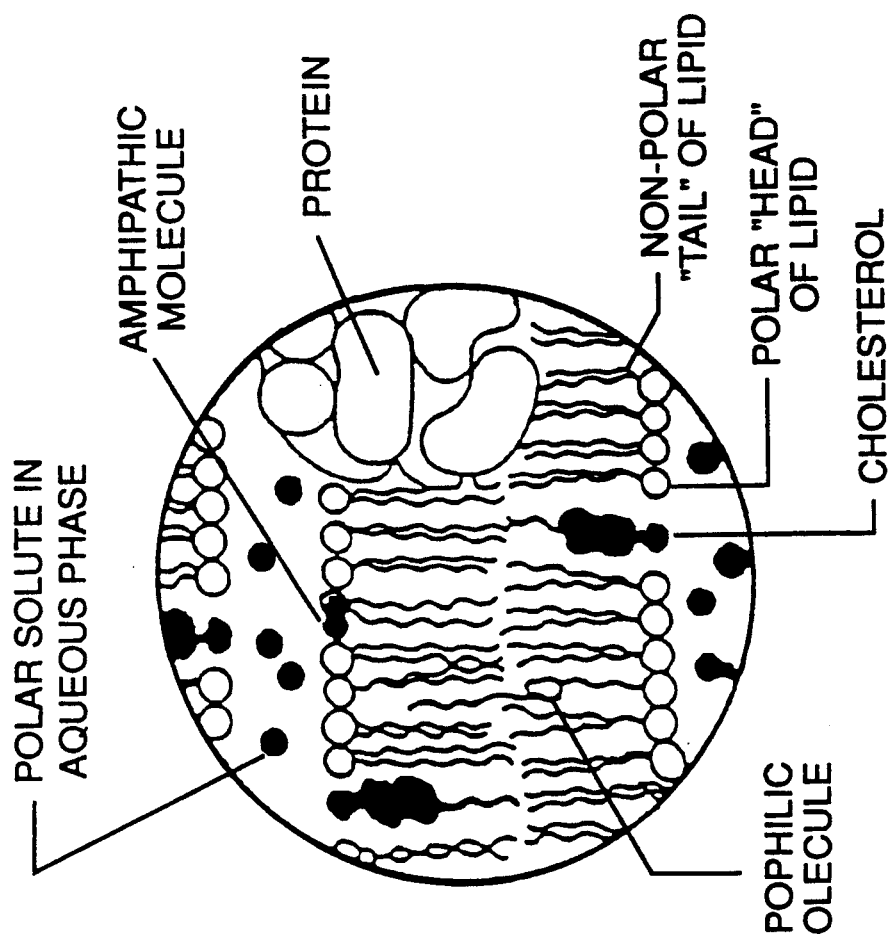
FIG. 2 is a cross-sectional representation of a portion of a single liposome bilayer membrane. It shows a number of membrane perturbing agents such as protein, mixtures of different phospholipids, or cholesterol, which, when present in sufficient concentrations, can disrupt the bilayer and obliterate the ability of the membrane to undergo a phase transition at any temperature.

As used herein:

"Nonionizing radiation" and "Electromagnetic Fields" refer to electromagnetic fields in the frequency range of 26-2450 MHz and to static magnetic fields that cover the range 0.01-7.5 Tesla.

"DMPC" refers to dimyristoylphosphatidylcholine, a 14 carbon chain phospholipid that is neutral in charge.

"DMPG" refers to dimyristoylphosphatidylglycerol, a 14 carbon phospholipid that is negative in charge.

"DPPC" refers to dipalmitoylphosphatidylcholine, a 16 carbon chain phospholipid that is neutral in charge.

"DPPG" refers to dipalmitoylphosphatidylglycerol, a 16 carbon chain phospholipid that is negative in charge.

"EPC" refers to egg phosphatidylcholine, or lecithin.

"HPI" refers to hydrogenated phosphatidylinositol.

"HPC" refers to hydrogenated phospahtidylcholine.

aT refers to alpha-Tocopherol (Vitamin E) which is an antioxidant agent that can be placed into the liposome membrane. When present, antioxidants act to reduce microwave-triggered liposomal drug release, as shown herein.

Ab refers to an antibody molecule.

"Drug" refers to an agent which has a desirable pharmacological action when administered to a patient. This term covers natural and synthetic materials.

"Liposome" refers to an approximately spherically-shaped bilayer structure comprised of a natural or synthetic phospholipid membrane or membranes, and sometimes other membrane components such as cholesterol and protein, which can act as a physical reservoir for drugs. These drugs may be sequestered in the liposome membrane or may be encapsulated in the aqueous interior of the vesicle. Liposomes are characterized according to size and to number of membrane bilayers vesicle diameter can be large (>200 nm) or small (<50 nm) and the bilayer can have a unilammellar, oligolammellar, or multilammellar membrane.

"Phase transition temperature (Tc)" refers to the temperature at which a liposome membrane, comprised of phospholipid compounds, has both phase states, i.e., fluid (liquid) and solid (gel), present simultaneously. The fluid (liquid) state is characterized by free rotational motion within the membrane of the hydrocarbon chains of the phospholipids, whereas the solid (gel) state is associated with restricted hydrocarbon tail motion. At Tc both phase states coexist and the liposome membrane becomes naturally permeable or leaky; this results in the spontaneous release of encapsulated drug or chemical agent from the liposome membrane or from the interior space of the liposome. At temperatures below Tc the bilayer is referred to as being in the solid or gel state, and at temperatures above Tc the bilayer is in a liquid or fluid state; these states are not normally leaky. To have a phase transition in the liposome bilayer generally requires the exclusive presence of highly purified phospholipids of identical fatty acid chain length and polar head group composition. Mixing phospholipid species or adding perturbing agents at appropriate concentrations will obliterate the ability of the bilayer to undergo a phase transition.

"Perturbing agent" refers to a natural or synthetic compound or a combination of compounds which when added to a liposome membrane obstructs the formation of a phase transition. The amount of perturbing agent necessary to obstruct the formation of a phase transition varies according to the steric nature of the compound. Usually, but not always, 20–40 percent mole fraction of the agent is required. Typically a perturbing agent is selected from natural or synthetic compounds: cholesterol; phospholipids, e.g., egg phosphatidylcholine, egg phosphatidylglycerol; inorganic metal compounds and complexes; and proteins such as antibodies. Perturbing agents also include various compositions of phosphatidylcholine or phosphatidylglycerol, or phosphatidylethanolamine wherein these structures are further substituted by aliphatic organic acids having different carbon chain lengths, e.g. palmitoyl (16 carbons) and lauryl (12 carbons).

"Nonphase transition Liposome" refers to a liposome that does not display a phase transition temperature Tc within a specified temperature range of interest. For example, if a liposome "A" has a phase transition temperature Tc of 4° C., and the specified temperature range is from 10° C.–50° C., then, over this temperature range, it is referred to as a nonphase transition liposome. In addition, since this particular temperature range is above the nominal Tc, liposome "A" will be in the fluid (liquid) phase state at all temperatures between 10° C.–50° C.

"Targeted Liposomal Drug Delivery" refers to the homing and accumulation of liposomes that carry drugs at specified patient body target sites of interest. This results in liposomes binding to a target cell surface, and, depending on the cell type, the liposome will remain on the cell surface or be internalized by phagocytotic cells. The conventional method for achieving targeting of liposomes is to modify the liposome membrane by attaching an antibody that will bind to a specified cell surface marker on the target cell. Introduction of the antibody-modified liposome into the circulation will then result in binding of the modified liposome to the target cell, provided the circulation will bring the liposome into close physical proximity to the target site.

"Microinjection of Liposomal Drug" refers to the technique of using liposomes that are bound to a target cell surface, or that have been internalized by the target cell, to directly introduce drug into the target cell. This technique is also referred to as "using liposomes as a cellular-level microsyringe". Microinjection of drugs from liposomes bound to the target cell surface can involve nonionizing fields triggering fusion of the liposome membrane with the target cell membrane, and this results in delivery of drugs into the target cells, as described herein.

"Sham exposure" refers to isothermal, control experiments in which liposomes of interest are placed in an unenergized exposure device and then treated with oxygen, nitrogen, plasma, or other combinations under comparable exposure conditions at various temperatures. For microwave and RF field exposures different temperatures are usually obtained by adjusting the temperature of the dielectric fluid circulating around the sample cell. In this way, a direct comparison is made between a sample which is treated with an electromagnetic field and one which is not.

The present invention concerns a preparation of drugs encapsulated in liposomes and release of drugs from liposomes affected by nonionizing electromagnetic fields. The permeability of liposome membrane depends on many factors which include their lipid composition, type of drug, drug compartmentalization into the bilayer membrane or into the aqueous interior compartment, site of release and other complex physiochemical properties. It is generally recognized that undisturbed liposomes are not very leaky or permeable, but can be made so by disturbing membrane properties.

Thus, this invention concerns a novel method of effecting the permeability of the liposome membrane by subjecting certain nonphase transition temperature liposomes to magnetic or electromagnetic fields. By applying such fields, a new type of interaction occurs that makes the liposomes permeable and/or leaky and allows drug to be released at the site to which electromagnetic fields are directed.

A wide variety of liposomes are capable of being used within the scope of the present invention. The only restriction is that they do not possess a phase transition temperature, Tc, within the temperature range of interest. This means, by the definition given above, that these liposomes are referred to as nonphase transition liposomes, and that they will be in either the fluid (liquid) or solid (gel) phase state within the specified temperature range. Drug delivery using electromagnetic fields using liposomes at temperatures corresponding to Tc has been previously addressed in my U.S. Pat. No. 4,801,459.

Lipid Components

The liposomes used in demonstrating the feasibility of the present invention are unilamellar vesicles (LUV) or multilayered multilamellar vesicles (MLV). The liposomes are formed from standard vesicle forming lipids, which generally include neutral and negatively charged phospholipids with or without a sterol, such as cholesterol. The selection of lipids is generally guided by considerations of (a) desired liposome size and ease of liposome sizing, and (b) lipid and water soluble drug release rates from the site of liposome injection.

Typically, the major phospholipid (PL) components in the liposomes are phosphatidylcholine (PC), phosphatidylglycerol (PG), phosphatidylserine (PS), phosphatidylinositol (PI) or egg yolk lecithin (EYL). PC, PG, PS, and PI having a variety of acyl chain groups or varying chain length and degree of saturation are commercially available, or may be isolated or synthesized by well known techniques. The degree of saturation can be important since hydrogenated PL (HPL) components have greater stiffness than do unhydrogenated PL components; this means that liposomes made with HPL components will be more rigid. In addition, less saturated PLs are more easily extruded, which can be a desirable property particularly when the liposomes must be sized below about 0.3 microns, for purposes of filter sterilization or other formulation requirement. Methods used in sizing and filter-sterilizing liposomes are discussed below.

Protective Agent

It is well known that the lipid components of liposomes promote peroxidative and free radical reactions which cause progressive degradation of the liposomes. This problem has been discussed at length in the above-mentioned U.S. Pat. No. 4,797,285. Briefly, the patent reports that lipid peroxidative and free radical damage effect both lipid and entrapped drug components in a liposome/drug composition. It is noted that the extent of free radical damage to lipid and drug components was reduced significantly when a lipophilic free radical quencher, such as alpha-tocopherol (a-T) was included in the vesicle-forming lipids. Interestingly, a significantly greater reduction in lipid damage and drug modification was observed when the liposome/drug composition was formulated in the presence of both a-T and a water soluble, iron-specific chelator, such as ferrioxamine. Since ferrioxamine can complex tightly to ferric iron at six coordination sites, it is likely that the compound acts by inhibiting iron-catalyzed peroxidation in the aqueous phase of the liposome suspension. The effectiveness of the two protective agents together suggests that both iron-catalyzed peroxidative reactions occurring in the aqueous phase, and free radical reactions being propagated in the lipid phase are important contributors to lipid peroxidative damage.

Lipophilic free radical scavengers can advantageously be used in the composition employed herein and include preferably a-T, or a pharmacologically acceptable analog or ester thereof, such as alpha-tocopherol succinate. Other suitable free radical scavengers include butylated hydroxytoluene (BHT), propyl gallate, and their pharmacologically acceptable salts and analogs. Additional lipophilic free radical quenchers which are acceptable for parenteral administration in humans, at an effective level in liposomes, may be used. The free radical quencher is typically included in the lipid components used in preparing the liposomes, according to conventional procedures. Preferred concentrations of the protective compound are between about 0.2 and 2 mole percent of the total lipid components making up the liposomes; however, higher levels of the protective compound, particularly a-T or its succinate analog, are compatible with liposome stability and are pharmacologically acceptable.

Methods of Liposome Formation

The liposome suspension of the invention can be prepared by any of the standard methods for preparing and sizing liposomes. These include hydration of lipid films, solvent injection, reverse-phase evaporation and other methods, such as those detailed in *Am. Rev. Biophys. Bioeng.*, 9: 467 (1980). Reverse-phase evaporation vesicles (REVs) prepared by the reverse-evaporation phase method is described in U.S. Pat. No. 4,235,871, incorporated herein by reference. The preparation of multilamellar vesicles (MLVs) by thin-film of a lipid film or by injection technique is described in U.S. Pat. No. 4,737,923, incorporated by reference. In two later procedures, which are generally preferred, a mixture of liposome forming lipids dissolved in a suitable solvent is evaporated in a vessel to form a thin film, which is covered by an aqueous buffer solution. The lipid film hydrates to form MLVs, typically with sizes between about 0.1 to 10 microns.

Either the REVs or MLVs preparations can be further treated to produce a suspension of smaller, relatively homogeneous-size liposomes, in a 0.1–1.0 micron size range. Advantages of smaller, more homogeneous-size liposomes are, for example the higher density of liposome packing at a mucosal tissue surface, the higher concentration of liposome encapsulated drug transported to the target organ or tissue, or the greater optical clarity when applied topically to the eye. One effective sizing method involves extruding an aqueous suspension of the liposomes through a polycarbonate membrane having a selected uniform pore size, typically 0.2, 0.4, 0.6, 0.8 or 1 microns as shown in *Ann. Rev. Biophys. Bioeng.*, 9: 467 (1980). The pore size of the membrane corresponds roughly to the largest sizes of liposomes produced by extrusion through that membrane, particularly where the preparation is extruded two or more times through the same membrane. A more recent method involves extrusion through an asymmetric ceramic filter. The method is detailed in U.S. Pat. No. 4,737,323, incorporated herein by reference.

Alternatively, the REVs or MLVs preparations can be treated to produce small unilamellar vesicles (SUVs), large unilamellar vesicles (LUVs) or oligolamellar vesicles (OLVs) which are characterized by sizes in the 0.04–0.08 μ, 0.1–0.5 μ, and mixed micron range, respectively. Because of the small particle sizes, SUVs suspensions can be optically quite clear, and thus advantageous and preferred for such applications as the delivery of steroid to the minuscule lung alveoli. Another advantage of SUVs, is the greater packing density of liposomes at a mucosal surface which can be achieved with smaller liposome particles, thus making SUVs preferred for inhalation, for treatment of deep lung diseases, degenerative interstitial pneumonia or in general for the intraveneous administration since the SUVs would get into the smallest peripheral veins and arteries.

One preferred method for producing SUVs is by homogenizing an MLVs preparation, using a conventional high pressure homogenizer of the type used commercially for milk homogenization. Here the MLVs preparation is cycled through the homogenizer, with periodic sampling of particle sizes to determine when the MLVs have been substantially converted to SUVs.

The larger liposome vesicles, whether MLVs or LUVs, however, do have other advantages such as, for example, a larger capacity for drug encapsulation and may therefore be preferred for certain routes of administration or delivery to specific targets.

The use of all SUVs, LUVs, MLVs, OLVs or mixture thereof is contemplated to be within the scope of this invention depending on intended therapeutical application and route of administration.

The drug is encapsulated in the liposomes by using for example the procedure described in U.S. Pat. No. 4,752,425, incorporated by reference.

One liposome vehicle employed within the technique of the present invention is preferably made up of 4:1 weight combination of dipalmitoylphosphatidylcholine (DPPC), optionally radiolabeled (14C-DPPC), and dipalmitoylphosphatidylglycerol (DPPG), and is prepared in a physiological buffer made up of saline with around 10 mM HEPES, at pH 7.4.

These vesicles can preferably be made by reverse phase evaporation using chloroform and isopropyl ether. However, the vesicles prepared in this or any other suitable manner, and for reasons which become more apparent later, may optionally contain two radioisotope markers: cytosine arabinofuranoside (3H-ARA-C) of MW 234 daltons as an encapsulated label to follow permeability changes in the membrane and the release of 3H-ARA-C simulating the release of drugs, and 14-C-DPPC as a membrane label to follow changes in liposome membrane permeability and fragmentation.

Liposome Sizing and Sterilization

Following liposome preparation, the liposomes may be sized to achieve a desired size range and relatively narrow distribution of liposome sizes. One preferred size range is about 0.2-0.4 microns, which allows the liposome suspension to be sterilized by filtration through a conventional depth filter, typically a 0.2 micron filter. The filter sterilization method can be carried out on a high through-put basis only if the liposomes have first been sized down to the about 0.2-0.4 micron range. The importance of sterilization for any pharmaceutical product is well understood and it will be appreciated that by using this filtration sizing step the sterilization will be also achieved at the same time and without additional steps.

Several techniques are available for sizing liposomes of a desired size. Sonicating a liposome suspension either by bath or probe sonication produces a progressive size reduction down to small unilamellar vesicles (SUVs) less than about 0.5 microns in size. Homogenization is another method which relies on shearing energy to fragment large liposomes into smaller ones. In a typical homogenization procedure, MLVs are recirculated through a standard emulsion homogenizer until selected liposome sizes, typically between about 0.1 and 0.5 microns, are observed. In both methods, the particle size distribution can be monitored by conventional laser beam particle size discrimination.

Extrusion of liposomes through a small-pore polycarbonate membrane or an asymmetric ceramic membrane is an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size.

Removing Free Drug

Even under the most efficient encapsulation methods, the initial sized liposome suspension may contain up to 50% or more drug in free (non-encapsulated) form. The drug can be encapsulated such that it is sequestered in the liposome bilayer (lipophilic compounds) or trapped in the liposome internal aqueous phase (hydrophilic compounds). The presence of such free drug may in some cases be tolerated but in many other cases is undesirable because these drugs are often toxic in their free form and for that reason are being encapsulated in liposomes. Therefore, in order to maximize the advantages of liposomal drug and to minimize the effect of the free drug, it may be important to remove free drug from the final injectable suspension.

Several methods are available for removing non-entrapped compound from a liposome suspension. In one method, the liposomes in the suspension are pelleted by high-speed centrifugation, leaving free compound and very small liposomes in the supernatant. This approach is followed where several liposome washings are employed. Another method involves concentrating the suspension by ultrafiltration, then resuspending the concentrated liposomes in a drug-free replacement medium. Alternatively, gel filtration can be used to separate liposome particles from solute molecules.

Following treatment to remove free drug, the liposome suspension is brought to a desired concentration for administration. Typically, the liposomes are administered by i.v., i.m., or s.c. injection. Thus, the preparation of the final dosage for treatment may involve resuspending the liposomes in a suitable volume of injection medium, such as saline, buffer, and such other pharmaceutically acceptable injectable medium as may be appropriate for the drug suspension or route of administration. The resuspension is particularly appropriate where the liposomes have been concentrated, for example by centrifugation or ultra-filtration, or concentrating the suspension volume. The suspension is then sterilized by filtration as described above. These media and other representative injectable components are well known and set forth in *Reminqton's Pharmaceutical Sciences*, 17th Ed., Mack Publishing, Easton, PA. 1985.

Liposomes Without a Phase Transition: Nonphase Transition Liposomes

Using the methods of liposome formation, as described above, liposomes without a phase transition over a specified temperature range can be prepared when a suitable perturbing agent is added to the phospholipid membrane, or when a multicomponent phospholipid liposome is constructed. Thus, for example, the perturbing agent cholesterol can be added to the membrane of a liposome displaying a Tc over a specified temperature range of interest. Such a membrane is comprised of, for example, a single highly purified phospholipid. At sufficient concentrations, cholesterol converts this material essentially into a nonphase transition liposome. The obliteration of a phase transition will render liposome membranes impermeant and highly stable with regard to leakage of drug. In the method here described using electromagnetic fields as a triggering agent for liposome drug release, one observes a significant increase in drug release from such nonphase transition liposomes during treatment with electromagnetic fields.

The use of nonphase transition liposomes as drug delivery vehicles has several advantages. First, these liposomes are extremely stable with respect to temperature since they do not exhibit a phase transition temperature, Tc, at which they become permeable and leaky. Importantly, they can also be prepared with very inexpensive materials since the use of highly purified phospholipids is not required. Using liposomes as drug delivery vehicles, via this method, has additional advantages. Liposomes of this type can be prepared to include a broad range of drugs which may be, via this method, usefully administered and/or released to specific cells, organs, or tissue, either intermittently or a over a sustained period of time. Nonphase transition liposomes allow the administration of relatively high drug doses of relatively toxic drugs with reduced side effects that are usually associated with free drug at such high concentrations. Liposomes may be administered to persons as a liposome depot at a tissue site or may be administered directly into the circulation. Circulating liposomes will not release the drug unless subjected to an electromagnetic field. In turn, electromagnetic fields may be selectively directed only to target areas where the drug release is desired. All other liposomes outside of the target area will not release the drug; liposomes in the general circulation and liposomes at a distant liposome depot outside of the exposure site will remain intact. The process of drug release using electromagnetic fields may be repeated intermittently until all drug is released from the liposome population.

Application and Use of Nonionizing Fields to Trigger Liposomal Drug Release

The present invention is typically used in the following manner. A suspension of liposomes with encapsulated drug is prepared in sterile pharmaceutical form suitable for i.v., i.m., s.c., or any other route of injection administration. The suspension is then administered to the patient in need of drug treatment and the liposomes are subsequently treated with a safe but effective dose of electromagnetic field. "Safe" in this context means that it does not heat the tissue to hyperthermic (43° C.) or supra-hyperthermic (>43° C.) temperature levels that may cause tissue damage. As discussed above, if hyperthermia treatment is to be used in conjunction with drug delivery, electromagnetic fields of relatively high intensity may be used to elevate tissue temperature subsequent to the use of lower intensities to trigger drug release from liposomes.

The liposomes may be injected to form one or more localized depots or may be injected to circulate freely in the blood stream with the potential to be targeted to specific tissue sites and localize at a site of interest. The latter case is termed targeted drug delivery and the bound liposomes are treated with the electromagnetic field to trigger localized drug release at the target site.

The nonionizing field acts to trigger drug delivery in two ways: (1) by destabilizing the liposome bilayer so that membrane fusion between the liposome and the target cellular structure occurs, thus facilitating the direct delivery of drug into the target cell; and (2) by triggering the release of drug in high concentrations from liposomes at the surface of the target cell so that the drugs are driven across the cell membrane by a concentration gradient. In either case the direct, cellular-level, microinjection of drug into the target cell is achieved.

The electromagnetic field source is placed near or on the patient's skin surface as close to the liposome depot or to the site for drug administration as is practical. For example, if freely circulating liposomes are used instead of a localized liposome depot the nonionizing field would be focused on a tissue area of interest that has blood circulation so that liposomes in this area are treated and release drug as they circulate through the local field. The subject can be treated with the field for a single treatment period or be treated at different time periods (i.e. multiple doses) using a number of intermittent bursts of the field.

The specific process of targeted drug delivery using liposomes via this method has several unique advantages. The targeting phase involves liposomes binding to a target cell and this will result in an extraordinarily high concentration of encapsulated drug at the surface of the target cell. A typical target cell has a diameter of approximately 7 microns (7,000 nanometers). This size is large compared to that of a liposome vesicle having a typical diameter of 100 nanometers. Approximately 450 million liposome vesicles can be bound to the surface of such a target cell, and each liposome vesicle can be loaded with drug at a high concentration ($>100mM$). This situation represents the most effective means for bringing high concentrations of drug to the surface of a target cell. Using electromagnetic fields via the method we describe here the problem of releasing drug from these bound liposomes can be overcome.

DETAILED DESCRIPTION OF THE DRAWINGS

A detailed description of the major features of experimental procedures used with the present invention are set forth in *Radiation Research*, 103: 266 (1985), *Radiation Research*, 108: 102 (1986), and U.S. Pat. No. 4,801,459, which are incorporated herein by reference.

Liposome Structure, Permeability, and The Phase Transition

Figure 1:
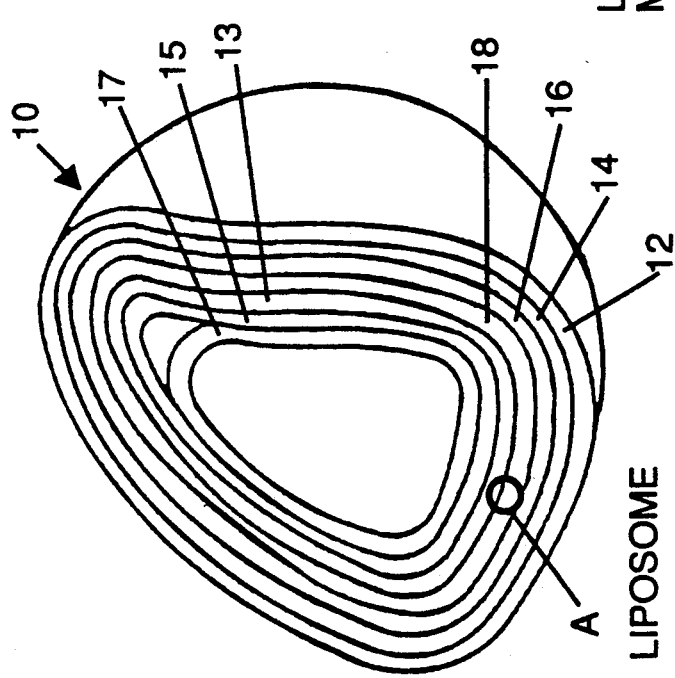
FIG. 1 is a pictorial representation of a typical liposome utilized with the drug delivery technique of the present invention.

FIG. 1 pictorially illustrates a cross-section through a typical multilammelar liposome 10 with phospholipid layers 12, 13, 14, 15, 16, 17, 18. A cross section taken at site A is illustrated in expanded scale in FIG. 2. Site A shows a typical arrangement of the lipids in a single bilayer of the liposome. Phospholipid (lipid) molecules form the bilayers and they have a polar head group and a non-polar hydrocarbon tail. The drug encapsulated in the liposome may be either attached to the bilayer as an amphipathic molecule shown here, or dissolved as a polar solute in aqueous phase. In addition, proteins may be present as perturbing agents.

As stated above, liposomes are normally not leaky unless the membrane is physically altered or the liposomes are maintained at their respective phase transition temperature, Tc, at which each liposome 10 undergoes a phase transition. At Tc the physical properties of the membrane change and allow the release of drugs trapped inside. Different components such as phospholipids, proteins and sterols such as cholesterol can be used to construct the liposome bilayer and to design liposome membrane permeability properties. Thus, depending on the liposome bilayer composition and hence on their membrane properties, liposomes either do or do not possess a Tc within a specified temperature range where spontaneous leakage can occur.

Figure 3:
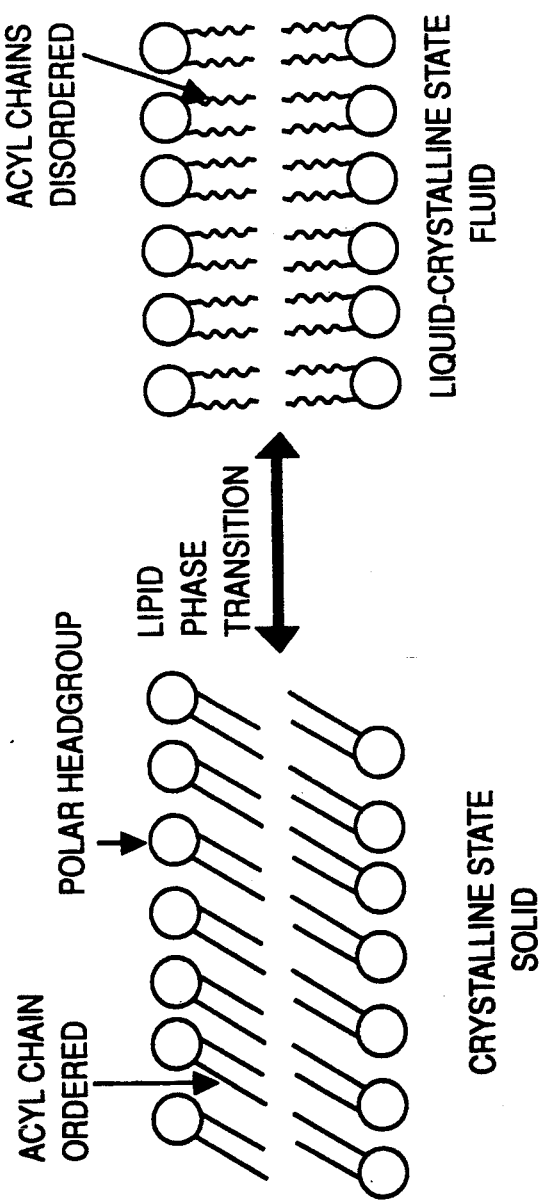
FIG. 3 is a diagrammatic representation of a liposome membrane in cross-section to illustrate the differences in membrane structure that correspond to the solid and the fluid phase state.
Figure 4:
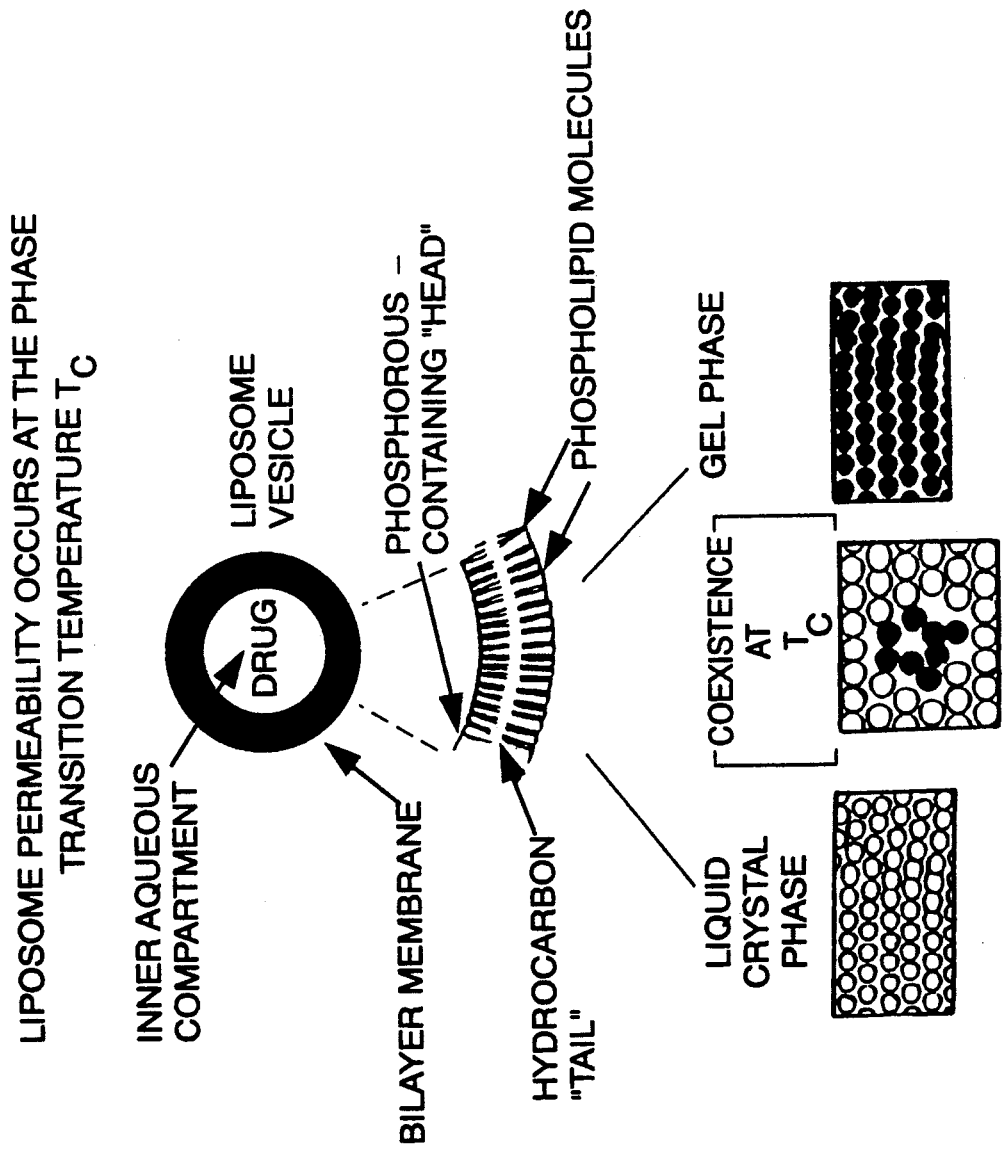
FIG. 4 depicts the formation of pores that occur in the liposome membrane at Tc, the phase transition temperature, when both phase states coexist. This leads to increased membrane permeability.

The phase transition from the solid(gel) to fluid(liquid) state is illustrated schematically in FIG. 3. The long phospholipid molecules that comprise the liposome bilayer have hydrocarbon acyl carbon chains that form the interior of the membrane structure. This internal space is hydrophobic and the hydrocarbon tails are capable of rotational motion such that at relatively low temperatures the carbon chains are restricted in motion. This corresponds to a solid or gel-like phase. At higher temperatures the relative motion of the hydrocarbon tails is increased and the bilayer has a fluid or liquid-like phase. FIG. 4 illustrates schematically the permeability increase that spontaneously occurs at Tc when both the fluid (liquid) and solid(gel) state coexist. At Tc when both phase states coexist there are pores or channels formed in the bilayer at the boundary interfaces and this leads to a marked increase in permeability of the liposome membrane.

Figure 5:
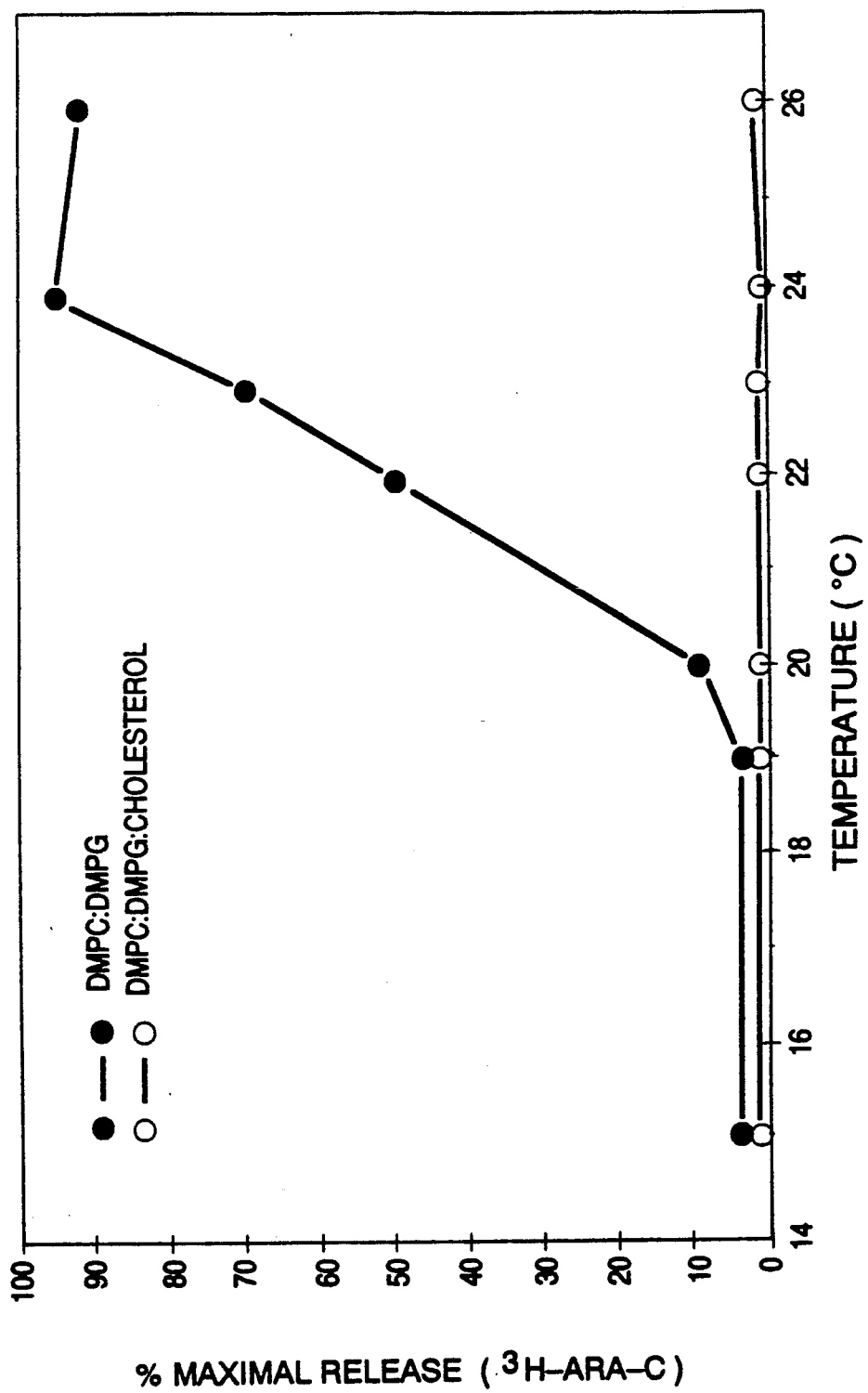
FIG. 5 is a graph which presents data illustrating the marked increase in permeability that occurs in a typical phase transition liposome DMPC:DMPG (Tc=23° C.). When cholesterol is incorporated as a perturbing agent into the liposome membrane Tc is eliminated and the liposome is no longer permeable.

FIG. 5 illustrates graphically the phenomena described in FIG. 4 using experimental data obtained using liposomes constructed from DMPC and DMPG phospholipids (DMPC:DMPG, 4:1), which possess a Tc of approximately 23° C. (phase transition liposomes), and using DMPC:DMPG liposomes that were modified by the addition of cholesterol to 40 mole percent to eliminate Tc (nonphase transition liposomes). These cholesterol-modified liposomes do not exhibit a phase transition because cholesterol is a perturbing agent that inhibits the cooperative interactions necessary for the gel-to-liquid transition of the membrane phospholipids. Both liposomes were loaded with 3H-ARA-C, a tritiated cancer drug, which acted as a marker for permeability. In these studies liposomes were suspended in a buffered saline solution (pH 7.4, 300 mOsm), aliquots were maintained at the temperatures shown in FIG. 5 for fifteen minutes, and then assayed for the release of isotope, as described below. As temperature treatment was increased from 15° to 31° C. the DMPC:DMPG liposomes displayed a marked increase in permeability at approximately 23° C., which coincides with the phase temperature Tc. In contrast, the same liposomes when modified with cholesterol showed no increase in permeability over this same temperature range. These data demonstrate that the addition of a perturbing agent such as cholesterol eliminates liposome permeability at Tc. It is, therefore, not possible to release any encapsulated drug from nonphase transition liposomes simply by submitting these liposomes to physiologically acceptable heat. For this type of liposome some other means of release induction is necessary. Nonionizing fields provide just such a means.

Quantitation of Drug and Chemical Release from Liposomes

Two primary release assays, which are in vitro and in vivo assay tests, were used to quantitate the electromagnetic field-triggered release of chemical and biochemical markers from liposomes.

In vitro assays for chemical marker release are based on detecting the release of isotopic markers, 3H-ARA-C and 14C-DPPC, or the release of fluorescence compounds such as 6-carboxyfluorescein (6-CF). The utilization of the 14C-labeled DPPC as an isotopic marker is extremely important in support of the present invention because the phospholipid DPPC, which forms part of the liposomal membrane, is only released into the supernatant when the liposome membrane is physically disrupted. No radiolabelled 14C-DPPC was detected in the supernatant following electromagnetic field treatment of liposomes. This finding verifies that drug release did not occur as a result of membrane breakage or fragmentation in which the release of drugs would be accompanied by the release of membrane fragments, i.e. with the presence of 14C-DPPC.

The in vitro release assay involved the treatment of liposomes with an electromagnetic field of between about 26 and 2650 MHz intensity from 0.1 to 60mW/gm in such a manner that the temperature never exceeded the specific limits of between about 10°-65° (preferably 15°-50° C.) at any given time. The electromagnetic field treatment was followed by rapid pelleting the liposomes at 170,000×g to enable collection of the supernatant. The collected supernatant was then analyzed for the presence of 3H-ARA-C or 14C-DPPC by conventional liquid scintillation spectroscopy, and for the presence of released fluorescent markers by fluorescence spectroscopy. Maximal drug marker release was determined by treating the liposomes with detergent, such as Triton X-100 ®, to solubilize the membrane. This detergent-induced release was defined as 100% maximal release and drug release values in experiments are expressed as a percentage of this maximal release.

Figure 6:
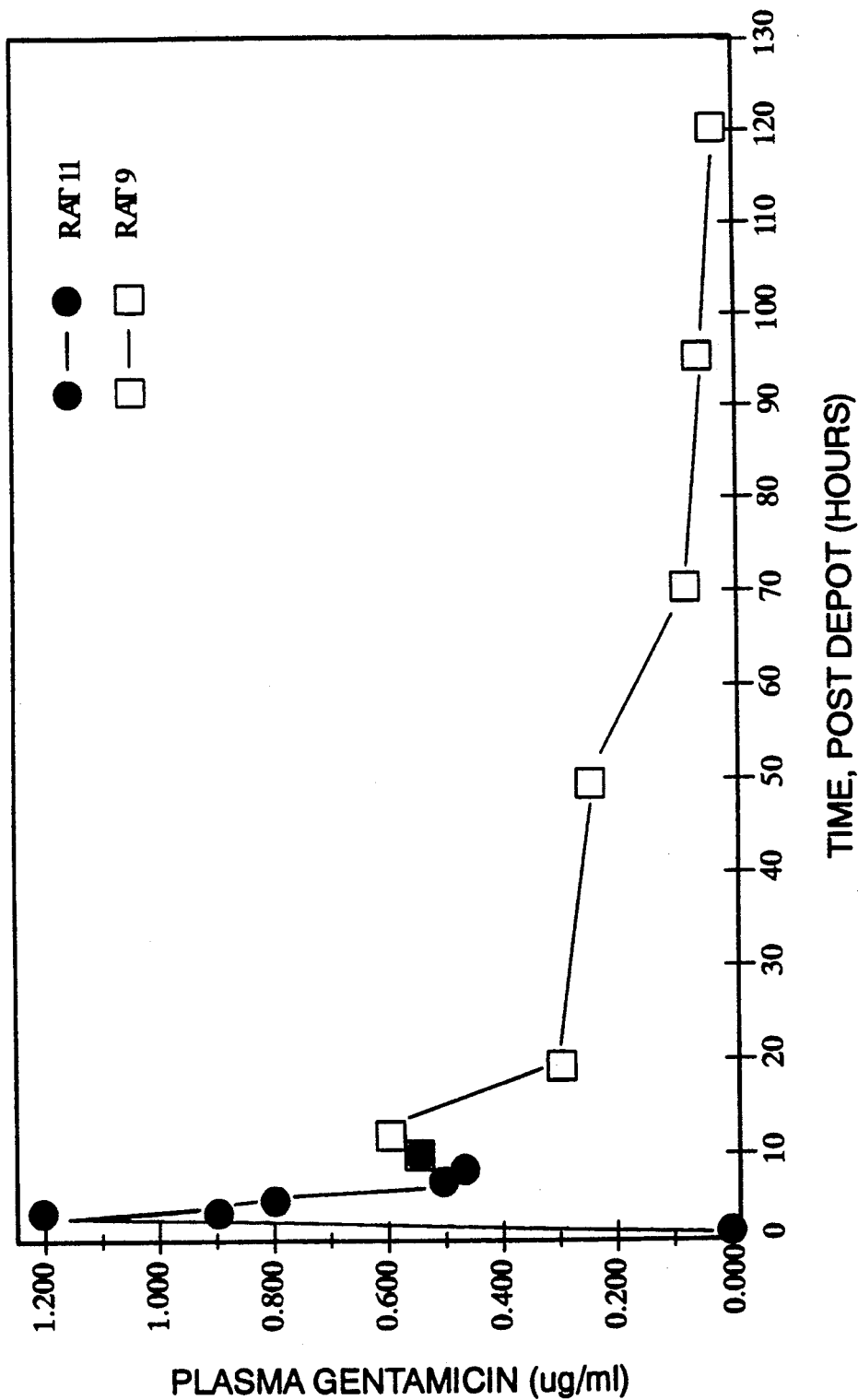
FIG. 6 is a graph illustrating spontaneous drug release from a subcutaneous liposome depot placed into a rat. Release of Gentamicin and subsequent appearance into the blood stream is depicted.

The in vivo release assay involved the administration of liposomal encapsulated drug to rats as a subcutaneous depot in the shoulder or leg one day prior to electromagnetic field treatment. This 24 hour period is critical for the clearance of any free drug that may be present in the initial depot. The elimination of free drug from a liposome depot is illustrated in FIG. 6. In this study Gentamicin-loaded liposomes were placed into the leg muscle of subject rats and the appearance of drug in the circulation was monitored. Immediately after placing the liposome depot in the animal free Gentamicin that was present in the liposome depot diffused into the circulation as indicated by the elevated levels of drug observed during the first two hours. Blood plasma concentrations, however, were reduced significantly until essentially all free Gentamicin was cleared from the depot by at least 24 hours.

On the day of the exposure treatment(s) the animals were catheterized via the femoral artery and blood samples drawn for RIA analysis of blood plasma drug, at predetermined time periods. The animals were maintained at 37° C. on a heating/cooling pad and animal core temperature was continually monitored along with respiration rate.

Exposure Devices For Treatment With Nonionizing Fields: In Vitro and In Vivo Studies The technique of this invention represents a new modality that employs nonionizing fields in a non-thermal manner to accomplish the rapid, localized and spatially selective delivery of drugs and/or chemicals in vivo from nonphase transition temperature liposomes.

Consequently, the present invention provides a technique whereby a variety of liposomes may release a variety of drugs rapidly in response to the application of nonionizing fields. In addition, this drug release may be greatly enhanced in the presence of plasma and when oxygen is present. The enhancement can be as much as 100% of maximal release.

Figure 7:
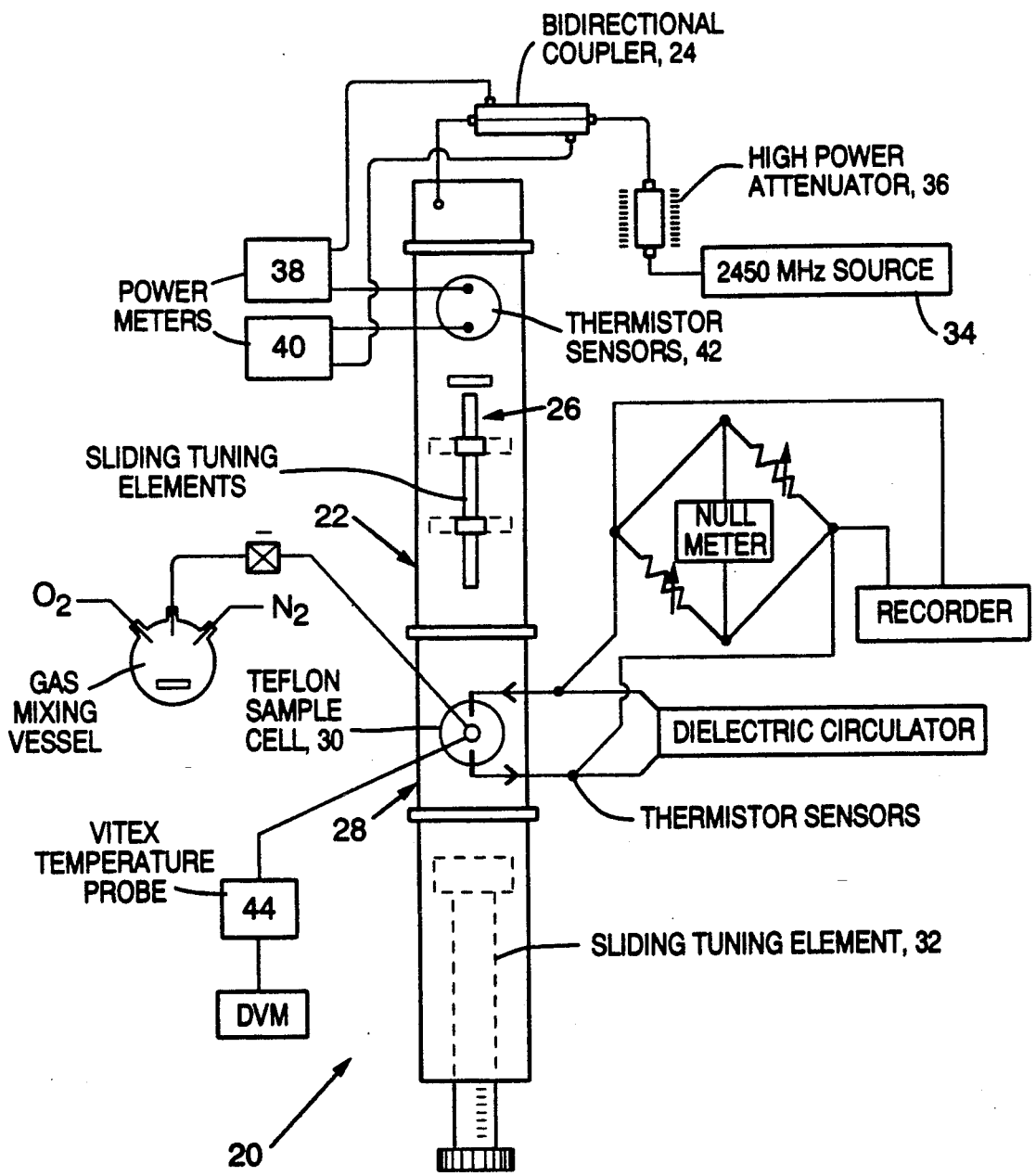
FIG. 7 is a schematic representation of a 2450 MHz electromagnetic field exposure device which can be utilized in the invention.
Figure 8:
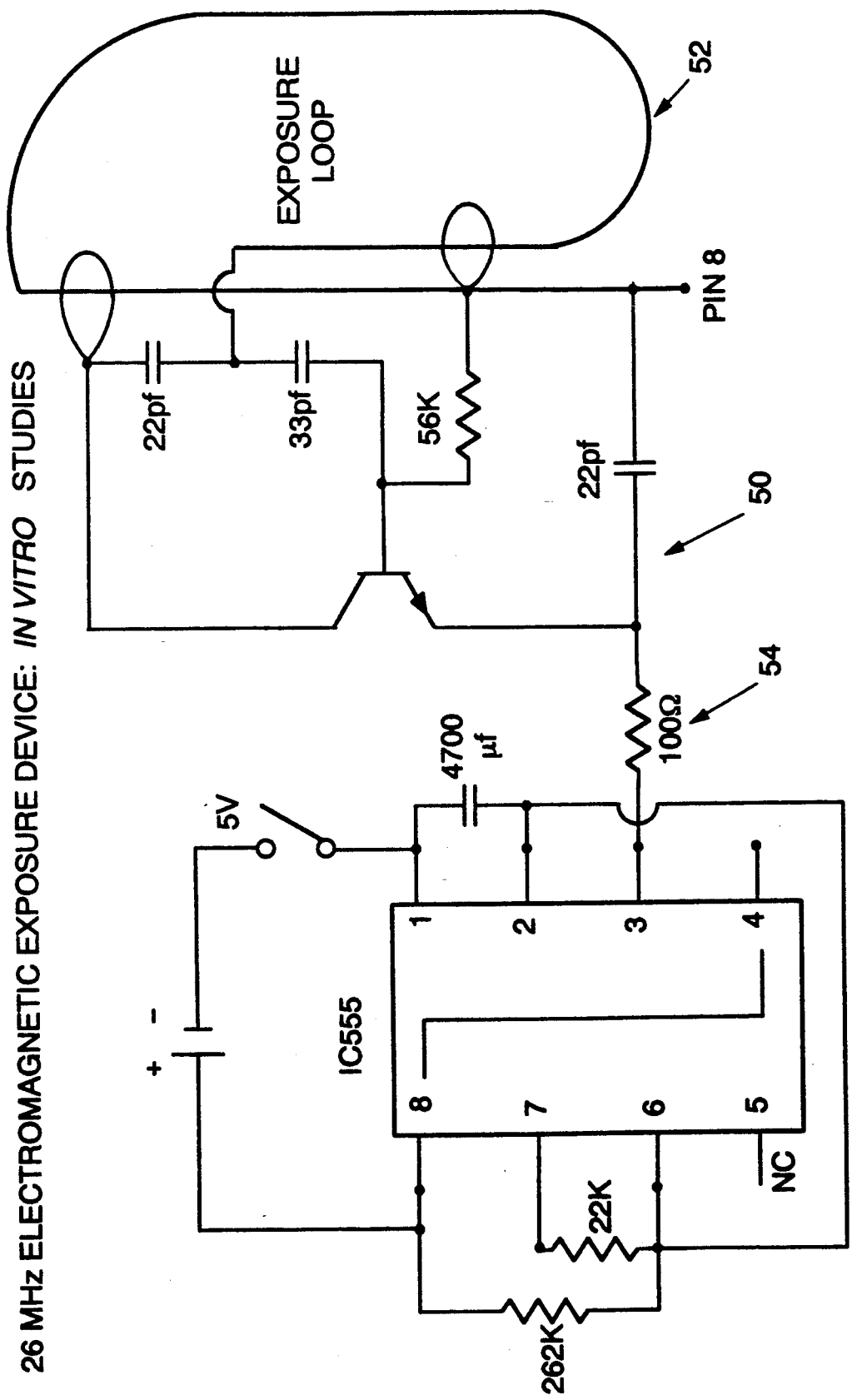
FIG. 8 is a schematic view of an alternate 26 MHz electromagnetic exposure device which can be utilized in the technique of the present invention.

FIGS. 7 and 8 illustrate the laboratory equipment employed in the in vitro exposures to electromagnetic fields of 2450 MHz in frequency. In order to subject liposome suspensions to such nonionizing fields during the technique of the present invention, a microwave waveguide device 20 of the type illustrated in FIG. 7 was utilized. This microwave waveguide device 20 is described in greater detail in *Radiation Research*, 102: 190 (1985).

Figure 7A:
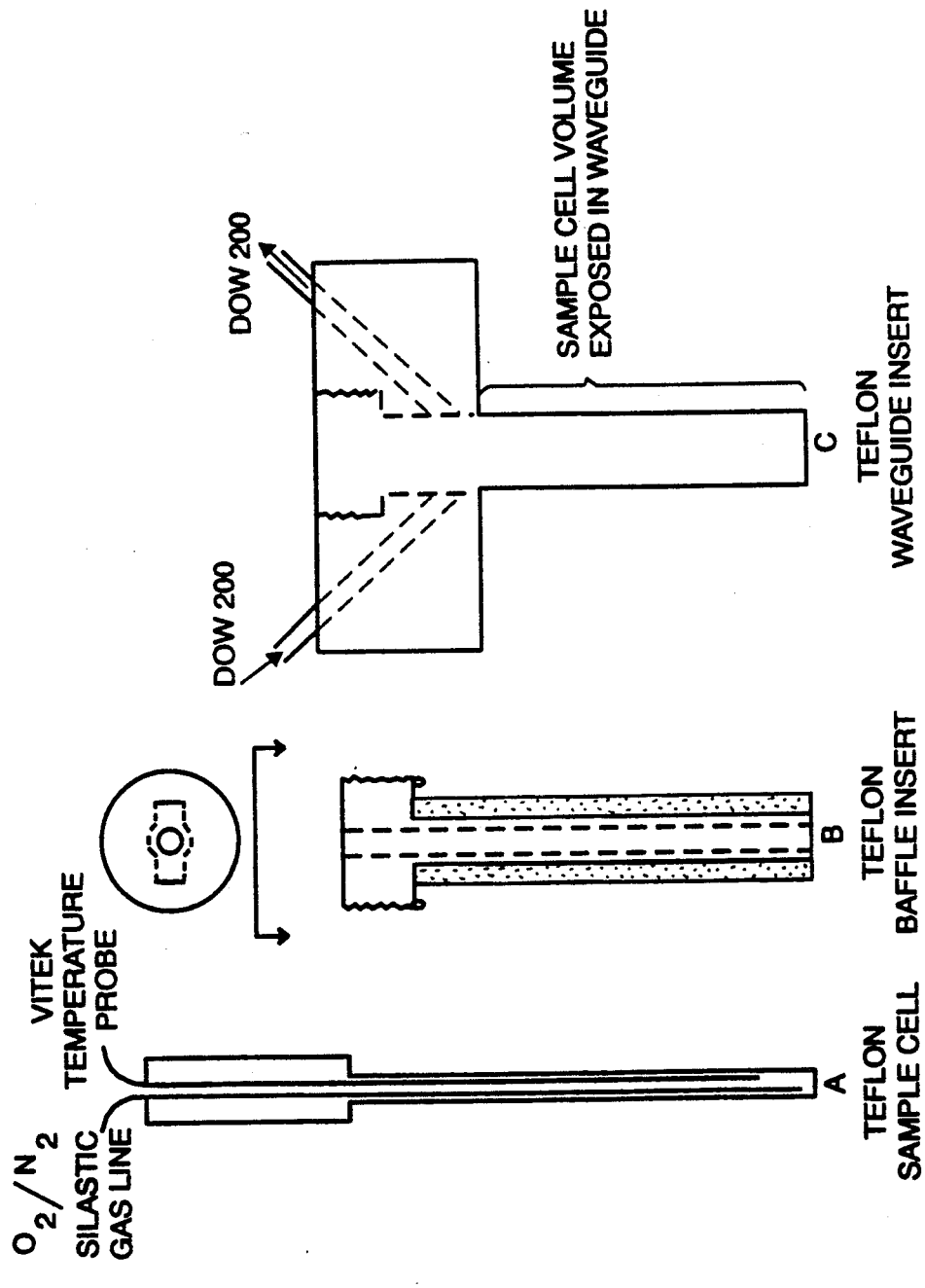
FIG. 7A shows a sample cell for use in the exposure assembly of FIG. 7.

More specifically device 20 is able to generate a well-defined field of 2450 MHz within a waveguide section 22. Waveguide section 22 is made up of four portions: a coaxial to cable coupler 24; an inductive/capacitive tuning element 26; an exposure section 28 incorporating therein a Teflon exposure cell 30; and a sliding short tuning element 32. The waveguide device 20 is energized by a power generator such as a Raytheon PGM-10 power generator 34 that delivers the field first to a power attenuator 36 and then through the bidirectional coupler 24. Forward and reflected power is detected in the waveguide device 20 by means of two conventional power meters 38 and 40 attached to two power sensors 42 in the inductive/capacitive tuning element section 26. The exposure cell section 28 has a port through which the Teflon exposure cell 30 is placed to expose liposomes to the appropriate microwave radiation. A high impedanced temperature probe 44 such as a VITEK Electrothermia Monitor, as shown in FIG. 7A, that is noninteracting with the microwave field is placed in the liposome suspension during exposures to monitor the sample temperature. In addition, 0.2 $\mu$m filtered gas (mixtures of $N_2$ and $O_2$) is bubbled (0.09LPM) into the values of $pO_2$ and to continually circulate the suspension to avoid both liposome settling and the formation of thermal hot spots. The exposure cell 30 is temperature regulated by circulating dodecane or DOW-200 through a circulation jacket that surrounds a sample compartment. A Wheatstone bridge assembly is also used to continually monitor temperature of the dielectric coolant flowing into and out of the exposure cell 30. Although the fields to which the liposomes are subjected by the waveguide device 20 illustrated in FIG. 7 of the drawings is approximately 2450 MHz it should be realized that a wide range extending from 26 to 2450 MHz can effect rapid release of drugs and/or chemical from liposomes. Power requirements for continuous wave 2450 MHz radiation are up to approximately 60 mW/gram of tissue for a time period ranging from less than one nanosecond to many minutes, preferably between about 1 second and 15 minutes, based upon the desired treatment. This absorbed power requirement can be significantly reduced for sources that operate in the pulsed mode. For example a pulsed device capable of generating microwaves at approximately 26 MHz is described hereinbelow. In such a case average absorbed power requirements may be reduced to approximately $10^{-7}$ watts/gram of tissue.

Further information about computation of the specific absorbed dose (SAR) for 2450 MHz exposures is presented below in the section on general laboratory procedures.

In addition to the exposure of liposomes by 2450 MHz fields in the manner presented hereinabove, liposomes can also be exposed to lower frequency electromagnetic fields of, for example, 26 MHz and all frequencies in between. For such exposure, a device 50 of the type illustrated in FIG. 8 can be utilized. This type of generating device 50 incorporates a small radiating antenna loop 52. This device generates a 26 MHz pulsed field with the following characteristics: 80 usec pulse length; 1000 usec cycle length; 1 kHz repetition rate; and 10 uW/cm2 incident power at the center of the loop. To conduct in vitro exposures, loop 52 is placed into a waterbath to establish and control a specific temperature, and liposomes are placed in the center of loop 52 in a small plastic tube of 20 mm×7 mm. Loop 52 is activated by circuit 54 and after exposure to the low frequency field, the liposomes are analyzed for drug release.

In vivo exposures to nonionizing field were performed as described below in the technical section on general laboratory procedures. The experiments using 26 MHz fields employ the same source generator depicted in FIG. 7 which is fed via a coaxial cable into a contact applicator commercially available from ELMED Corporation, Addison Ill. (Model 3013). Any commercial applicator designed for this frequency range would be suitable.

In Vitro Experimental Studies

Figure 9:
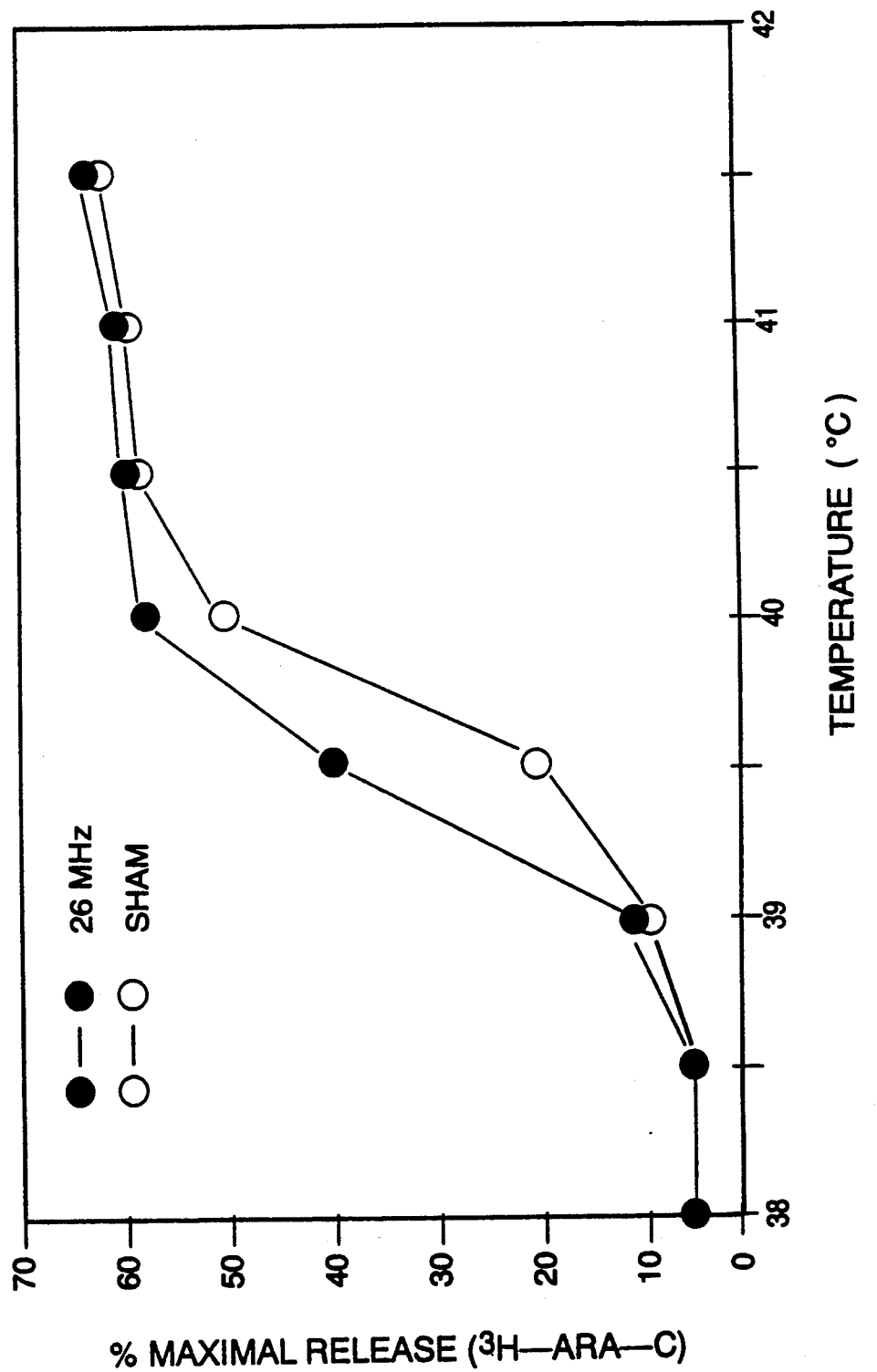
FIG. 9 is a graphical representation of increased liposome permeability in liposome membranes subjected to 26 MHz fields utilizing the technique of the present invention.

Effects of Nonionizing Fields on Drug Release From Liposome Systems: 26 MHz Fields The effect of a relatively low frequency, nonionizing electromagnetic field of 26 MHz on liposome permeability is illustrated in FIG. 9. In these experiments DPPC:DPPG (4:1 weight ratio) liposomes were employed that possessed a phase transition temperature at approximately 40.0° C. These liposomes were loaded with the tritiated cancer drug 3H-ARA-C as a drug marker and suspended in buffered saline. In the absence of the 26 MHz field, as aliquots of liposomes received a 15 minute treatment at temperatures between 39°–42° C., the liposomes displayed a marked increase in permeability of about 20% at approximately 40.0° C., which corresponds to Tc. In the presence of the field (10 uW/gm) these liposomes released approximately 40% of the drug at 40.0° C. This represents a doubling of drug release due to treatment of the liposomes with the 26 MHz field. These results indicate that low frequency fields are effective in triggering drug release. The use of nonionizing fields within the frequency limits of about 26 MHz and 2450 MHz(see below) is encompassed within the scope of this invention.

Effects of Nonionizing Fields of Drug Release From Liposome Systems: 2450 MHz Fields A series of experiments similar to those described above for FIG. 9 were performed using 2450 MHz fields.

Figure 10:
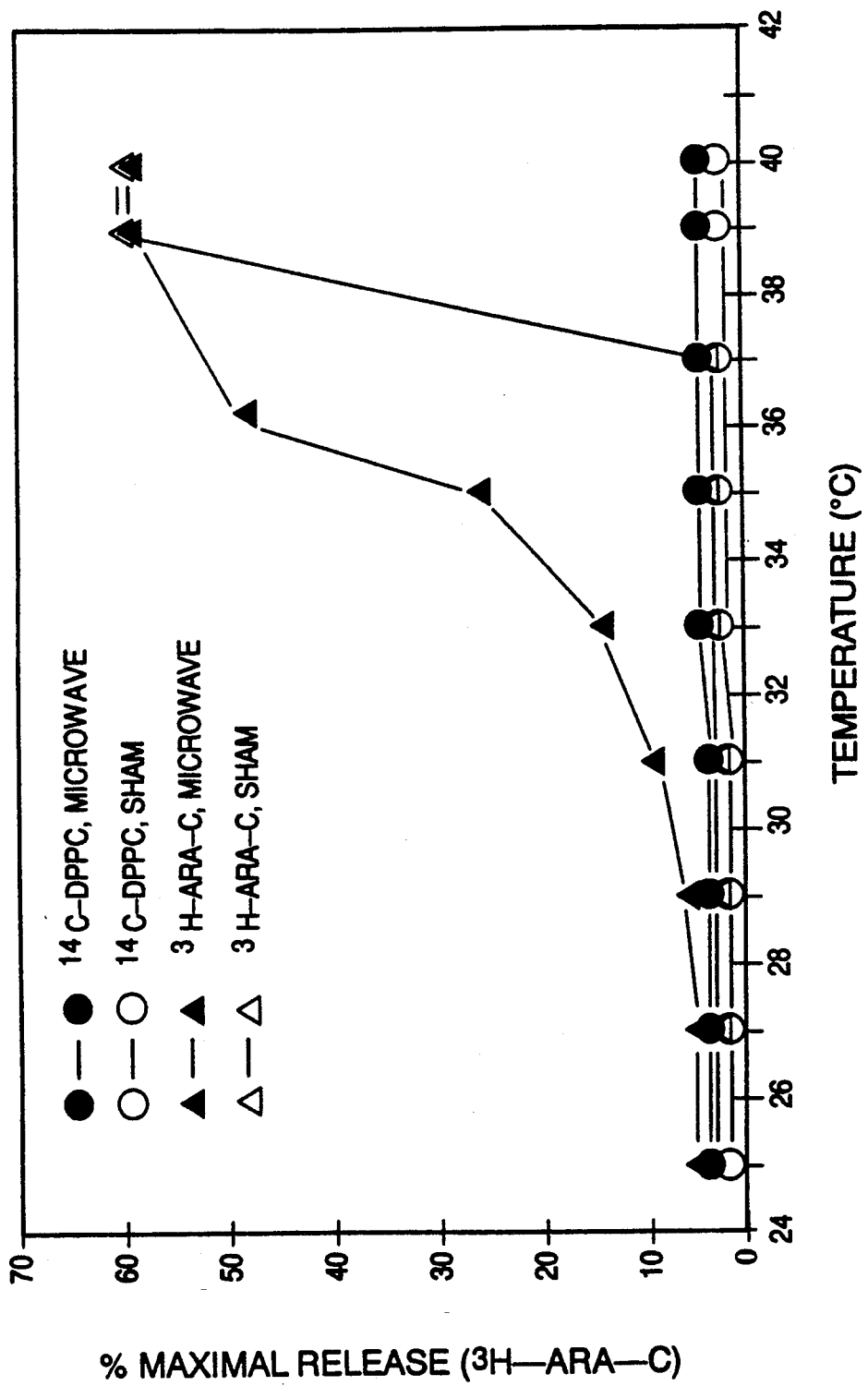
FIG. 10 is a graph showing the effect of microwave fields on drug release from DPPC:DPPG liposomes in buffered saline.

FIG. 10 illustrates the effect of 2450 MHz fields on drug release from DPPC:DPPG liposomes that were loaded with 3H-ARA-C in the aqueous interior, and with 14C-DPPC in the lipid membrane. These exposures were performed with the liposomes aliquoted into buffered saline and exposed at 6 mW/gm for 15 minutes at each of the temperatures shown. The two isotope markers employed enabled the monitoring of drug release from the liposome interior, and the release of phospholipids from the liposome membrane. The latter is important because if lipid components themselves are released by treatment with the field it will indicate that the field is disrupting the liposome membrane, instead of creating a transient pore or channel for drug release.

Data in FIG. 10 depict the marked increase in liposome permeability that occurs spontaneously in the absence of microwave fields at approximately 40° C., which corresponds to Tc for DPPC:DPPG liposomes. This was also observed in the data shown in FIG. 9. In the presence of the 2450 MHz fields an increase in permeability was observed at lower temperatures such that at approximately 35° C., 40% of drug release was triggered. This indicates that these relatively high frequency fields are effective in triggering drug release, and that this occurs at temperatures not associated with Tc. Thus, microwave-triggered drug release occurs at temperatures below Tc, and this demonstrates that the microwave field effect is operating on liposome vesicles in the solid (gel) state. In addition, the data shown in FIG. 10 for release of 14C-DPPC is very important and demonstrates that no phospholipid membrane components are released during field treatment. This indicates that the 2450 MHz field does not result in disruption of the bilayer yet triggers drug release. These results support the idea that pores or channels are opened transiently in the liposome membrane during field treatment to enable drug leakage from the liposomes.

Figure 11:
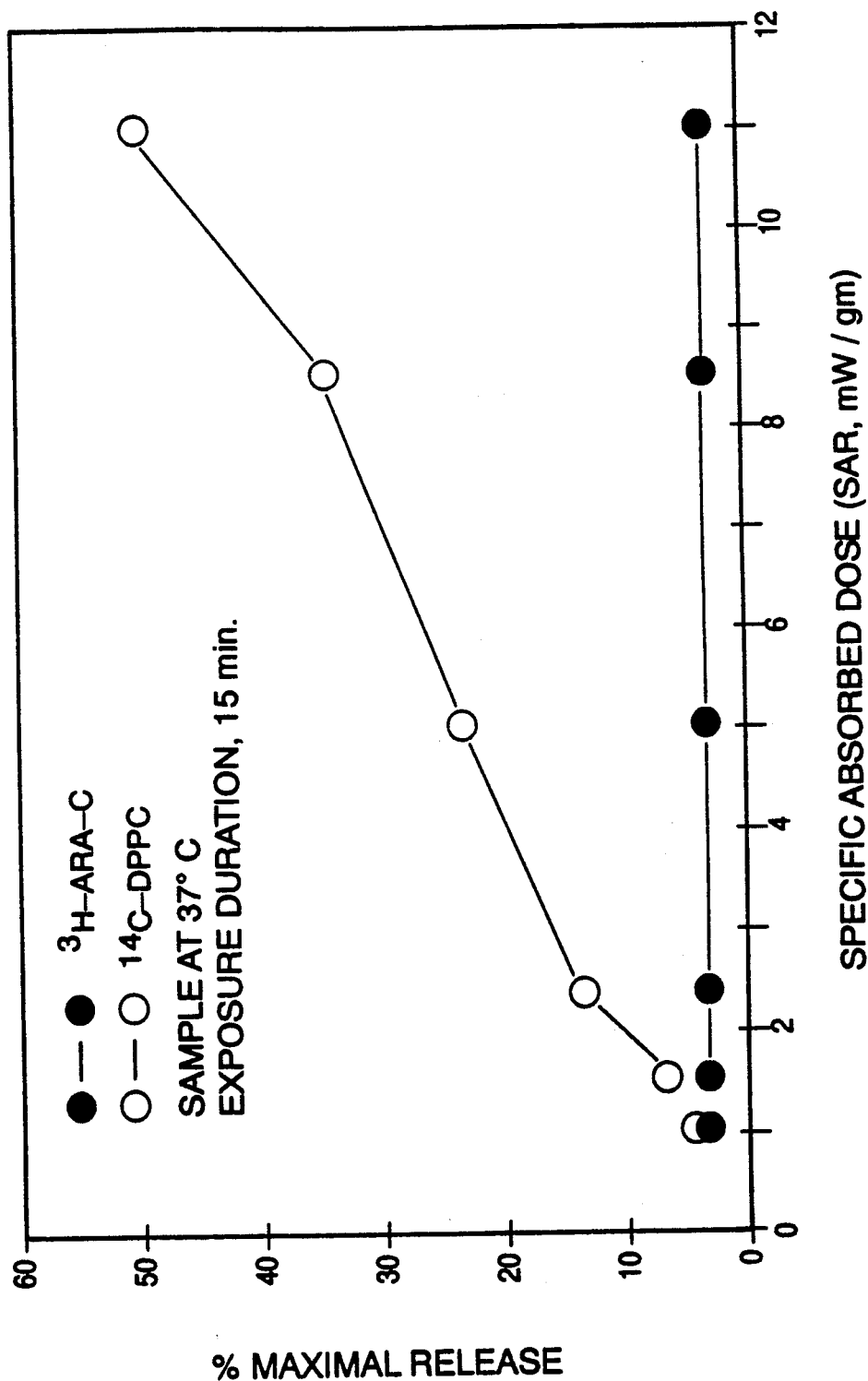
FIG. 11 is a dose-response characterization of absorbed power of the microwave field on liposome drug release.

A series of studies were performed to determine the dose-response relationship for the microwave effect on DPPC:DPPG liposomes shown in FIG. 10. Presented in FIG. 11 are data for these liposomes in which a 15 minute exposure was performed at 37° C.; liposomes were maintained in buffered saline. It is apparent that as the amount of specific absorbed power (SAR) in the sample increases there is a corresponding linear increase in drug release (3H-ARA-C). Importantly, the isotopically labelled DPPC (14C-DPPC) is not released from the liposome membrane. This further supports the idea that the liposome membrane is not irreversibly disrupted by the nonionizing field during drug release.

Figure 12:
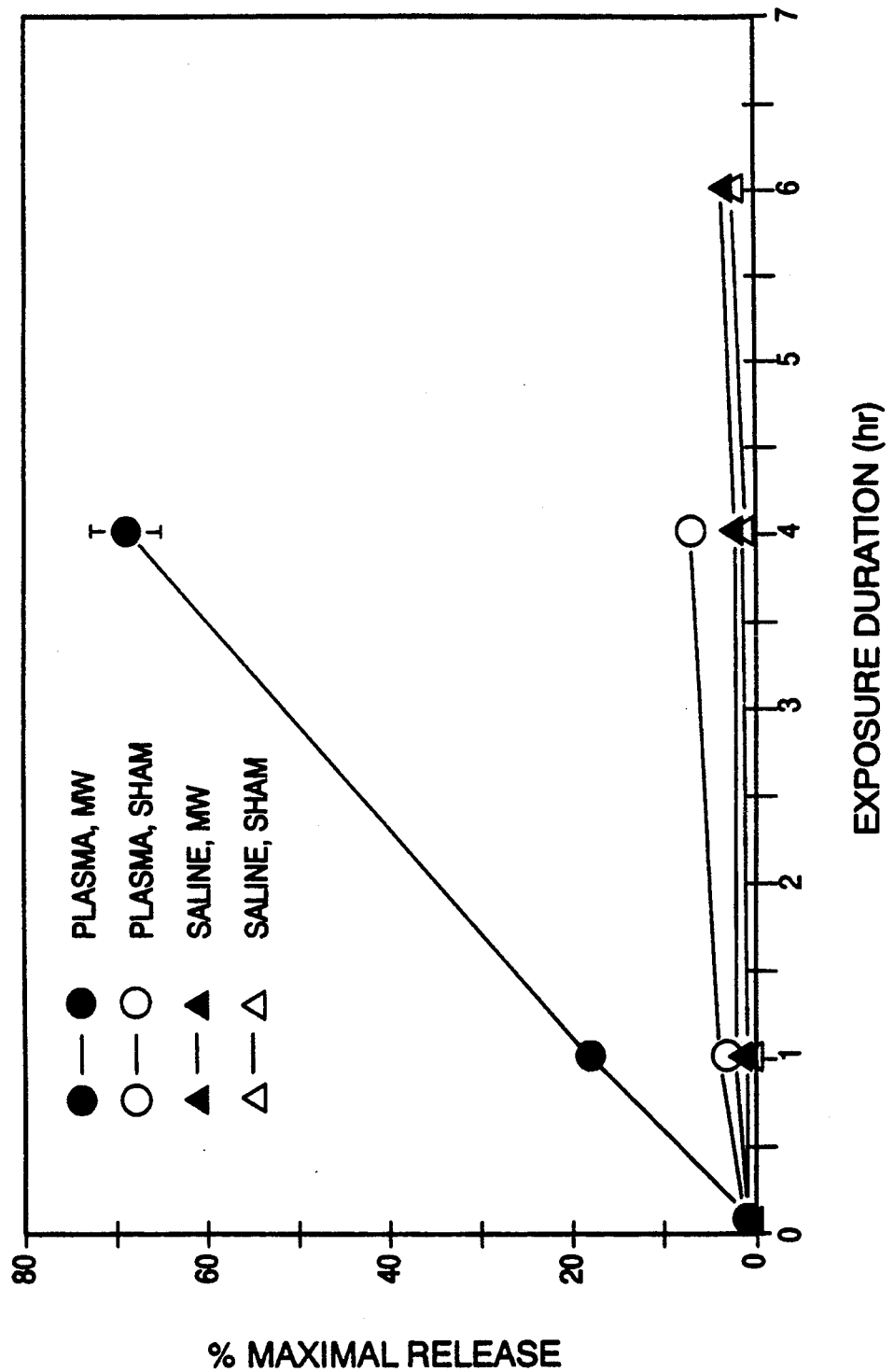
FIG. 12 shows the effect of microwave fields on drug release from DPPC:DPPG liposomes in plasma buffer or saline buffer as a function of time.

Additional studies were performed on these liposomes to determine if the presence of human plasma would influence the microwave field effect. This is relevant to the use of nonionizing fields to trigger drug release from liposomes in the in vivo environment. FIG. 12 depicts the effect of 2450 MHz fields on DPPC:DPPG liposomes that were maintained in buffered saline or in 50% human plasma and 50% buffered saline at 37° C. Exposures were performed at 0.6 mW/gm and for varying lengths of time indicated in the figure. Two important points are illustrated by these data: (1) plasma significantly enhances microwave-triggered drug release, but not spontaneous drug release; (2) in plasma there is no release of phospholipid membrane components during microwave treatment or during control waterbath treatments.

Figure 13:
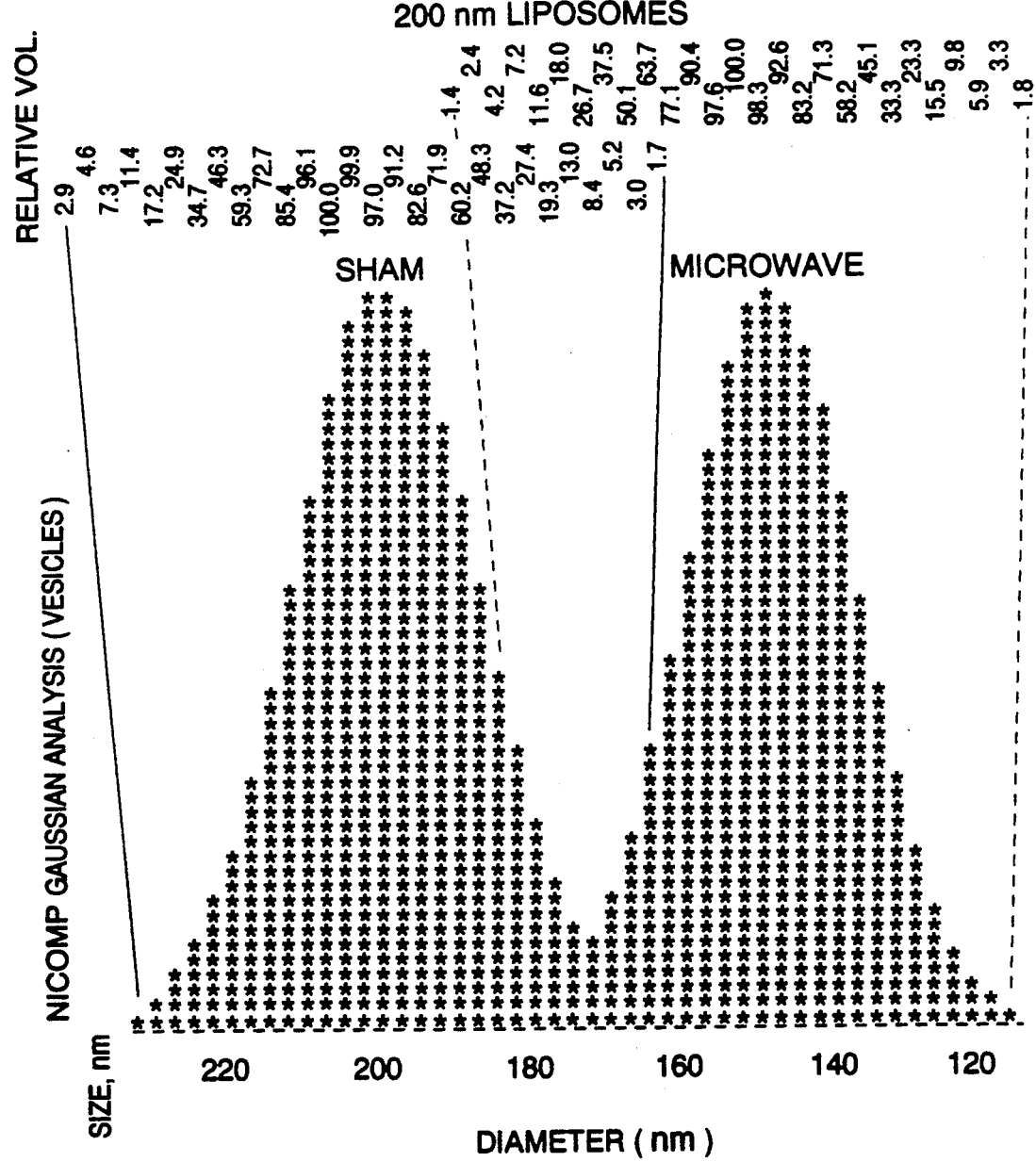
FIG. 13 depicts the effect of microwave fields on DPPC:DPPG liposome size.

To further investigate the question of membrane interaction with the applied 2450 MHz field, experiments were conducted in which liposome size was quantitated before and after exposure. Since liposomes on the order of 100-200 nm in diameter are not visible using ordinary light microscopy, liposome size was measured using laser light scattering techniques on a NICOMP 2000 device. FIG. 13 depicts the size distribution of DPPC:DPPG liposomes prior to and after exposure to 2450 MHz fields (6 mw/gm) for 15 minutes at 37° C. Prior to exposure liposome size was approximately 100 nm in radius, and following exposure the average size decreased to approximately 75 nm in radius. Since the liposome membrane does not undergo disruption from the 14C-DPPC studies described above in FIG. 10, this size reduction is most likely the result of membrane fusion in which the liposome is destabilized to split and reseal to produce two smaller vehicles. An analysis of the data supports the interpretation of a split into smaller liposomes which conserves the total surface area of the original liposome. For example, a comparison of surface area of the liposome prior to and after the exposures reveals that a 100 nm radius liposome has twice the surface area than does a 75 nm radius liposome. This corresponds to a splitting in half of the liposome during field treatment. Therefore, this size reduction data support the mechanism of drug release involving pore or channel formation and a membrane fusion event to create two smaller liposome vesicles.

Figure 14:
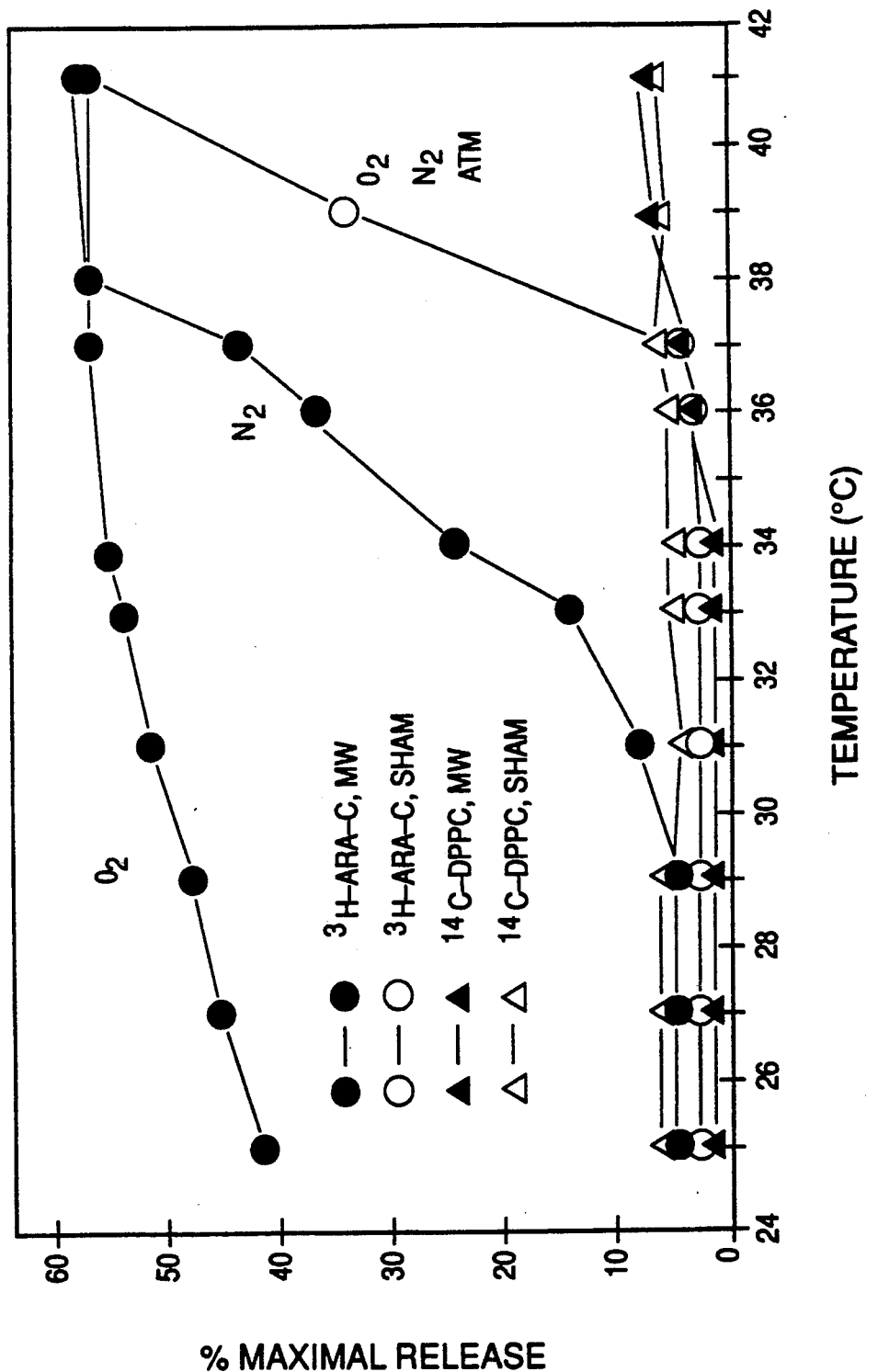
FIG. 14 shows the effect of oxygen, nitrogen, and atmospheric air on microwave-triggered drug release from DPPC:DPPG liposomes.

The effect of oxygen and nitrogen on microwave-triggered drug release was investigated since oxygen partial pressure varies considerably in vivo. FIG. 14 illustrates the effect of a saturated oxygen environment ($O_2$), a saturated nitrogen environment ($N_2$), and an atmospheric air environment (ATM), on microwave-triggered drug release from DPPC:DPPG liposomes. Microwave exposures were for 1 5 minutes at 6 mW/gm at the temperatures shown. The control data indicate that neither oxygen or nitrogen had an effect on drug release, or on release of 14C-DPPC, as temperature was varied over 25°-42° C. In contrast, during microwave treatment the most striking effect shown is for oxygen treatment which potentiates microwave-triggered drug release at all temperatures studied. For example, at 31° C. the presence of oxygen facilitates a 53% release of drugs by microwaves, whereas in the presence of nitrogen or atmospheric air there is only a 8% release of drugs. Thus, oxygen significantly enhances the microwave-triggered release of drug from liposomes, and this occurs at temperatures where the liposome's membrane is below Tc and thus in the solid (gel) state.

Figure 15:
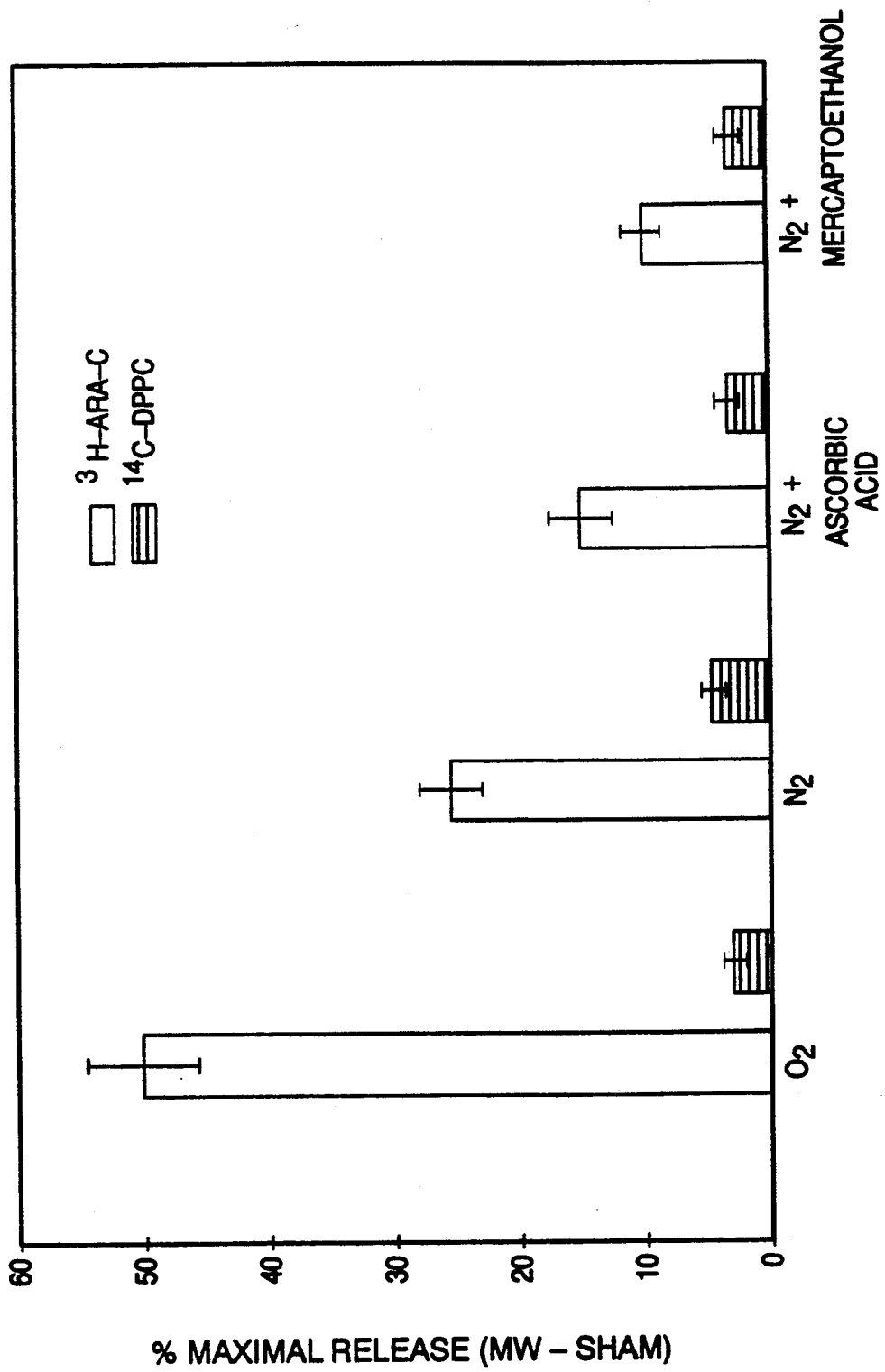
FIG. 15 illustrates the effect of antioxidants in the liposome buffer on microwave-triggered drug release from DPPC:DPPG liposomes.

To further investigate the potentiation of oxygen on microwave-triggered drug release, a series of studies were performed with antioxidant agents. If microwaves were catalyzing the oxidizing action of oxygen then antioxidants would neutralize this effect. In these experiments the antioxidants ascorbic acid and mercaptoethanol were employed in the buffered saline media into which DPPC:DPPG liposomes were suspended: exposures were at 6 mW/gm for 15 minutes at 37° C. FIG. 15 depicts the protective effect observed for both ascorbic acid and for mercaptoethanol. A 50% increase in drug release was observed for oxygen treatment plus microwaves, and this was reduced to 15% when ascorbic acid (Vitamin C) was present, and to 10% when mercaptoethanol was present. These data indicate that a significant chemical role is played by oxygen in potentiating the release of drugs from liposomes during exposure to microwave fields and that antioxidants act to partially neutralize this effect.

Figure 16:
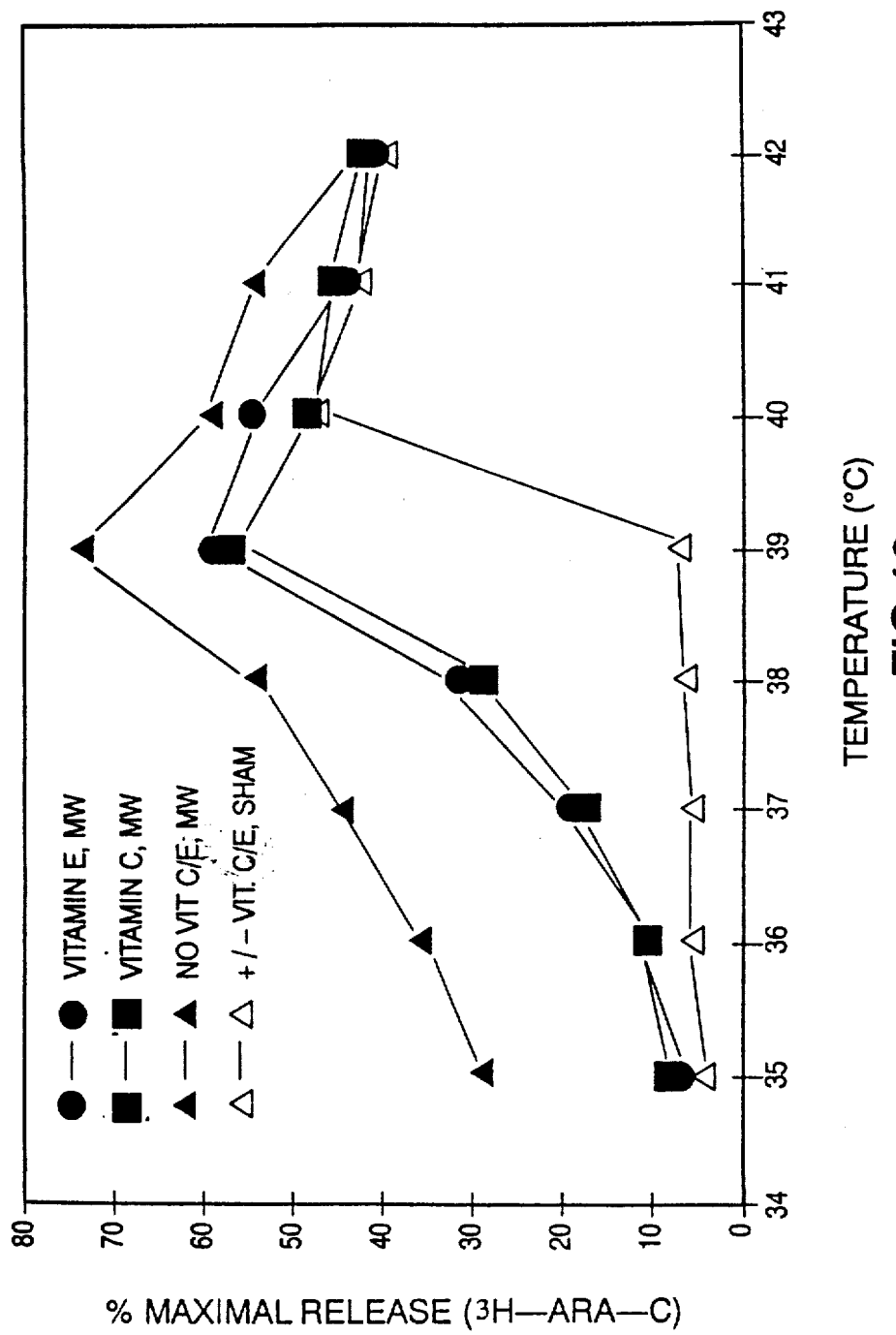
FIG. 16 demonstrates the effect of antioxidant-modification of DPPC:DPPG liposomes on microwave-triggered drug release.
Figure 29:
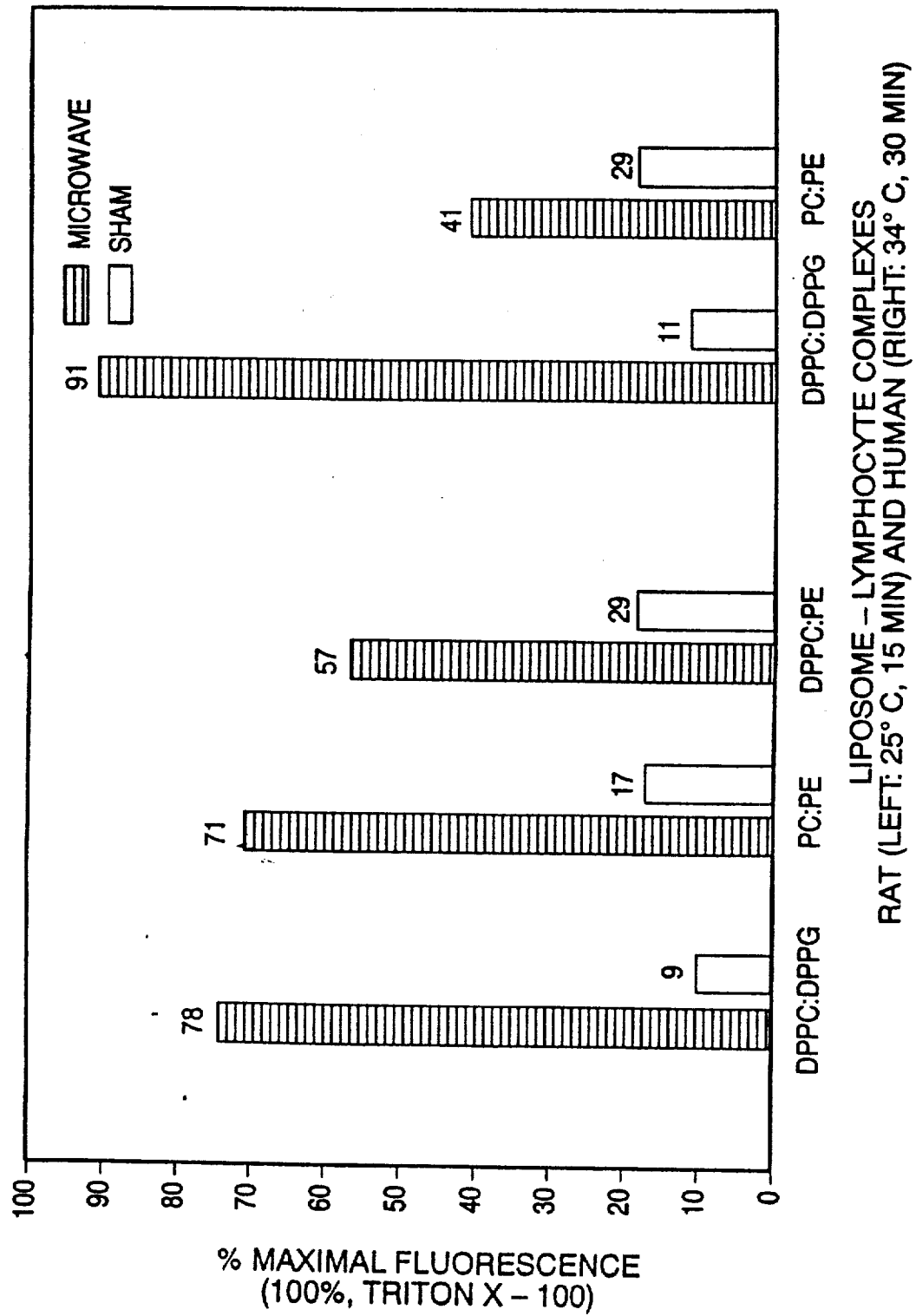

The role of oxygen and antioxidants was further investigated by modifying the DPPC:DPPG liposomes with antioxidant agents: α-tocopherol (Vitamin E) was incorporated at 2% mole fraction into the liposome membrane; and ascorbate (Vitamin C) was loaded at 35 mM into the interior aqueous compartment of the liposome. FIG. 16 depicts the data from microwave treatment experiments in which exposures were performed at 6 mW/gm for 15 minutes at the temperatures shown. The drug release data for the sham-exposed, control liposomes are consistent with the sham data for DPPC:DPPG liposomes shown hereinabove; a Tc is evident at about 39°-40° C. where drug release occurs spontaneously. Thus, modification of these liposomes with either of these antioxidant agents does not influence the liposome's ability to release drugs. When these liposomes are treated with microwaves both the ascorbate-modified and the α-tocopherol-modified liposomes exhibit increased drug release at temperatures below Tc, where the liposome is in the solid state. Interestingly, a comparison between modified and unmodified liposomes reveals that the microwave field increases drug release greatest for the unmodified liposomes (no antioxidants present). Thus, the protective effect of antioxidants seen in FIG. 15 with the antioxidants in the buffer outside the liposome, is also seen here with the antioxidant agent present in the liposome membrane and in the liposome interior.

Effects of Nonionizing Fields on Drug Release From Liposome Systems Having Membrane Perturbing Agents Which Eliminate the Phase Transition Temperature Tc The effect of addition to the liposome membrane of a perturbing agent such as the lipid cholesterol and such as antibody protein molecules on the phase transition was studied. The action of a perturbing agent on the phase transition is important and defines a class of liposomes lacking a phase transition over a specific temperature range that respond to nonionizing fields such as microwaves.

In FIG. 5 data was presented characterizing the effect of the addition of cholesterol at 40 mole % on the phase transition of DMPC:DMPG liposomes. Cholesterol at this concentration eliminated the phase transition as evidenced by no increase in drug release from these cholesterol-modified liposomes at 23° C., which is the nominal phase transition temperature of the unmodified DMPC:DMPG liposomes. Thus, perturbing agents at sufficient concentration can act to obliterate the phase transition. This effect was studied further.

In FIG. 17 is shown the release of drug from DPPC:DPPG liposomes (as in FIG. 10) at 37° C. with different amounts of added cholesterol to the membranes as indicated on the x-axis. The studies in FIG. 17 were performed in the presence of 50% human plasma:50% saline buffer, or in the presence of 100% buffered saline. At 37° C. in the absence of a 2450 MHz microwave field no drug release is observed for any concentration of added cholesterol, and this is consistent with a lack of permeability at 37° C. seen in FIG. 10. However, in the presence of the 2450 MHz field (6 mW/gm), and at 0% cholesterol, approximately 80% drug release occurred in saline and 1 00% in plasma. This is consistent with microwaves triggering significant drug release at 37° C. as shown in FIG. 10. As the amount of added cholesterol increases from 0% to 50% in FIG. 17 we observe a decrease in microwave-triggered drug release to levels of 40% for plasma, and 20% for buffered saline. Only 5% is observed in the absence of the field. This result is very important and indicates that even when the phase transition is eliminated by the addition of high concentrations of a perturbing agent such as cholesterol nonionizing fields are capable of triggering significant drug release. In addition, it is evident that this drug release phenomenon is more pronounced, or enhanced, in the presence of human plasma.

Figure 18:
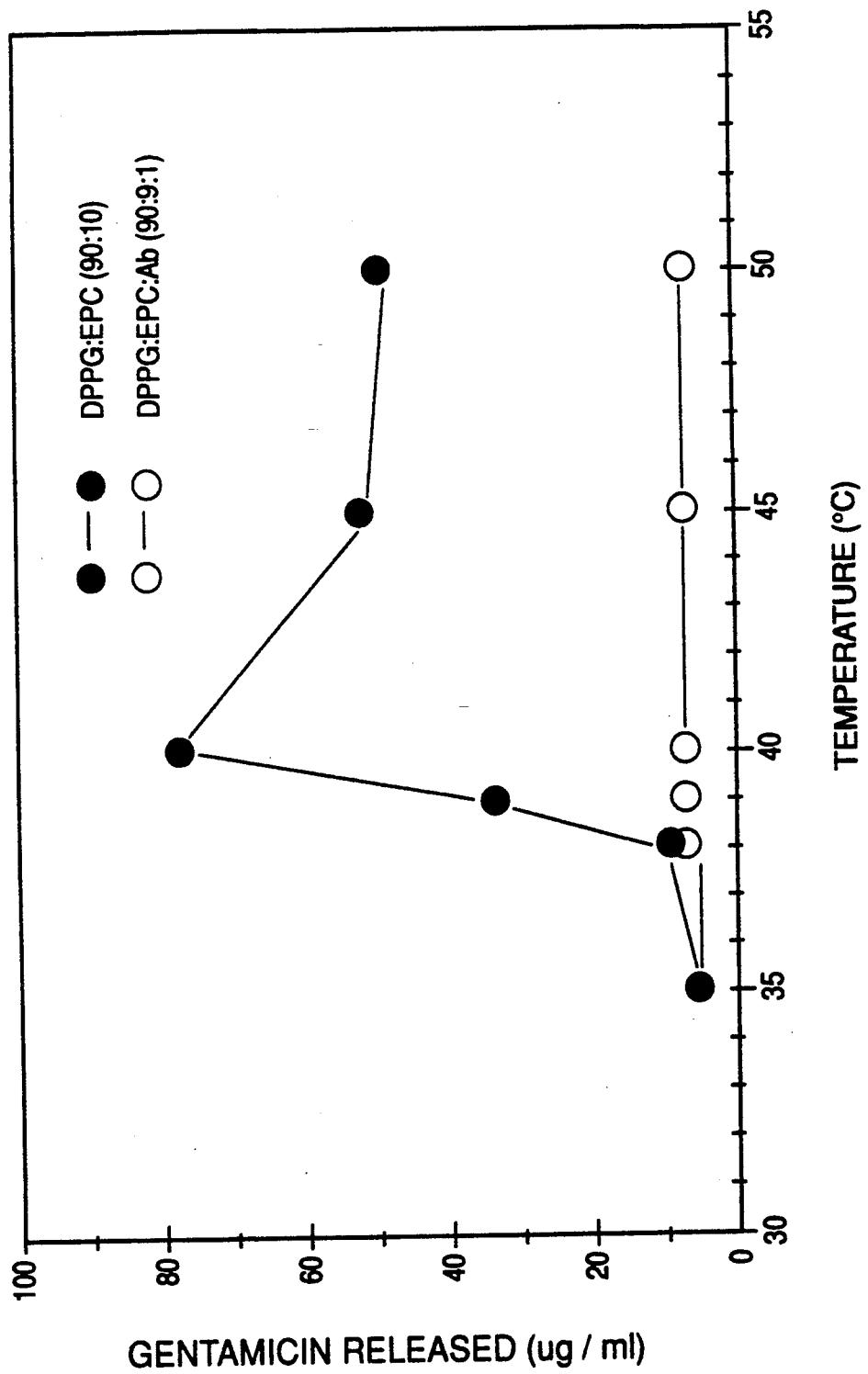
FIG. 18 illustrates the effect of membrane antibody as a perturbing agent on drug release from DPPC:EPC liposomes.
Figure 19:
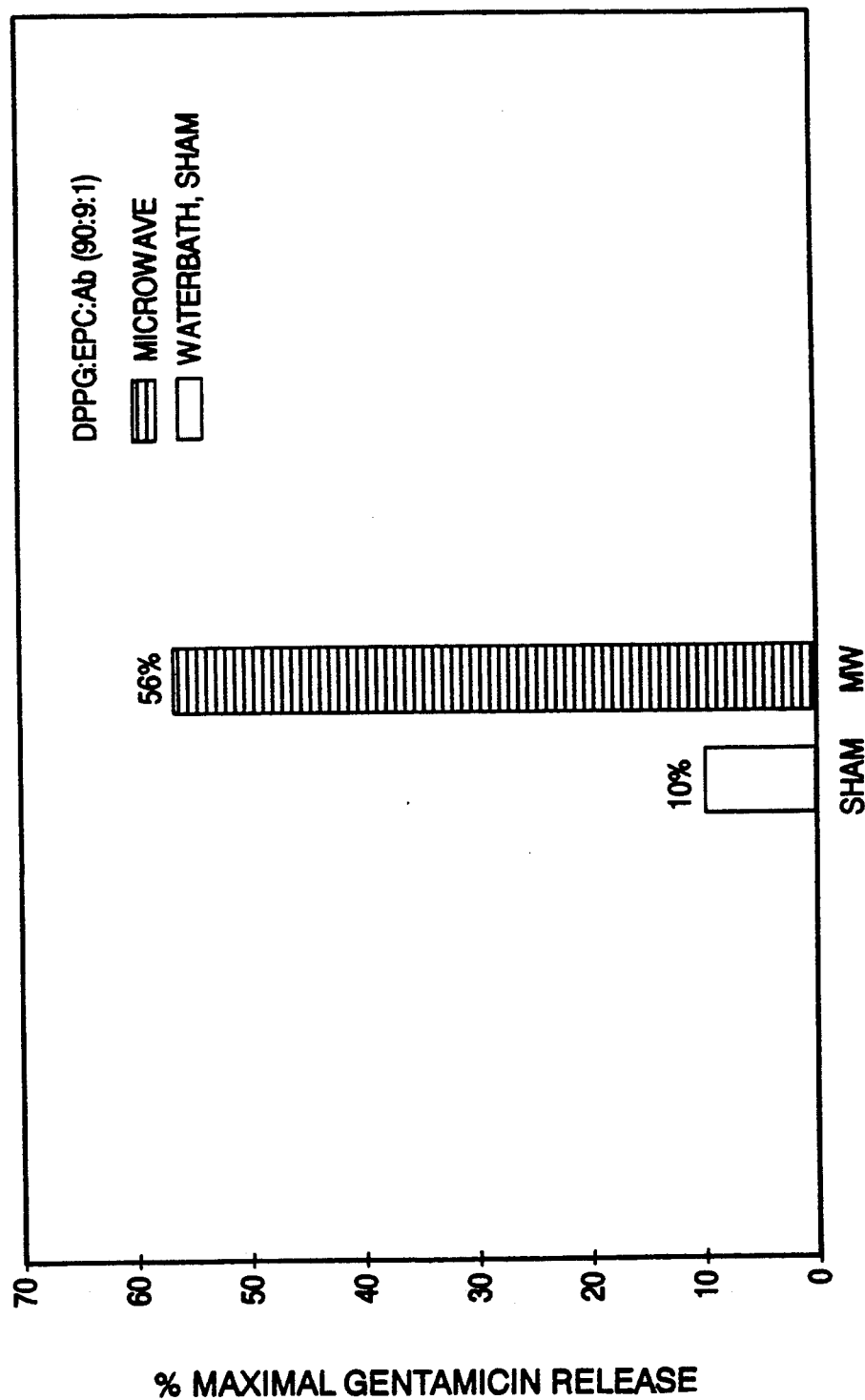
FIG. 19 depicts the effect of microwaves on drug release from antibody-modified, nonphase transition liposomes.

Protein molecules can also be incorporated into the liposome membrane as perturbing agents as described above in FIG. 1 and FIG. 2. Since these agents are important for targeting liposomes to specific sites in the body, it was investigated as to whether antibody-modified liposomes would exhibit microwave-triggered drug release. For these studies human immunoglobulin G (hIgG) was incorporated into the membrane of Gentamicin-loaded, DPPG:EPC (90:10) liposomes which (without hIgG) display a Tc of 40° C. For the incorporation procedure antibody molecules were derivatized with a hydrophobic palmitoyl group so that the antibody would easily insert into the liposome membrane. The molar ratio of the final liposome structure DPPG:EPC:hIgG was 90:9:1. FIG. 18 also shows that in the absence of hIgG in the liposome membrane the liposome vesicle displayed a Tc at approximately 40° C., which is nominal for DPPG liposomes (FIG. 10). In these tests liposomes were maintained at the temperatures shown for 15 minutes, spun down, and Gentamicin was measured in the supernatant using a RIA assay. FIG. 18 also shows that the addition of hIgG as a perturbing agent to the liposome membrane eliminated Tc. These liposomes were tested for microwave-triggered drug release. Shown in FIG. 19 are data demonstrating that microwaves act to trigger significant drug release in antibody-modified liposomes maintained in plasma buffer (50% human plasma, 50% saline buffer). Exposures were performed at 6 mW/gm, 15 minutes, 37° C.

An additional way to eliminate Tc is to add nonidentical phospholipids to the liposome membrane. A mixture of different hydrocarbon chain phospholipids will inhibit the formation of a phase transition. EPC was added to DPPG phospholipids. The resultant liposome vesicles (DPPG:EPC; 10:90) were loaded with the fluorescent drug marker 6-carboxyfluorescein (6-CF), and tested for microwave-triggered drug release. The temperature dependence of these liposomes in HEPES buffer:human plasma (1:1) is shown in TABLE 1.

TABLE 1

| Temperature Dependence of EPC-Modified DPPG Liposomes | | | | |
|---|---|---|---|---|
| Run No. | Temp. °C. | FLUOR | MAX FLUOR | % Released |
| 1 | 4 | 0.6 | | |
| 2 | 4 | 56.9 | 500.2 | 11% |
| 3 | 20 | 232.74 | 83.2 | 48% |
| 4 | 25 | 345.4 | 511.6 | 68% |
| 5 | 30 | 341.1 | 465.8 | 73% |
| 6 | 35 | 359.3 | 474.1 | 76% |
| 7 | 40 | 405.9 | 517.7 | 78% |
| 8 | 45 | 406.7 | 477.1 | 85% |
| 9 | 50 | 350.1 | 421.5 | 83% | a. Run 1: Plasma:HEPES (1:1), No liposomes present
b. Runs 2 to 9: Plasma:HEPES (1:1), Liposomes present.

The above data indicate that EPC-modified liposomes do not display a marked increase in drug release indicative of a phase transition at 40° C., and can therefore be regarded as nonphase transition liposomes over this temperature region. In other experiments DPPG:EPC:aT (9.9:90:0.1) liposomes were prepared and tested with a similar temperature insensitivity of drug release. As temperature was varied from 20°-50° C. the drug Gentamicin was released at a constant level of only 19% of maximal release which was induced by the addition of Triton-X-100 surfactant.

Figure 20:
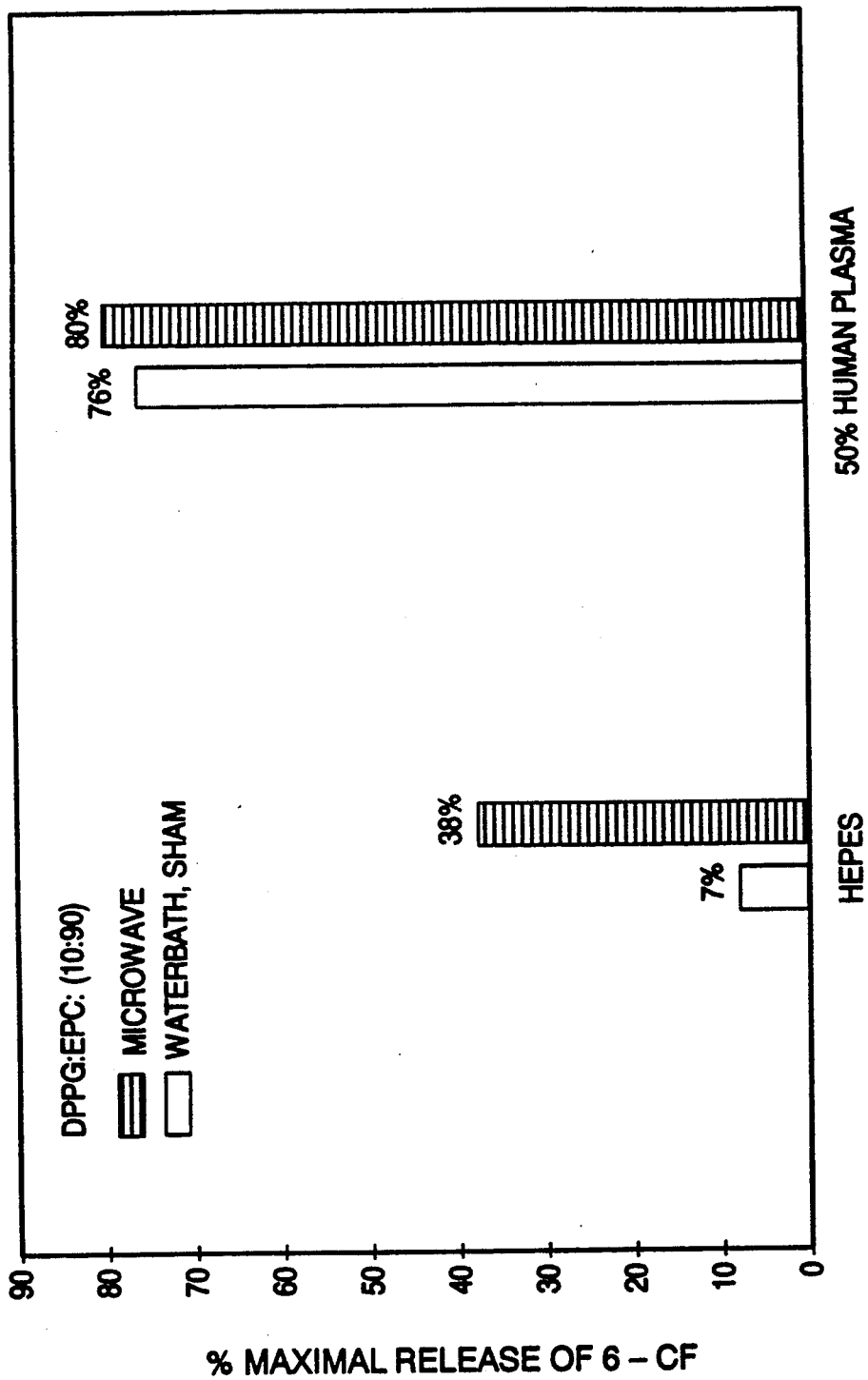
FIG. 20 shows the effect of membrane phospholipid as a perturbing agent on microwave-triggered drug release from nonphase transition DPPG:EPC liposomes.

These liposomes were evaluated for microwave-triggered drug release. Microwave exposures were conducted at 6 mW/gm, 15 minutes, 37° C. FIG. 20 depicts drug release data for EPC-modified DPPG liposomes maintained in HEPES buffer or HEPES:human plasma (1:1). A significant increase in drug release was triggered by microwave fields for liposomes maintained in HEPES buffer.

Two additional liposome systems were chosen for study to investigate in greater depth the temperature dependence of microwave-triggered drug release from nonphase transition liposomes. To do this DMPC:DMPG and DPPC:DPPG liposome vesicles systems were used unmodified, or modified with 30% mole fraction cholesterol incorporated in the membrane. As was shown in FIG. 17 this modification renders the liposome a nonphase transition vesicle over a temperature that includes the nominal Tc for the vesicle. Microwave exposures for FIGS. 21-24 were at 6 mW/gm, 15 minutes.

Figure 21:
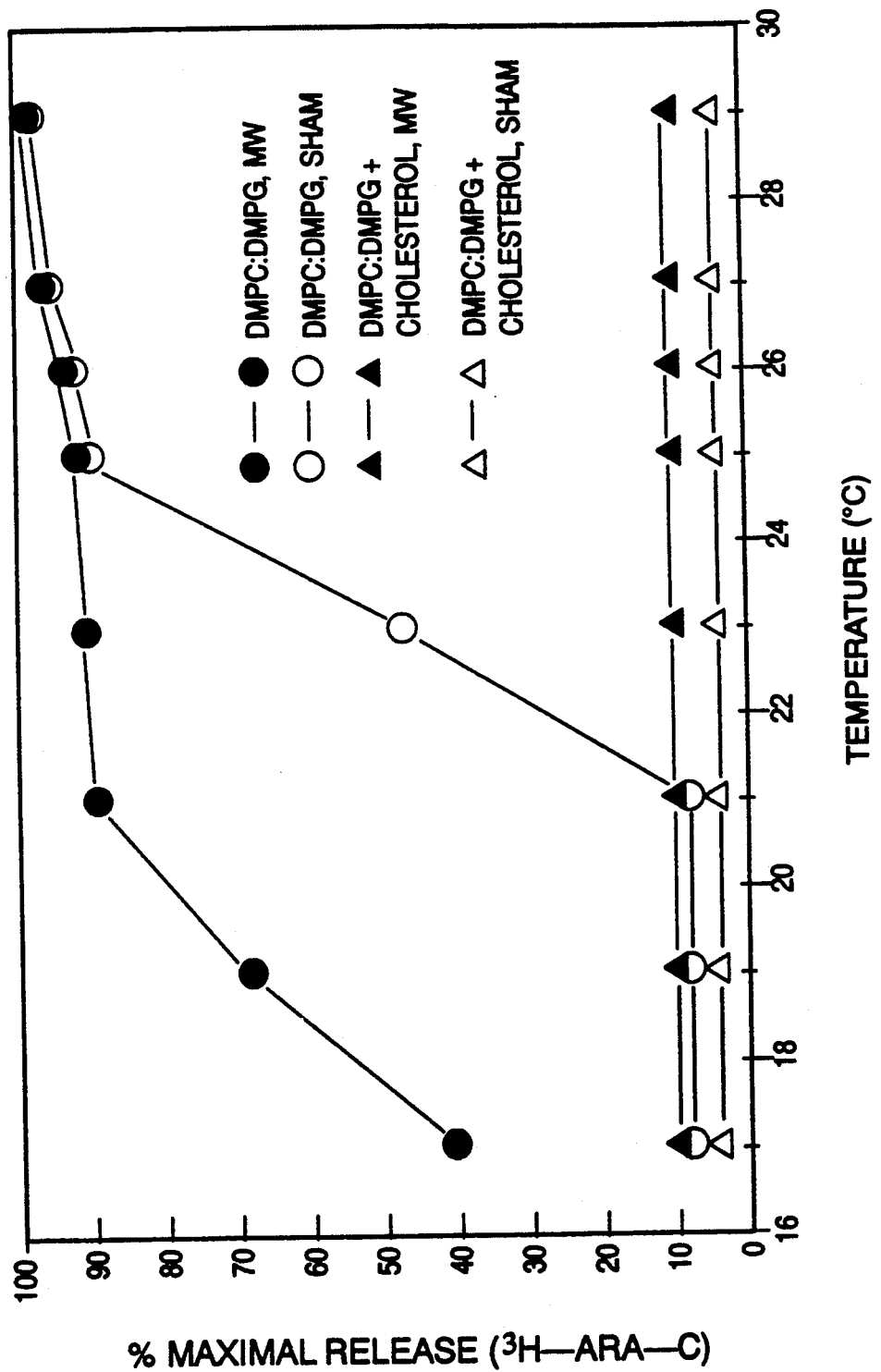
FIG. 21 illustrates the effect of microwave fields on drug release from phase transition and from nonphase transition DMPC:DMPG liposomes in saline buffer.

The temperature dependence of microwave-triggered drug release for DMPC:DMPG liposomes maintained buffered saline is shown in FIG. 21. Unmodified, phase transition liposomes display a nominal Tc of about 23° C., as described hereinabove. When these liposomes were treated with microwaves a significant increase in drug release is observed at temperatures below Tc. Cholesterol-modified, nonphase transition liposomes do not display a Tc over this temperature range and exhibit a level of drug release of about 5% over the entire temperature range studied. When these nonphase transition liposomes are treated with microwaves they show an increase in drug release to 10-12% over this temperature range, which includes temperatures below, at, and above the nominal Tc. Thus, cholesterol-modified, nonphase transition DMPC:DMPG liposomes exhibit microwave-triggered drug release at all temperatures studied.

It is important to note the difference between microwave-triggered drug release for phase transition vs. nonphase transition liposomes. Phase transition liposomes display increased drug release in the presence of microwaves at temperatures below Tc, where the membrane is in the solid state. In contrast, nonphase transition liposomes display microwave-triggered drug release at temperatures that are below, at, and above the original Tc before the liposomes were modified with perturbing agents. This generalization is also applicable to data shown below in FIGS. 22-24.

Figure 22:
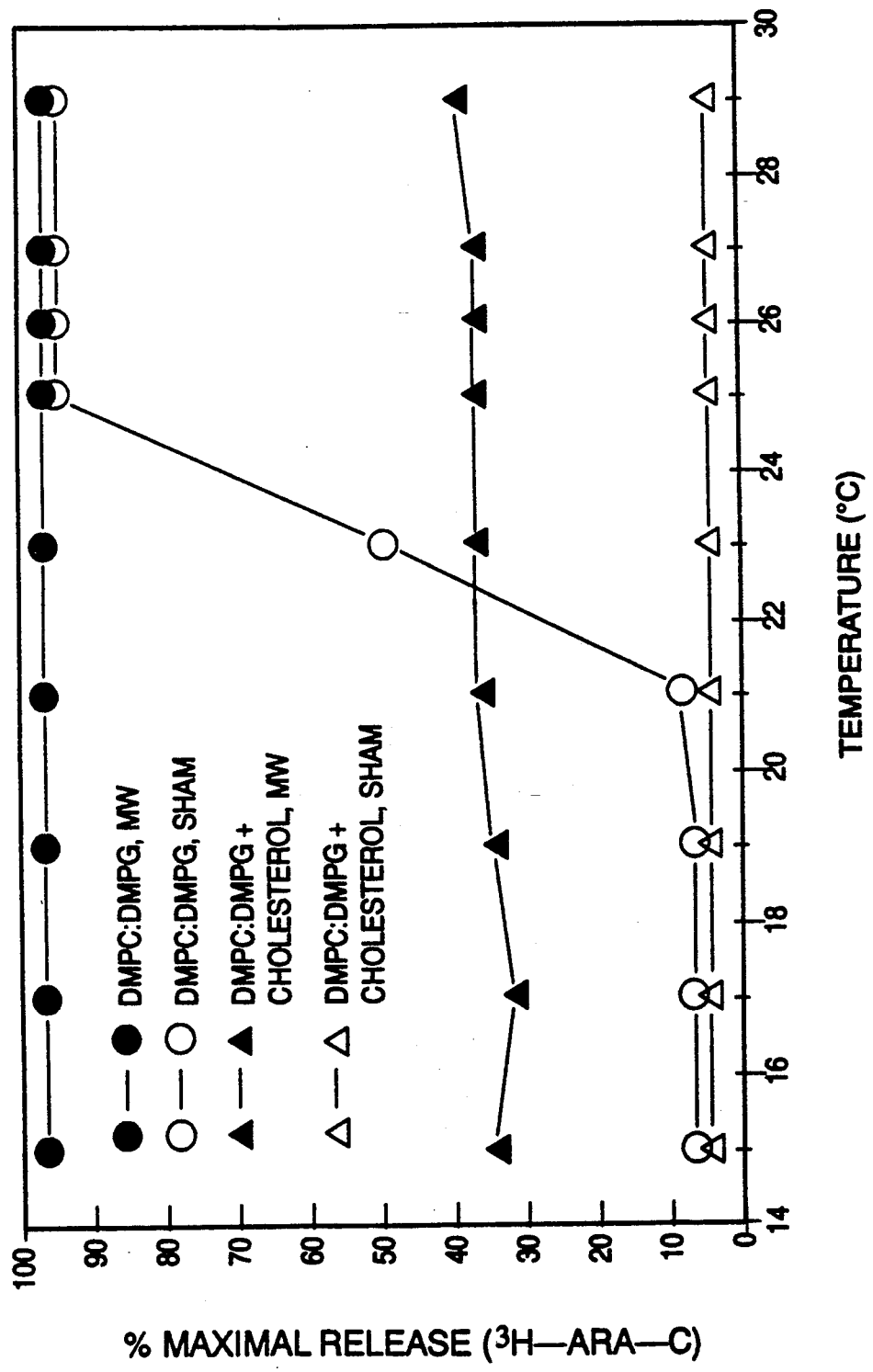
FIG. 22 shows the effect of microwave fields on drug release from phase transition and from nonphase transition DMPC:DMPG liposomes in plasma buffer.

An identical experiment to that depicted in FIG. 21 was performed except with liposomes maintained in buffered saline:human plasma (1:1). In FIG. 22 is shown the temperature dependence of drug release from DMPC:DMPG liposomes, unmodified or modified with cholesterol, during treatment with microwave fields. Unmodified phase transition liposomes display a Tc at approximately 23° C., while modified nonphase transition liposomes show no evidence of Tc at any temperature studied, as was the case in FIG. 21 Microwave fields in the presence of plasma triggered a marked increase in drug release from unmodified liposomes such that 100% release was observed a temperatures below Tc, and as low as 15° C. Thus, plasma significantly potentiated the microwave effect. This was also the case for nonphase transition liposomes, however, this effect was observed at all temperatures studied. For example, with liposomes in plasma the microwave fields resulted in nonphase transition liposomes experiencing an approximate 35-40% drug release compared to 3% in the presence of plasma alone, for all temperatures between 15°-31° C. Therefore, plasma significantly enhanced microwave-triggered drug release of nonphase transition liposomes below, at, and above the nominal Tc.

This last result is very important since it demonstrates that nonphase transition liposomes in the presence of plasma undergo microwave-triggered drug release over a wide temperature range (15°-29° C.). The change in drug release due to microwave treatment was represents an increase from about 3% to 35%-40%, which is a ten-fold increase.

Figure 23:
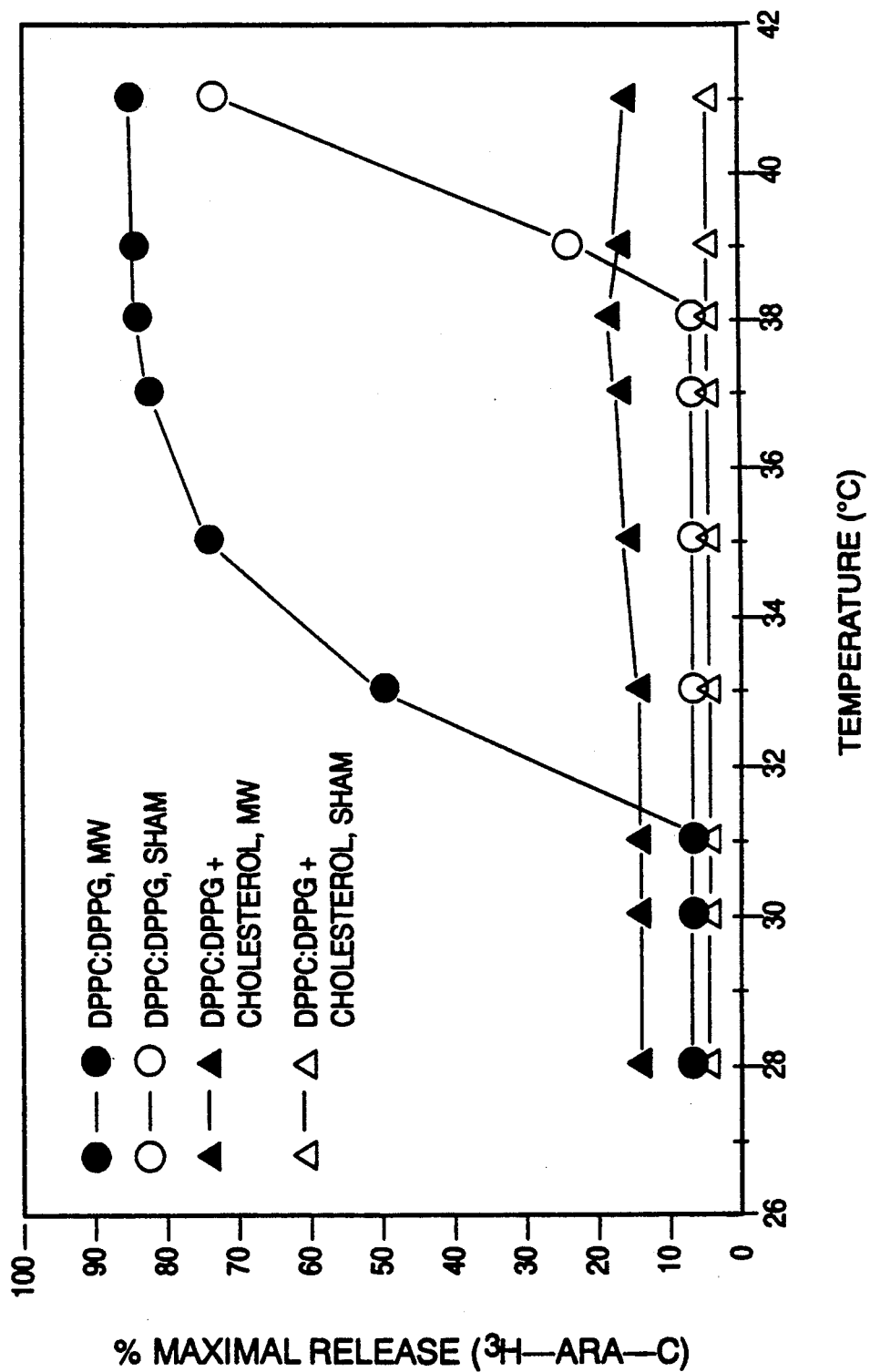
FIG. 23 depicts the effect of microwave fields on drug release from phase transition and from nonphase transition DPPC:DPPG liposomes in saline buffer.
Figure 24:
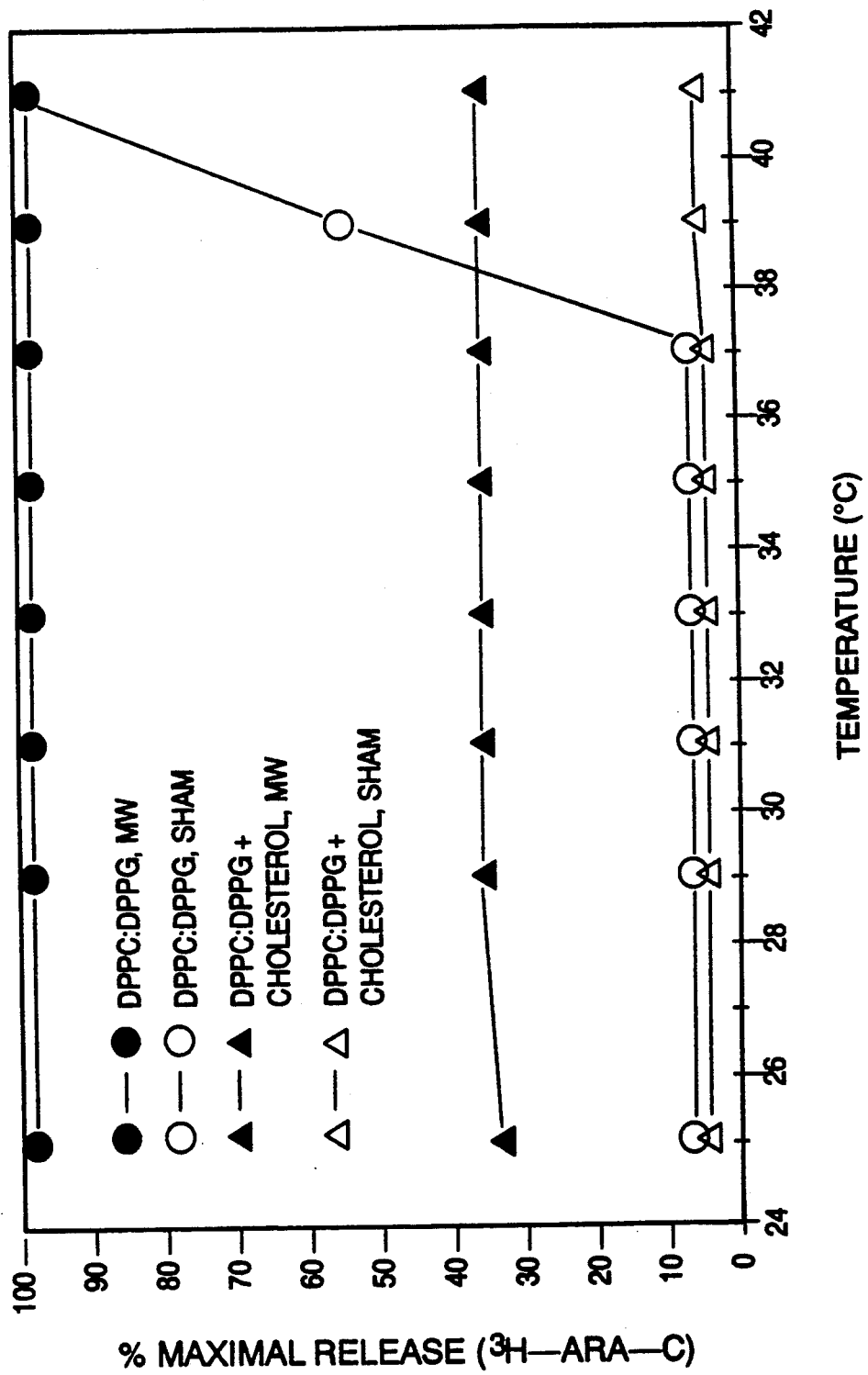
FIG. 24 illustrates the effect of microwave fields on drug release from phase transition and from nonphase transition DPPC:DPPG liposomes in plasma buffer.

Similar experiments were performed with DPPC:DPPG liposome systems which display a nominal Tc at about 40° C., as shown in FIG. 10. In FIG. 23 is depicted the temperature dependence of unmodified, phase transition DPPC:DPPG liposomes in buffered saline, and of cholesterol-modified nonphase transition DPPC:DPPG liposomes, with or without microwave field treatment. The results are qualitatively similar to those for the DMPC:DMPG liposome system shown in FIG. 21. For unmodified, phase transition liposomes microwaves triggered a significant increase in drug release at temperature below Tc. For cholesterol-modified liposomes, in contrast, microwaves triggered a significant increase in drug release at all temperatures studied, including temperatures below, at, and above the nominal Tc. FIG. 24 depicts results from a series of complimentary experiments in which the above liposome system was used in 50% human plasma. The data demonstrate that unmodified, phase transition DPPC:DPPG liposomes respond to microwave fields and experience significantly enhanced drug release at temperatures below Tc; the increase due to microwaves is from 5% to 100% between 25°-37° C. Cholesterol-modified, nonphase transition liposomes display spontaneous drug release in the absence of microwaves of about 5% over the entire temperature range of 25°-41° C.; they are stable in plasma, as was the case for the cholesterol-modified DMPC:DMPG liposomes shown in FIG. 22. In the presence of microwaves plus plasma these nonphase transition liposomes exhibited about a 35-40% drug release, compared to about a 5% in the absence of microwaves. Thus, an approximate 8-fold increase in drug release was triggered by the microwave field.

It is important to determine whether other drug markers are released from nonphase transition liposomes by microwave fields. To do this three different liposome systems were loaded with the cancer drug Doxorubicin (Trade name: Adriamycin-RFD, Adria Laboratories, Columbus, Ohio)). The following nonphase transition liposome systems were employed:

TABLE 2

| Liposome | Composition | Phase |
| --- | --- | --- |
| HPI:HPC:Chol:aT | 9:90.9:0.0:0.1 | Solid Phase |
| HPI:HPC:Chol | 6:62:32 | Solid Phase |
| EPG:EPC:Chol | 6:32:32 | Fluid Phase |

Figure 25:
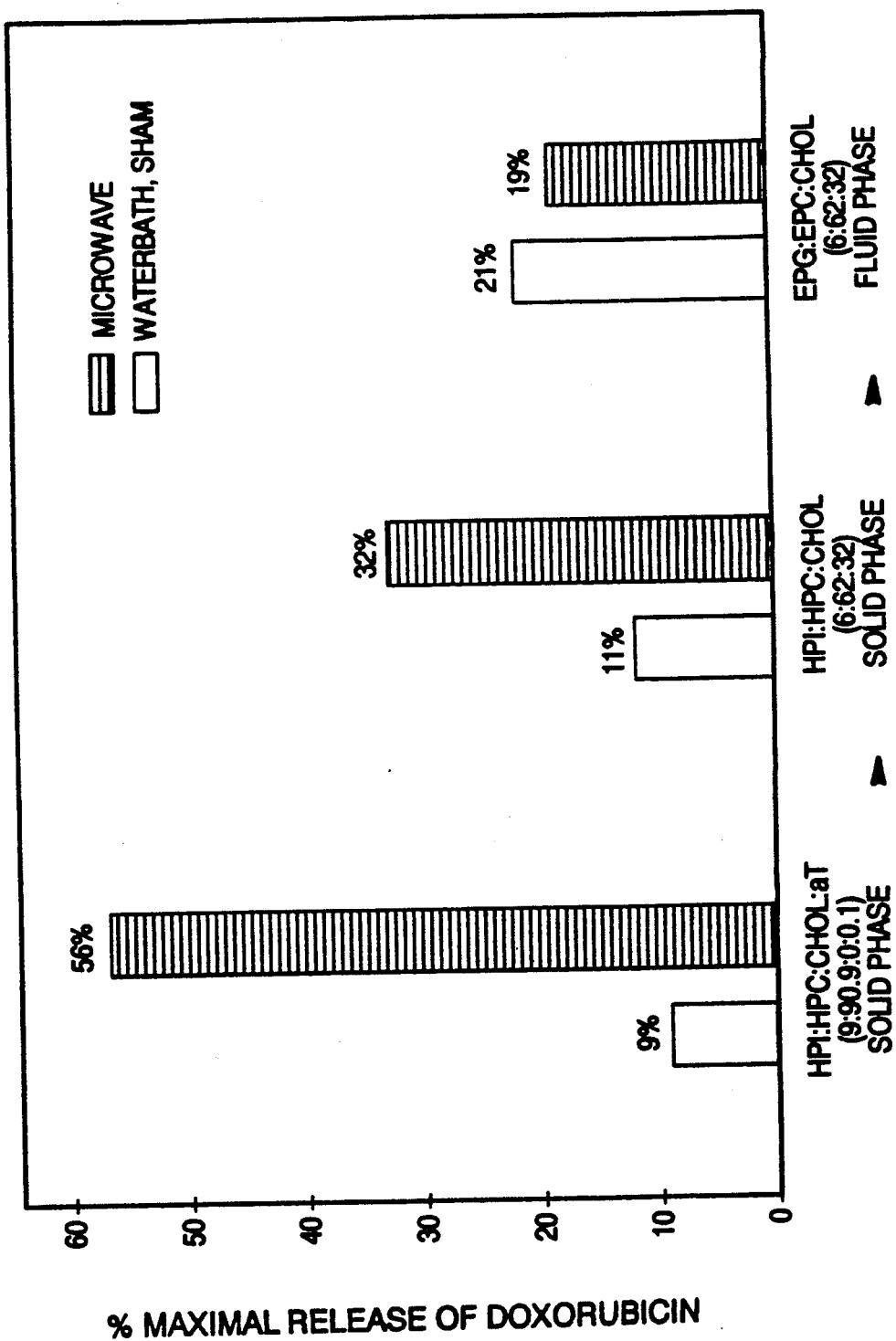
FIG. 25 shows the effect of microwave fields on three different nonphase transition liposome systems in plasma buffer.

FIG. 25 depicts the results from drug release studies using microwave fields at 6mW/gm, 15 minutes, 37° C. Both solid, nonphase transition liposomes experienced significantly enhanced Doxorubicin release in the presence of microwave fields plus plasma compared to plasma alone: HPI:HPC:Chol:aT vesicles showed a 5-fold increase; and HPI:HPC:Chol vesicles showed a 3-fold increase. In contrast, EPG:EPC:Chol fluid phase liposomes did not respond to the microwave field.

Taken together the above data indicate that
(1) Three different drug markers can be released from liposomes during treatment with nonionizing fields: cytosinearabinofuranoside, ARA-C; Doxorubicin; and 6-carboxyfluorescein, 6-CF. The two former compounds are widely used cancer drugs.
(2) The process of microwave-triggered drug release appears to be most effective for nonphase transition liposomes that are relatively solid, compared to those that are relatively fluid.
(3) The process of microwave-triggered drug release appears to be most effective for phase transition liposomes that are treated below Tc in the solid state.

Effects of Nonionizing Fields on Drug Release From Liposome Systems: MicroInjection of Drugs Using Liposomes Bound to Target Cells To demonstrate the process of microwave-triggered microinjection of drugs into target cells to which liposomes are bound a series of studies were conducted using:

TABLE 3

| Lipsome System/Net Charge | Phase/Nonphase Transition |
|---|---|
| DPPC:DPPG/− | Phase |
| DPPC:PE/+ | Phase |
| PC:PE/+ | Nonphase |

| Target Cells Employed (Net Negative Charge) |
|---|
| Erythrocyte Ghosts |
| Human Lymphocytes |
| Rat Macrophages |
| Tumor Cells Line: HLSQ-5 |

In these studies a liposome system was selected and interacted with a specific target cell so that the liposome would become electrostatically attached or bound to the surface of the target cell. The liposomes were each loaded with the fluorescent dye marker 6-carboxyfluorescein (6-CF) at concentrations that quenched fluorescence (>100 mM). The formed liposome-target cell complexes were then treated with microwave fields (6 mw/gm, at times and temperatures shown) to evaluate whether the treatment resulted in drug microinjection into the target cells. Since all liposomes contained 6-CF which was concentration quenched, and, thus, nonfluorescent, the release of 6-CF from these liposomes into the cells interior resulted in the dilution of 6-CF and the generation of fluorescence.

Liposome-Eyrthrocyte MicroInjection Studies

Figure 26:
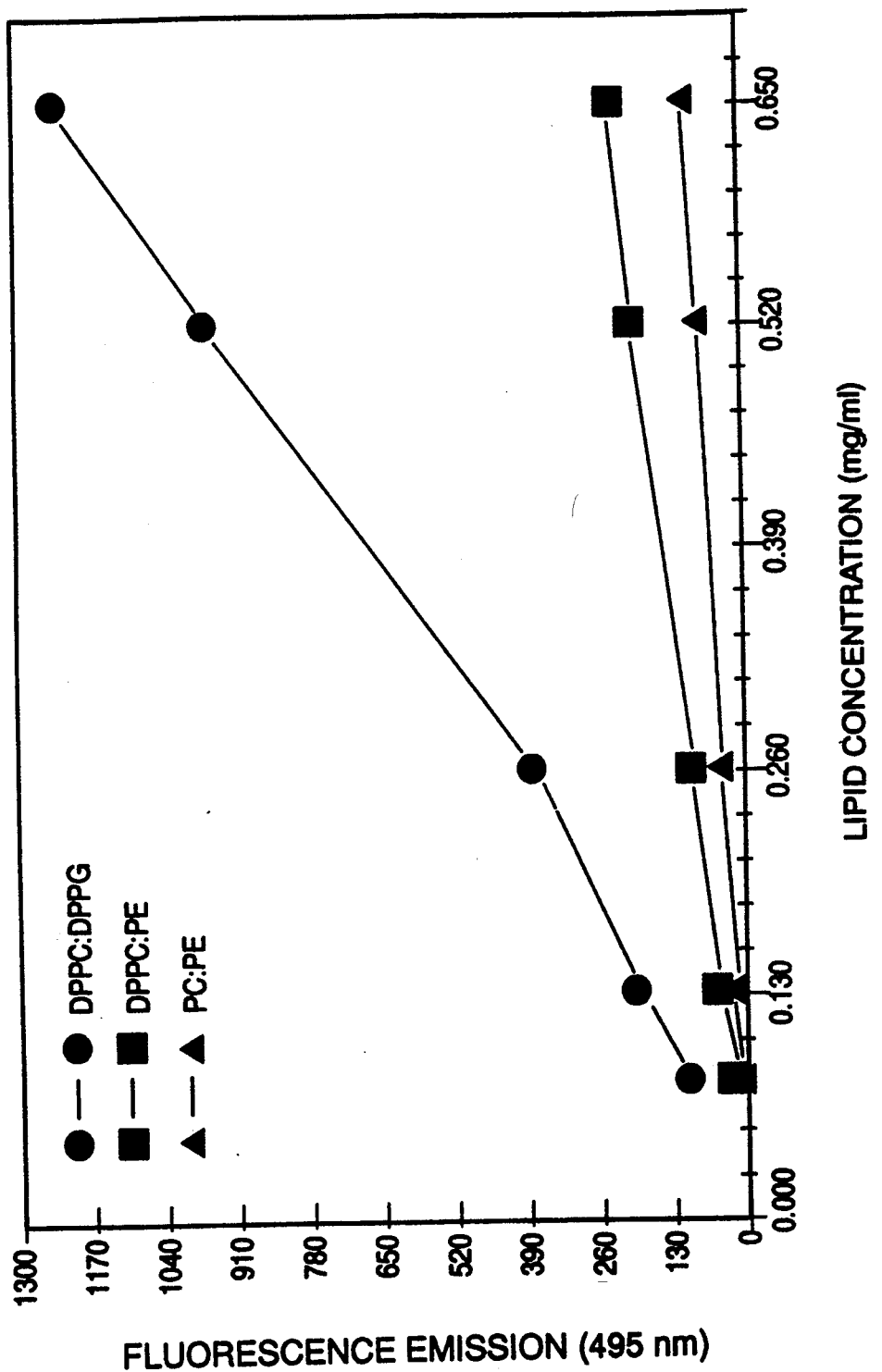
FIG. 26 demonstrates that liposome-human erythrocyte ghost complexes are formed using phase transition and nonphase transition liposome systems.
Figure 27:
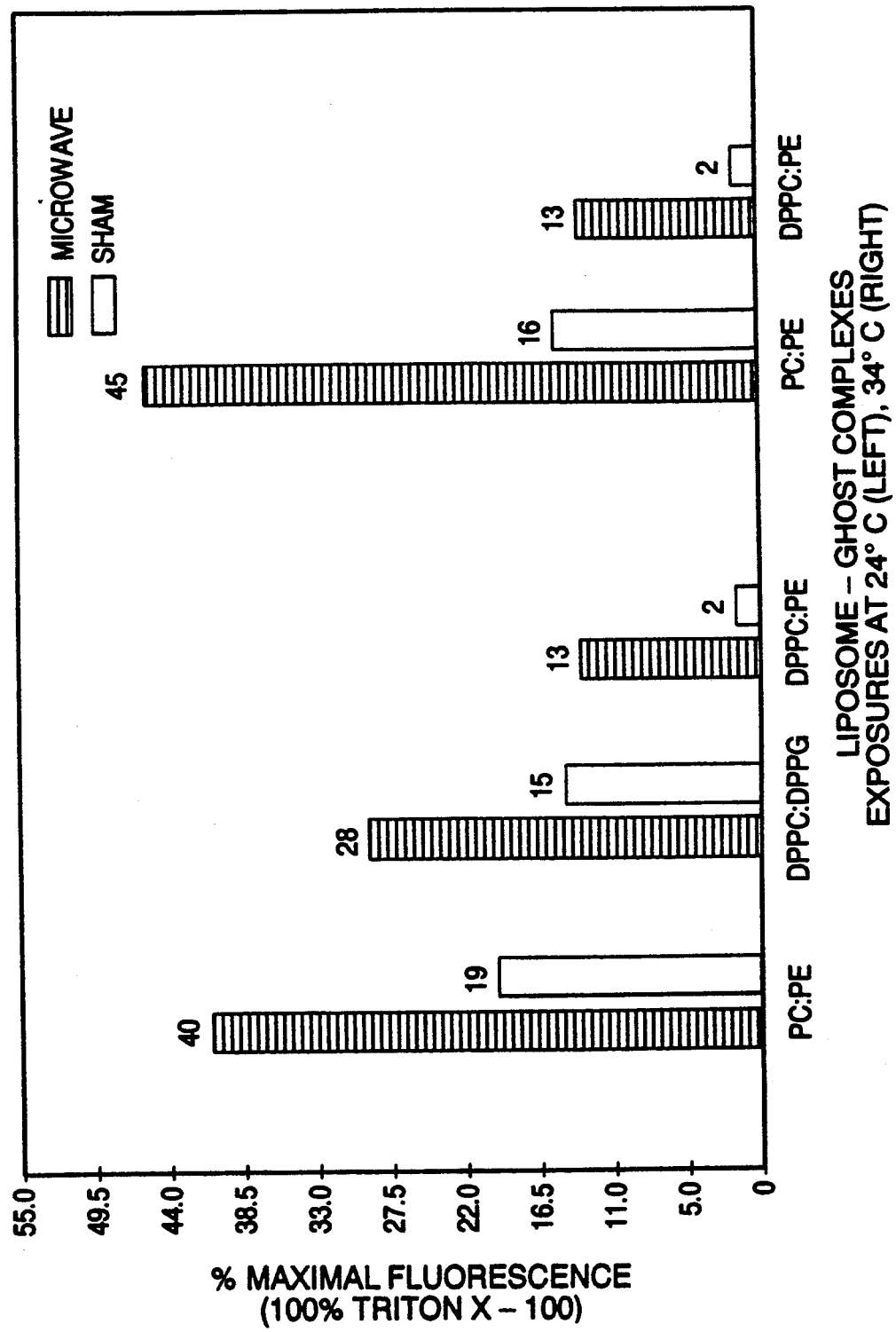
FIG. 27 illustrates microwave-triggered drug transfer for liposome-ghost complexes using phase transition and nonphase transition liposomes.

Human eyrthrocyte ghost cells were prepared and then interacted with each liposome system as described in the technical procedures section. FIG. 26 presents liposome binding data for the erythrocyte target cell. Each liposome tested achieved an attachment to the erythrocyte ghost as reflected in an increase in fluorescence of the complex formed as the concentration of added liposome (lipid) was increased. The negatively charged liposomes, DPPC:DPPG, yielded the greatest fluorescence signal, and each liposome system displayed a monotonically increasing binding curve. These complexes were used in microwave experiments shown in FIG. 27. When target-cell complexes were treated with microwaves for 15 minutes at 24° C. and at 34° C. 6-CF was transferred from the bound liposomes and entered the erythrocyte target cells to a significantly greater extent than for sham treatment at isothermal levels during waterbath treatment. For example, the nonphase transition liposome PC:PE resulted in an approximate 2-fold increase in dye microinjection over sham treatment at 24° C., and about a 3-fold increase over sham treatment at 34° C. These data demonstrate that microinjection with microwaves is effective with naturally occurring cell types such as the erythrocyte. Microinjection of fluorescent dye was also visually quantified by fluorescence microscopy of the liposome-target cell complexes and the results are given below. Results indicate that microwaves effectively facilitate microinjection of dye into target cells.

TABLE 4

Fluorescent Dye MicroInjection: Fluorescene Microscopy Data

| Treatment | Liposome:Erythrocyte Complex | % Fluorescence Cells |
|---|---|---|
| Microwaves | PC:PE | 48% |
| Isothermal Sham | PC:PE | 3% |
| Microwaves | DPPC:DPPG | 32% |
| Isothermal Sham | DPPC:DPPG | 2% |

Liposome:Lymphocyte MicroInjection Studies

It is important to demonstrate that liposome complexes can (1) form with lymphocytes, which are important cells responsible for immune defence against disease agents and are found in the circulatory system and throughout the body, and (2) that these complexes when treated with microwave fields result in direct microinjection of drug into this target cell.

Figure 28:
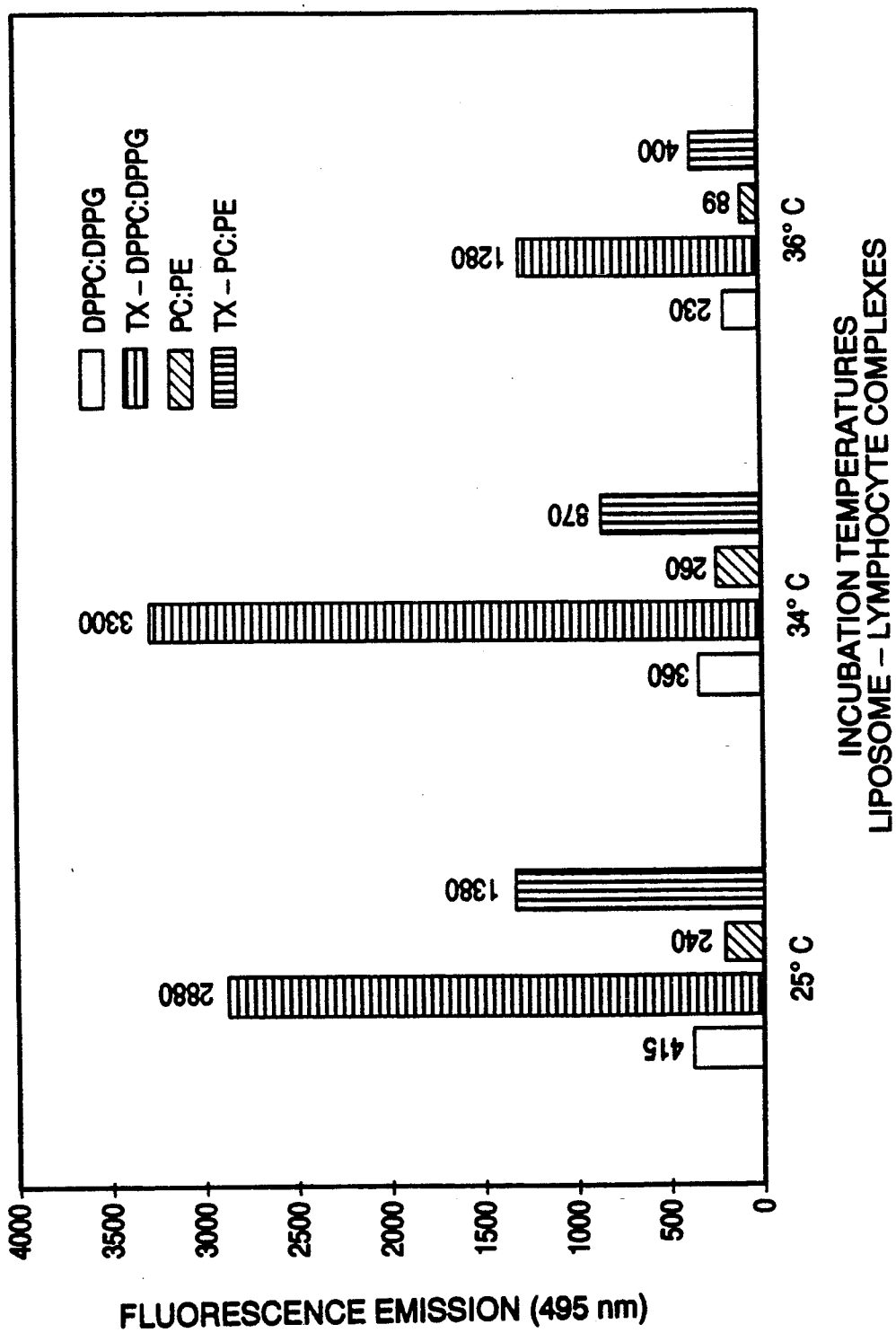
FIG. 28 illustrates that liposomes-lymphocyte complexes are formed using phase transition and nonphase transition liposomes.

Rat spleen lymphocytes and human peripheral blood lymphocytes were prepared as described below and used in studies with the phase transition liposome DPPC:DPPG and with the nonphase transition liposome PC:PE. FIG. 28 depicts data for binding of liposomes to lymphocytes at 25° C., 34° C., and at 36° C. In this presentation TX refers to treatment of the formed liposome-target cell complex with the agent Triton-X-100, which is a detergent and acts to release free dye from liposomes on the target cell. This value, e.g. TX-DPPC:DPPG, represents dye associated with liposomes that have been complexed with the target cells. The value for liposomes alone, e.g. DPPC:DPPG, represents background fluorescence of the liposome-lymphocytes complex before treatment with TX; liposomes were loaded with 6-CF at concentration quenching levels, as discussed above. Therefore, a significant increase in dye signal after treatment of the liposome-lymphocyte complex with TX is indicative of bound liposomes. The data indicate that liposome-lymphocyte complexes are formed at each temperature studied for each of the liposomes tested. For example, at 25° C. nonphase transition liposomes PC:PE complexed to lymphocytes had about 240 units of fluorescence before treatment with TX, and after TX they yielded a value of 1380. Thus, a significant amount of dye was associated with the liposome-lymphocyte complex that was trapped inside of liposomes attached to the lymphocyte cell surface.

Figure 29:
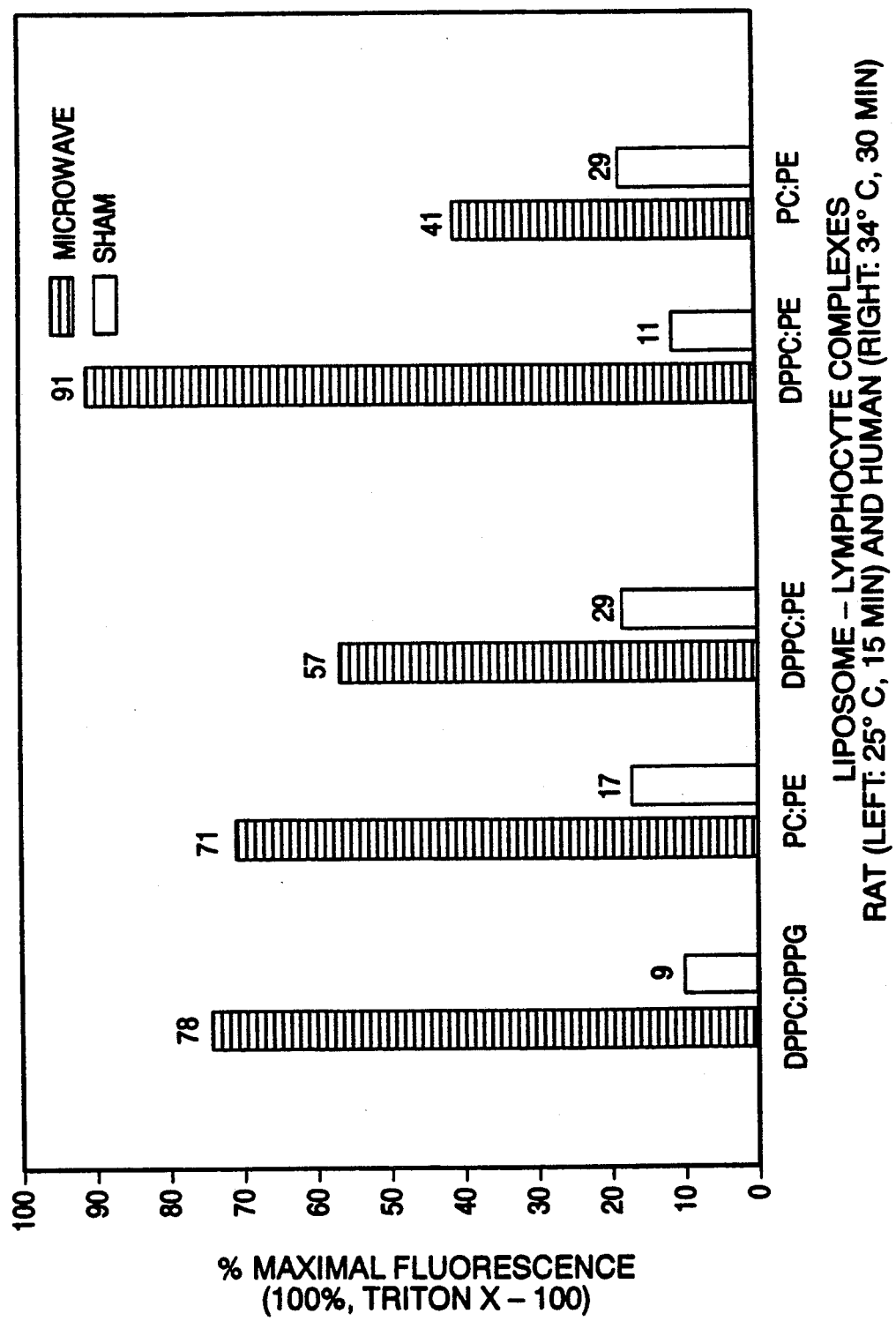
FIG. 29 shows microwave-triggered drug transfer for liposome-lymphocyte complexes using phase transition and nonphase transition liposomes.

These liposome-target cell complexes were tested for microwave-triggered drug microinjection using human or rat lymphocytes at 25° C. or at 34° C., respectively (FIG. 29). Microwave treatment resulted in a significant increase in dye microinjection into target lymphocytes. For example, at 25° C. with the nonphase transition liposomes PC:PE microwave treatment of lymphocyte complexes resulted in over a 4-fold level of microinjection of dye compared to the isothermal, sham-exposure treatment. Visual quantitation by fluorescence microscopy was also performed and the results with DPPC:DPPG are presented below.

TABLE 5

Fluorescent Dye MicroInjection: Fluorescene Microscopy Data

| Treatment | Liposome:Erythrocyte Complex | % Fluorescence Cells |
|---|---|---|
| Microwaves(34° C.) | DPPC:DPPG | 53.0% |
| Isothermal Sham(34° C.) | DPPC:DPPG | 5.0% |

TABLE 5-continued

Fluorescent Dye MicroInjection:
Fluorescene Microscopy Data

| Treatment | Liposome:Erythrocyte Complex | % Fluorescence Cells |
|---|---|---|
| Microwaves(36° C.) | DPPC:DPPG | 60.0% |
| Isothermal Sham(36° C.) | DPPC:DPPG | 7.5% |

Liposome:Macrophage MicroInjection Studies

Macrophages represent an important class of cells found in the body. They are responsible for removing particulates and foreign agents from the body by phagocytosis. This specialized process involves engulfing the foreign entity and digesting its contents to neutralize the entity. Thus, the macrophage will permit the liposome vesicle to bind at its surface which it will then phagocytose over time. The internalized liposomes can then be treated with microwaves to release the drug into the macrophage cytoplasm where it has pharmacological activity. Without treatment with microwaves, or any other triggering modality to release the liposomal drug, the liposomes would be sequestered into lysozymal compartments and degraded by acid and enzymes to neutralize the drug.

Figure 30:
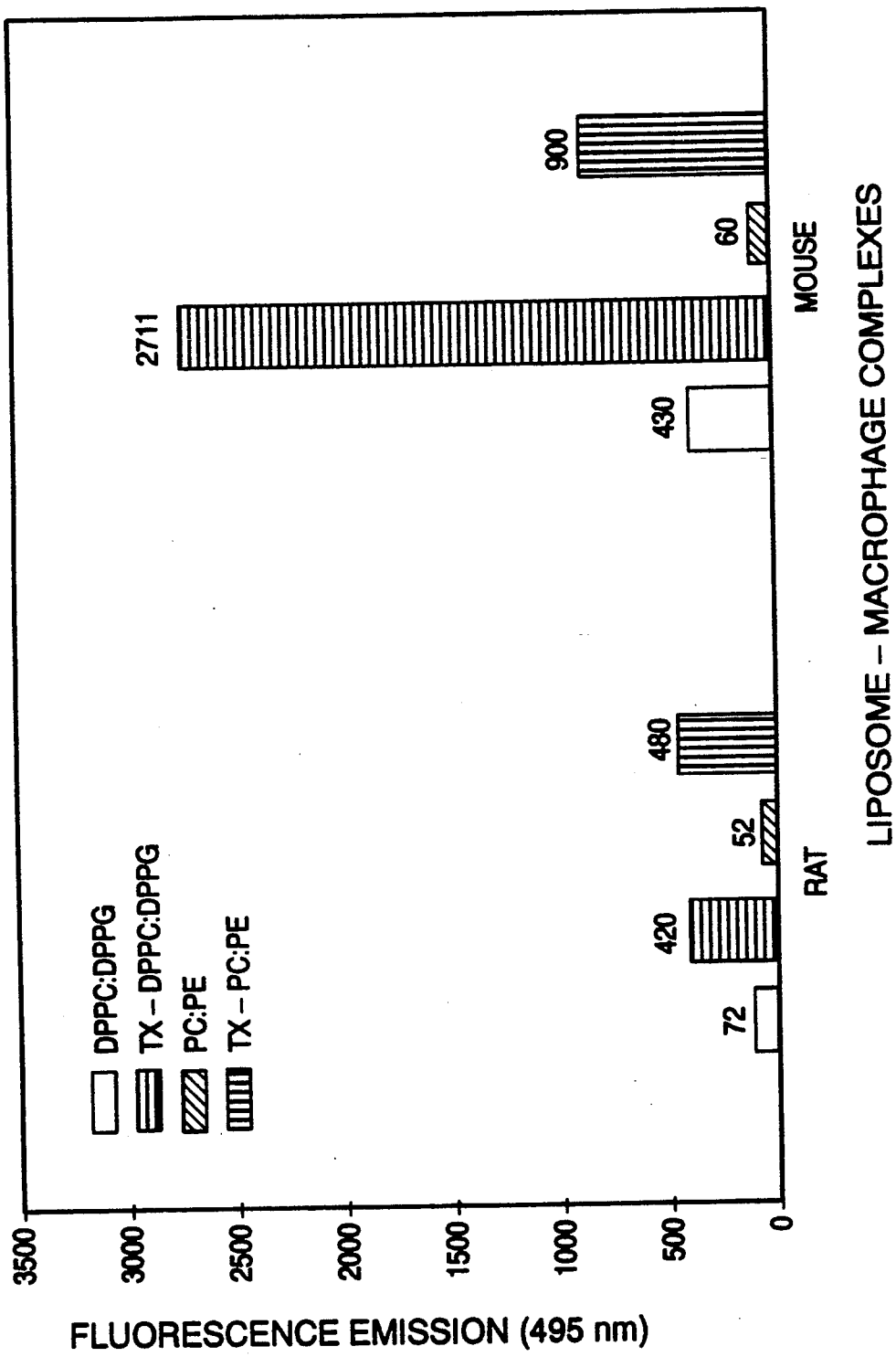
FIG. 30 illustrates that liposome-macrophage complexes are formed using phase transition and nonphase transition liposomes.

For these experiments rat and mouse peritoneal were prepared and harvested as described below and used in these studies FIG. 30 presents evidence for both phase transition (DPPC:DPPG) and nonphase transition (PC:PE) liposomes binding to macrophages. These measurements were carried out as described for lymphocytes in FIG. 28. Both liposome systems displayed significant binding to rat and to mouse macrophages. For example, nonphase transition PC:PE liposomes exhibited a 9.2-fold increase in 6-CF fluorescence after treatment with TX for rat macrophages, and a 15-fold increase for mouse macrophages. This indicates significant liposomal dye bound to the macrophage cell surface.

Figure 31:
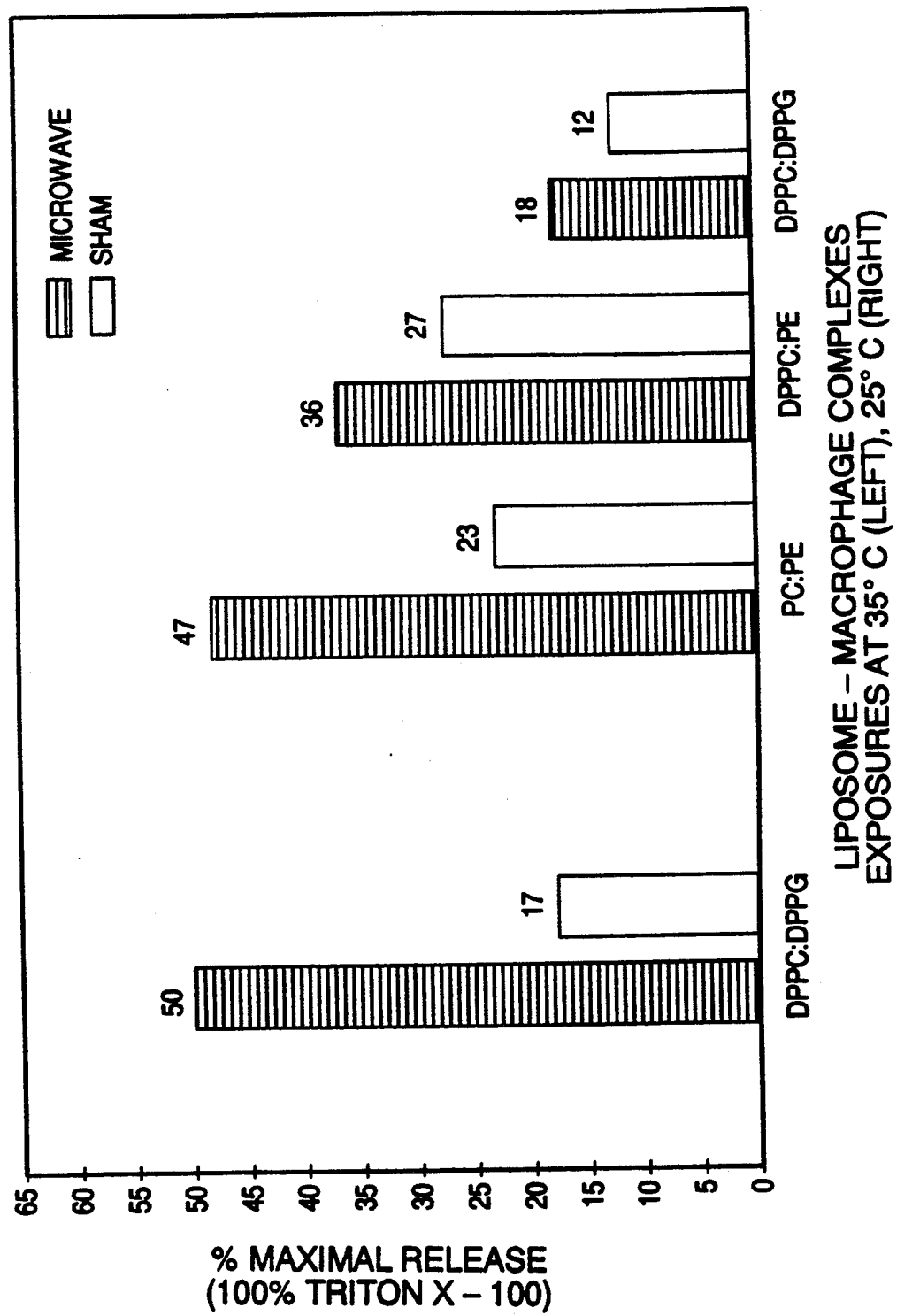
FIG. 31 depicts microwave-triggered drug transfer for liposome-macrophage complexes using phase transition and nonphase transition liposomes.

These liposome-macrophage complexes were then tested for microinjection of dye by microwaves and these data are shown in FIG. 31. Microwave exposures were carried out at 35° C. and at 25° C. The findings demonstrate that microwaves can trigger dye microinjection using both phase transition (DPPC:DPPG) and nonphase transition (PC:PE) liposomes. At 25° C., where both liposome types were employed, we see that the nonphase transition liposome PC:PE was most effective in drug microinjection since they gave a 104% increase over isothermal, sham treatment in a waterbath, compared to that for DPPC:DPPG liposomes (50% increase) and DPPC:PE liposomes (33% increase).

Liposome-Tumor Cell MicroInjection Studies

Figure 32:
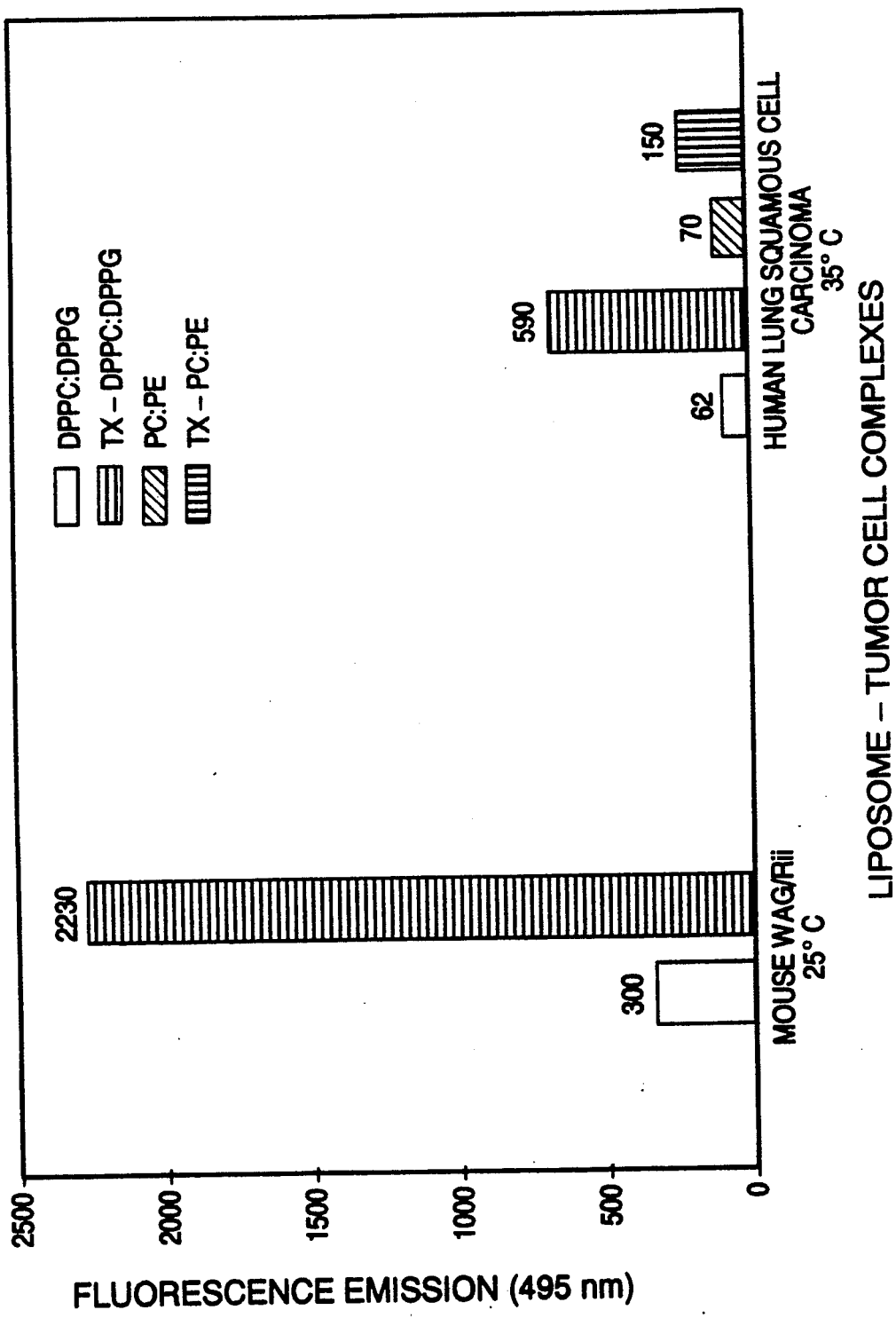
FIG. 32 provides evidence for formation of liposomes-tumor cell complexes using phase transition and nonphase transition liposomes.
Figure 33:
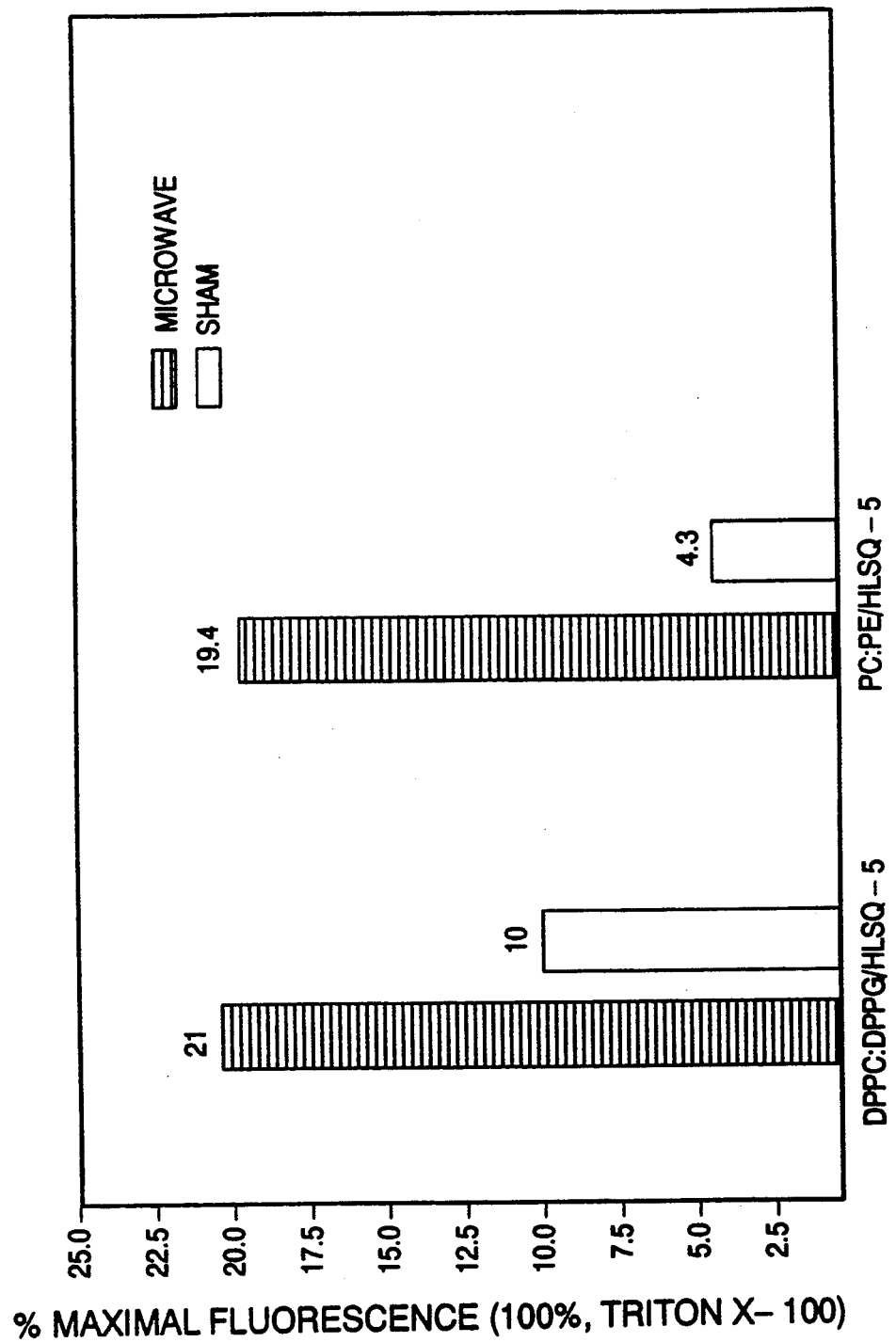
FIG. 33 shows microwave-triggered drug transfer for liposome-tumor cell complexes using phase transition and nonphase transition liposomes.

Tumor cells represent another important class of cell types to demonstrate liposome drug microinjection via microwaves. Two representative tumor cell lines were tested, one from a human source, a human lung squamous cell carcinoma, HLSQ-5, and the other from a mouse source, WAG/Rij. FIG. 32 shows data demonstrating liposome binding to each tumor cell line, using the approach discussed for FIG. 28. Studies were also undertaken to determine how effective microwave fields would be in triggering dye microinjection into the human tumor cell line using both phase transition and nonphase transition liposomes In these studies microwaves were employed at 35° C. for 30 minutes. FIG. 33 presents this data and dye transfer into tumor cell complexes is expressed as percent maximal fluorescence released from an untreated complex using the detergent Triton-X-100 (TX), as in FIGS. 27-31 Microwave fields resulted in a 2-fold increase in dye transfer into tumor cell complexes with DPPC:DPPG, a phase transition liposome. However, microwaves resulted in a 4.5-fold increase of dye into tumor complexes formed using the nonphase transition liposomes PC:PE. Under these conditions the nonphase transition liposome was more effective in facilitating drug microinjection triggered by microwaves.

Fluorescent microscopy measurements were made on the tumor cell complexes discussed in FIG. 33. The results of these measurements are given below.

TABLE 6

Fluorescent Dye MicroInjection:
Fluorescene Microscopy Data

| Treatment | Liposome:Tumor Cell Complex | % Fluorescence Cells |
|---|---|---|
| Microwaves(35° C.) | DPPC:DPPG | 19.4% |
| Isothermal Sham(35° C.) | DPPC:DPPG | 4.3% |
| Microwaves(35° C.) | PC:PE | 30.0% |
| Isothermal Sham(35° C.) | PC:PE | 2.5% |

In Vivo Experimental Studies

Effects of Nonionizing Fields on Drug Release From Liposomes: 2450 MHz Studies

To evaluate the efficacy of in vivo microwave-triggered drug release from liposomes several experiments were performed. The nonphase transition liposome system EPC:DPPG:aT (90:9.9:0.1) was chosen as a representative liposome system for use in these studies since we have previously shown that such nonphase transition liposomes are stable and insensitive to temperature changes with regard to drug release, and that they respond to microwave fields (TABLE 1, FIG. 20). These liposomes were loaded with Gentamicin at approximately 240 mg/ml distilled water in the aqueous phase during vesicle preparation; this yielded about 25 mg of Gentamicin, and about 0.300 mg total lipid, per ml of final liposome solution.

Demonstration of in vivo microwave-triggered drug release from liposomes involved placement of a liposome depot into a subcutaneous or intramuscular site in the animal. Sites were located in the shoulder or in the flank of the rear leg of rats; multiple sites could therefore be placed in such locations in the animal. The liposome depot was generally formed by injecting into the site approximately 0.75 ml of liposome solution, as described above, which was maintained as a physically discrete entity for at least 4 weeks. This was validated by surgically removing and inspecting several liposome depots at various times postimplantation. The spontaneous release of the drug Gentamicin from an implanted liposome depot was presented in FIG. 6 and clearance of free, unbound Gentamicin takes approximately 24 hours. Thus, liposome depots were implanted into animals 24 hours prior to performing microwave drug delivery experiments.

A typical experiment involved anesthetizing the animal, surgically catheterizing the femoral artery or the carotid artery, and stabilizing the animal such that a respiratory rate was established at 60-80 bpm and core temperature maintained at 35°-37° C. Animals were placed on a heating pad and kept under infrared lamps to assist in animal thermoregulation. Blood samples were drawn at ten minute intervals before microwave treatments to establish baseline Gentamicin levels; all blood samples were 0.30 ml and this volume was replaced with isotonic saline immediately after withdrawing blood. Blood samples were immediately spun to determine the animal's hematocrit and the plasma was collected for processing in a commercially available Gentamicin RIA assay kit (e.g., Dupont RIA Kit A075).

Microwave treatments were administered using a contact applicator (ELMED Corp., Addison, Ill.; model 3013) or similar commercial device for focusing the microwave field at the site of the liposome depot. The local specific absorption dose (SAR) was approximately 4–6 mW/gm and the animal's core temperature was continually monitored before, during, and after exposures. The SAR levels used in these studies did not elevate the animal's core temperature; in addition, the temperature of the local site of microwave application did not increase by more than 1 degree centigrade for these SAR levels. Temperature was monitored using a microwave compatible temperature probe that employs a high resistance carbon-impregnated nylon cable and a thermistor bead sensor (Vitek-type Electrothermia Monitor, BSD Corp., Salt Lake City, Utah).

Figure 34:
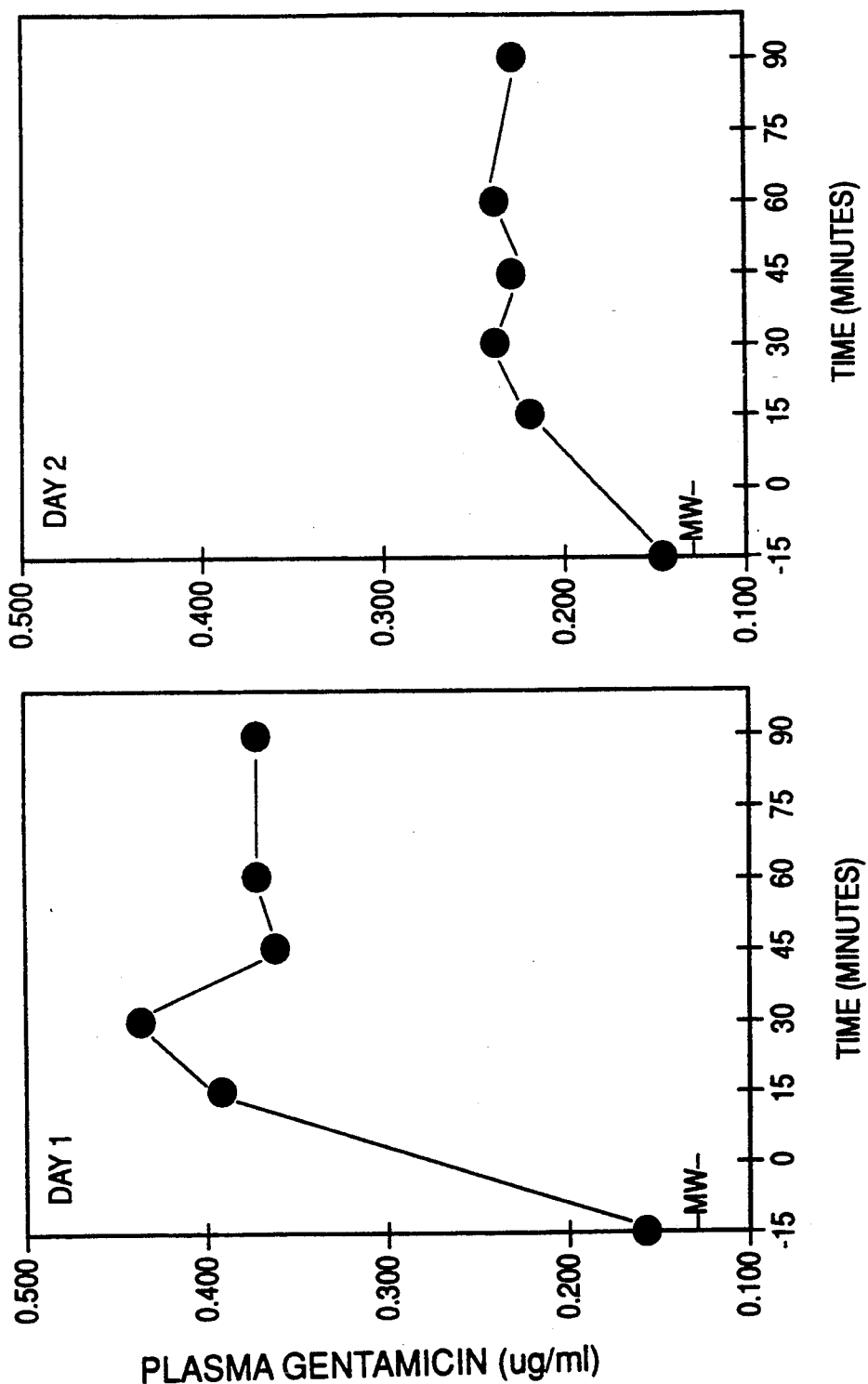
FIG. 34 depicts microwave-triggered drug release from an in vivo liposome depot placed in a rat. The study demonstrates that multiple treatment of the liposome depot on Day 1 and on Day 2 with microwave fields triggers the controlled, on-demand release of Gentamicin into the circulation.
Figure 11:
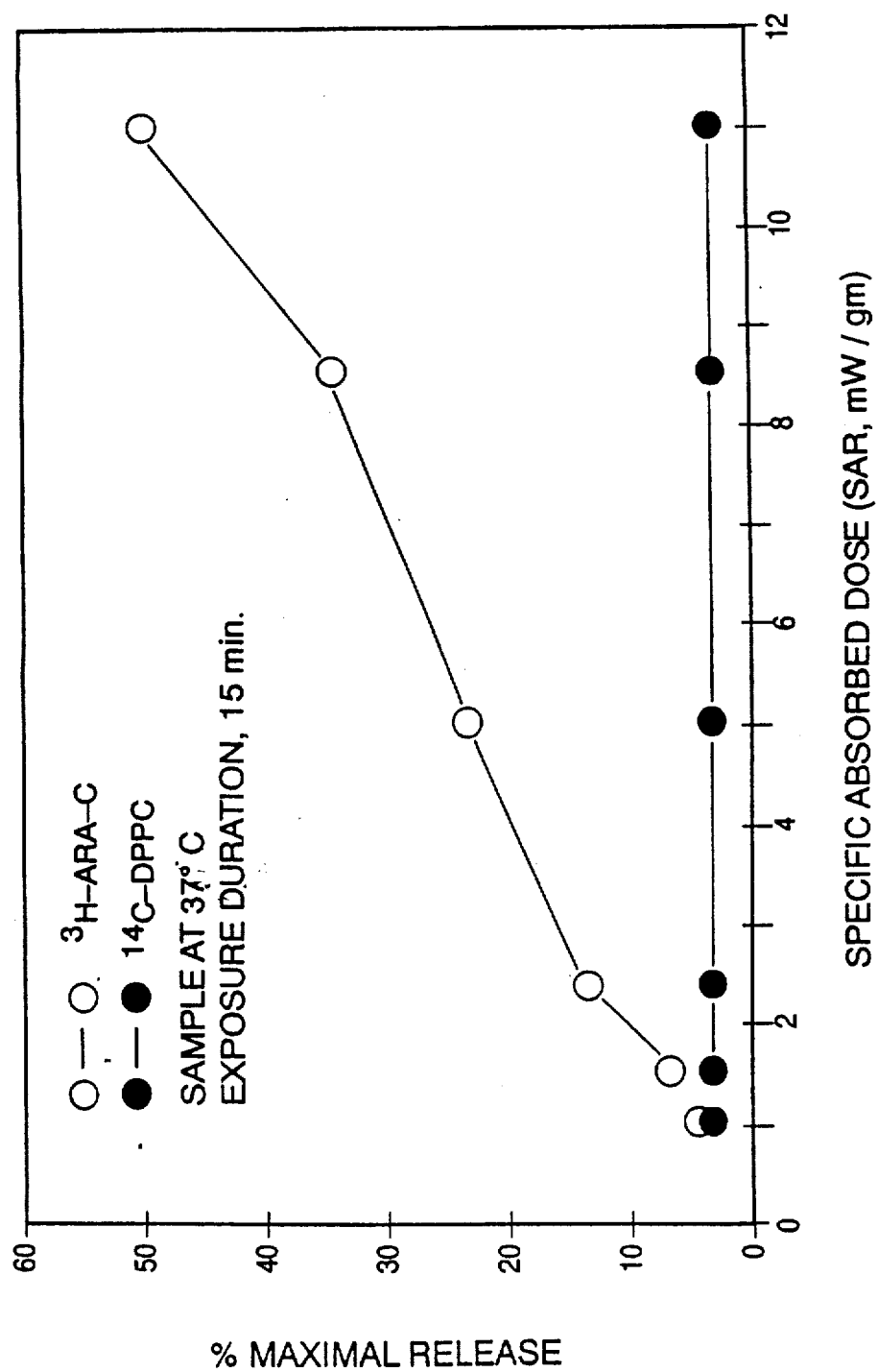
Figure 13:
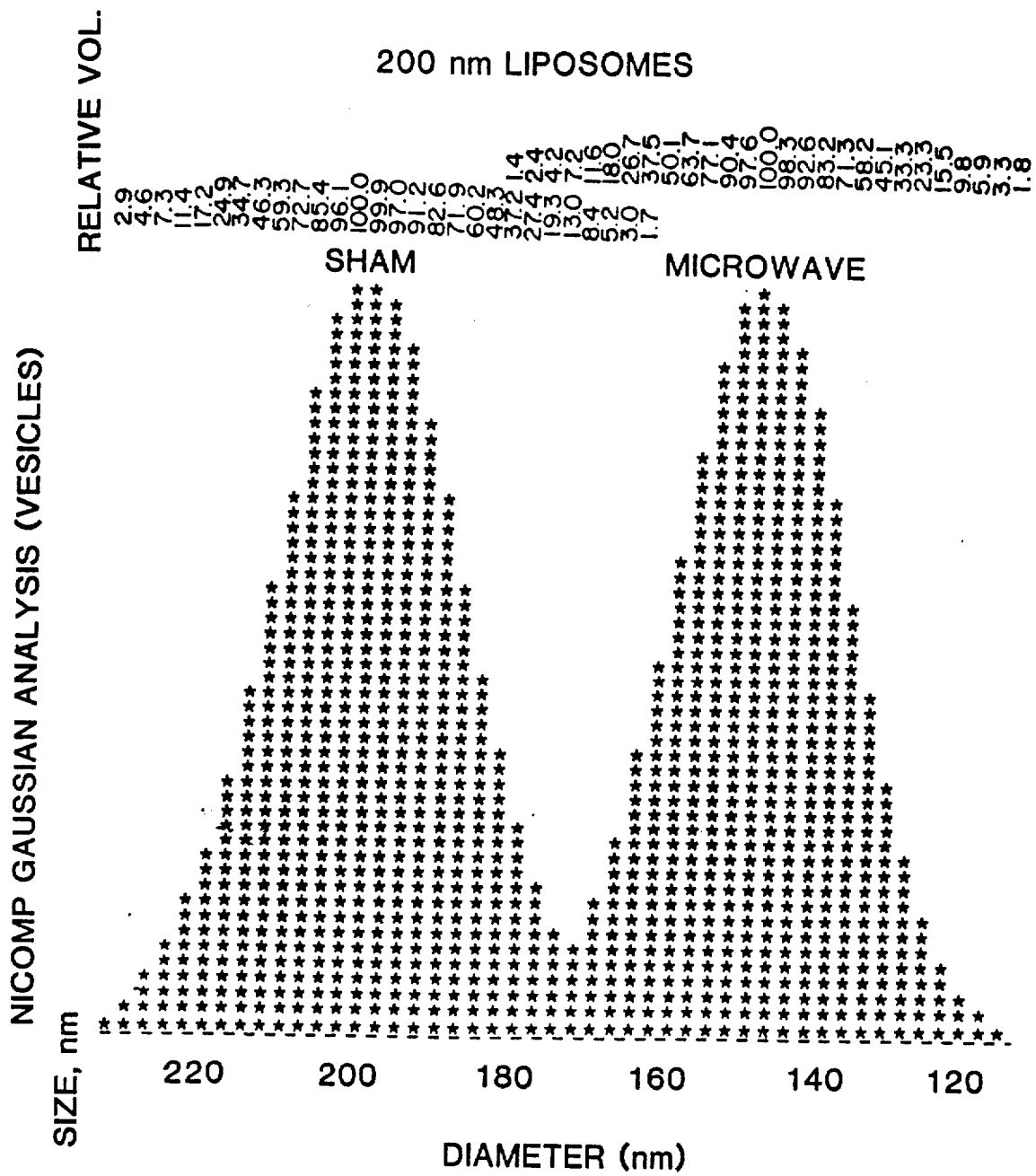

The results of a typical in vivo drug release experiment is depicted in FIG. 34. In this study the rat received a liposome depot on Day 0 and 24 hours later on Day 1 a localized microwave treatment at the liposome depot was administered for 15 minutes. Before microwave treatment the animal possessed a plasma level of Gentamicin of approximately 0.5 ug/ml, which is consistent with FIG. 6. Microwave treatment at the liposome depot site commenced for 15 minutes, and, after a 15 minute period, the first plasma sample collected gave a Gentamicin level of approximately 0.4 ug/ml. This represents a 2.7-fold increase in Gentamicin concentration in the circulation. At times up to 90 minutes post-treatment this level did not change. Thus, a single microwave treatment resulted in a significant elevation of Gentamicin for a period of at least 90 minutes. The same animal was investigated on Day 2 and before microwave treatment the plasma level had dropped to a baseline value of approximately 0.125 ug/ml, which is slightly less than on Day 1. An identical microwave treatment was administered and plasma levels were observed to follow the same kinetics of increase: a maximal increase within 15 minutes postexposure that was sustained for at least a 90 minute period.

The above results demonstrate that microwaves are effective in releasing drugs from liposome vesicles in vivo, and that multiple exposures can be used as a treatment modality for delivering Gentamicin into the blood stream.

During actual "human-use" of the technique of the present invention, liposomes loaded with a drug could be otherwise injected or otherwise administered directly into the blood stream, to the muscle, skin, lungs, eye, etc. of an individual. Similarly, liposomes may be injected into tumors, growths, glands, etc. and the release therein effected by the electromagnetic field radiation. Once administered to the specific target site area of the human body to be treated, the liposomes loaded with drug become a drug depot which when exposed to an electromagnetic field releases the drug to and only to the specific area in need of treatment. The device utilized with human beings could be the same or different from the generating devices 20 and 50 depicted in FIGS. 7, 7A and FIG. 8 of the drawings. Although the same devices 20 and 50 could be utilized, it is foreseen that a small conventionally available radiating antenna would be used to focus the radiation to a particular area of the human body. Notwithstanding, it is to be understood that all devices suitable for generating electromagnetic fields of the intensity as disclosed herein, is covered by this invention. These include but are not limited to those which are ambulatory, suitable for carrying attached to the body of the patient or non-ambulatory type wherein the patient will go to the hospital or physician's office at times when the release of the drug is needed or indicated. Examples of such treatments would be daily release of insulin in treatment of diabetes, periodic release of antihypertensives, chemotherapeutics, nutrition agents, vitamins, diagnostic agents and such others.

The invention is also shown by the following examples.

TECHNICAL PROCEDURES

A. DETERMINATION OF DYE RELEASE: PHOTOMICROSCOPE AND SPECTROFLUOROMETRIC ASSAYS

Photomicroscopy was performed on liposome-cell complexes to visually assess 6-CF transfer into target cells. A Zeiss system was employed consisting of a Model-16 laboratory microscope with phase-contrast optics, epifluorescence illumination, and a MC-63 photomicrographic camera system. Quantitative measurement of fluorescence was carried out using a Perkin-Elmer Luminescence Spectrometer LS-5B or a Kratos Fluorescence Monitor Model 983, which was equipped with a fluorescein excitation filter (550 nm cutoff), and was operated at an emission wavelength of 495 nm. Measurements are carried out at 4° C.

Dye release from liposome vesicles and from liposome-target cell complexes was performed in several ways. Quantitating release of 6-CF and release of Gentamicin from a liposomal vesicle suspension involved pelleting the liposomes by ultracentrifugation at 180,000×g using a Beckman Airfuge for 60 seconds, and by measuring the 6-CF fluorescence of the supernatant, or by assaying the Gentamicin present in the supernatant by using a commercially available RIA kit (Dupont RIA Kit A075). Liposomes that were loaded with Doxorubicin were assayed for drug release by passing the liposomes suspension over a cation exchange column, such as Dowex-50W-X4, to remove free Doxorubicin released from the liposomes. The liposomes, which pass through the column, are collected, lysed by using ethanol-tertiary butanol, and Doxorubicin fluorescence measured. By comparing this value to that for untreated liposomes the amount Doxorubicin released was calculated.

All of the liposome-cell complexes were formed with liposomes that were loaded with 6-CF. These complexes were assayed for dye microinjection into the target cell by first pelleted the complex at 12,000×g for 10 seconds in an Eppendorf centrifuge, and the resultant supernatant was collected for fluorescence measurement. The liposome-cell pellet was then washed twice by pelleting at 12,000×g at 4° C., and the final suspension was assessed for fluorescence by photomicroscopy and spectrofluorometry.

B. TARGET CELL POPULATIONS

A variety of human and rodent cell types were employed. Human erythrocytes and lymphocytes were isolated from the blood of healthy male donors on the day of venipuncture. Erythrocyte ghost preparations were carried out according to the standard Dodge protocol and the cells were used over a four day period. Lymphocytes were isolated from the buffy coat by centrifugation through Histopaque (Sigma Chem. Co.) and then washed thoroughly in buffered saline.

Sprague-Dawley rat spleens were the source of rat lymphocytes: cells were teased into buffered saline at 4° C., and are purified over Ficoll-Hypaque by centrifugation.

Human lung squamous carcinoma cells (HLSQ-5) were used immediately following cell culture harvesting in exponential growth phase.

Rat and mouse peritoneal macrophages were harvested under sterile conditions from adult male Sprague Dawley rats or similar Balb/c mice on day four after i.p. injection of 10 ml of sterile mineral oil. Macrophages were purified by plating the peritoneal cell population on plastic dishes at 37° C. for 90 minutes and discarding non-adherent cells. Cell populations were used at greater than 90% viability as determined by nigrosin dye exclusion.

Tumor cell lines were obtained from human and mouse sources. The human lung squamous cell carcinoma, HLSQ/-5, was kindly provided by Dr. Elinore Blakely of the Lawrence Berkeley Laboratory, UC Berkeley, Calif. The mouse tumor cell line, WAG/Rij, was kindly provided by Dr. Thomas Tenforde of the same institution. The growth characteristics and properties of each cell line has been carefully described by each of these investigators, respectively.

C. LIPOSOME-TARGET CELL BINDING

Liposomes were interacted with cells in buffered saline at 25° C. (20° C. for DMPC liposomes) for 30 minutes with gentle shaking, except for macrophage populations which were plated on plastic dishes and were incubated with liposomes for 12 hours to promote phagocytosis. Liposomes were used at ~1.5 mg phospholipid/ml per cell populations at about $10^7$–$10^8$ cells/ml. After incubation for 1 hr at 37° C. the liposome-cell reaction mixtures were centrifuged using an Epplendorf centrifuge for 1 minute at 12,000×g, and resuspended, in buffered saline, both repeated five times, in order to remove free unbound liposomes from the suspension. Remaining liposome-macrophage complexes were not removed by washing and centrifugation, but were allowed to adhere to the plastic. After standing for 1 hour at 37° C., dye release was induced by bringing liposome-target cell complexes to 42° C. and then adding 1% (v/v) detergent (Triton X-100).

EXAMPLE 1

General Procedures for Microwave and Sham Exposures In Vitro

Microwave (2450 MHz, CW) exposures in vitro were conducted in a tunable waveguide device, as shown in FIGS. 7–7A, described above and were capable of continuous sample temperature measurement, continuous sample mixing, pO2 conditioning, on-line forward and reflected power monitoring, and temperature control of the exposure compartment by a circulating, nonabsorbent dielectric fluid. Immediately following field or sham treatment the liposome-target cell samples were centrifuged at 12,000×g and resuspended twice, with the final pellet and first supernatant saved for fluorescence analysis.

The liposome sample to be exposed to electromagnetic field irradiation was placed in a non-absorbing, three-piece Teflon exposure compartment depicted in FIG. 7A. The Teflon sample cell (0.5 cm, o.d.) A, (FIG. 7A) was loaded with 1 ml of the suspension and placed into the Teflon baffle insert which was positioned in the Teflon waveguide insert (B, C; FIG. 7A). The Teflon waveguide insert is placed in the center of the waveguide section with the sample cell parallel to the short dimension of the waveguide, and thus was parallel to the electric field vector. This configuration resulted in the sample being positioned in the middle third of the waveguide to ensure uniform incident electric field intensity.

The sample cell had a SILASTIC gas line (0.1 mm, o.d.) and a VITEK-type Electrothermia Monitor thermistor probe (0.1 mm, o.d.), both nonabsorbing elements, located inside during both microwave and sham exposures. This arrangement enabled stimulation of physiological values of intracellular, venous, and arterial pO2. In addition, since the premixed, refiltered (0.45 nm) O2/N2 gas was gently bubbled at 0.09 LPM, the cell suspension was continuously mixed. This procedure provided an effective means to eliminate thermal gradients during microwave exposures which in the past have led to effects erroneously attributed to non-thermal microwave interactions.

During exposures, the Teflon sample cell (FIG. 7A) is jacketed with a moving wall of dielectric fluid (6 liter/min), to thermostat to maintain the sample at an equilibrium exposure temperature (±0.01° C., Thermometrics, Edison, N.J.), thermostat measure inflow and outflow temperatures of the circulating dielectric fluid, and was used to continuously monitor the temperature differential between inflow and outflow thermistors. Sample temperature was correlated to this differential by comparing the latter to direct VITEK probe measurements.

The A919a thermistors from Thermometrics, Inc. as well as the VITEK probe were each calibrated against an NBS-traceable S-10 temperature standard (±0.0015° C. accuracy, Thermometrics).

The specific absorption rate (SAR) for microwave exposures of cell suspensions was determined from direct temperature measurements on nonthermostated samples. The equation used to compute the SAR is (1):

$$SAR(mW/g) = \frac{T \times C_p}{1.16} \quad (1)$$

where T is the temperature change in ° C. per hour, and $C_p$ is the specific heat of the absorbing sample. A value of 0.83 kcal/° C. kg for $C_p$ is assumed for the liposome-target cell suspension. Values of SAR obtained in this way were used to determine an equivalent internal electric field intensity present in the absorbing sample, which was distinct from the electric field incident on the sample, by using the relationship shown (2):

$$E_{in}(v/m) = \left[ \frac{2p}{\sigma} SAR \right]^{\frac{1}{2}} \quad (2)$$

For suspensions, a value of 1000 kg/m³ was used for p, and a value of 2.0 mho/m at 2450 MHz was used for σ.

Sham exposures (without electromagnetic field irradiation) were conducted with liposome-cell suspensions placed in tubes positioned in a circulating waterbath which was maintained at an equivalent exposure temperature to within ±0.05° C.

EXAMPLE 2

General Procedures for Microwave and Sham Exposures In Vivo

Animals used in these studies were adult rats. Each animal received a subcutaneous liposome(s) depot and were subsequently treated with microwave fields between 26–2650 MHz using a commercially available contact applicator which was obtained from ELMED Corporation, Addison, Ill. (Model 3013). Such applicators are used widely in rehabilitation medicine clinics for hyperthermia treatments, and in cancer clinics to provide heat for the treatment of cancer tumors. This device is depicted in FIGS. 7, 7A. Thus, a particular output setting on the microwave generator would be associated with a particular SAR for the exposure, and this is the standard unit of calibration for microwave exposures. In general, SARs about 100 mW/gm are considered thermogenic and cause tissue heating that cannot be compensated by normal thermoregulatory mechanisms. The exposures performed here were conducted at nonthermogenic SAR of 0.1–6.0 mW/gm. SAR was determined by the measurement technique applicable to Equation 1.

Although this invention has been described with reference to particular embodiments, it will be understood that this invention involving phase and nonphase transition liposomes to deliver drugs or chemical agents upon application of electromagnetic radiation is capable of encompassing all other embodiments falling within the spirit and scope of the appended claims.

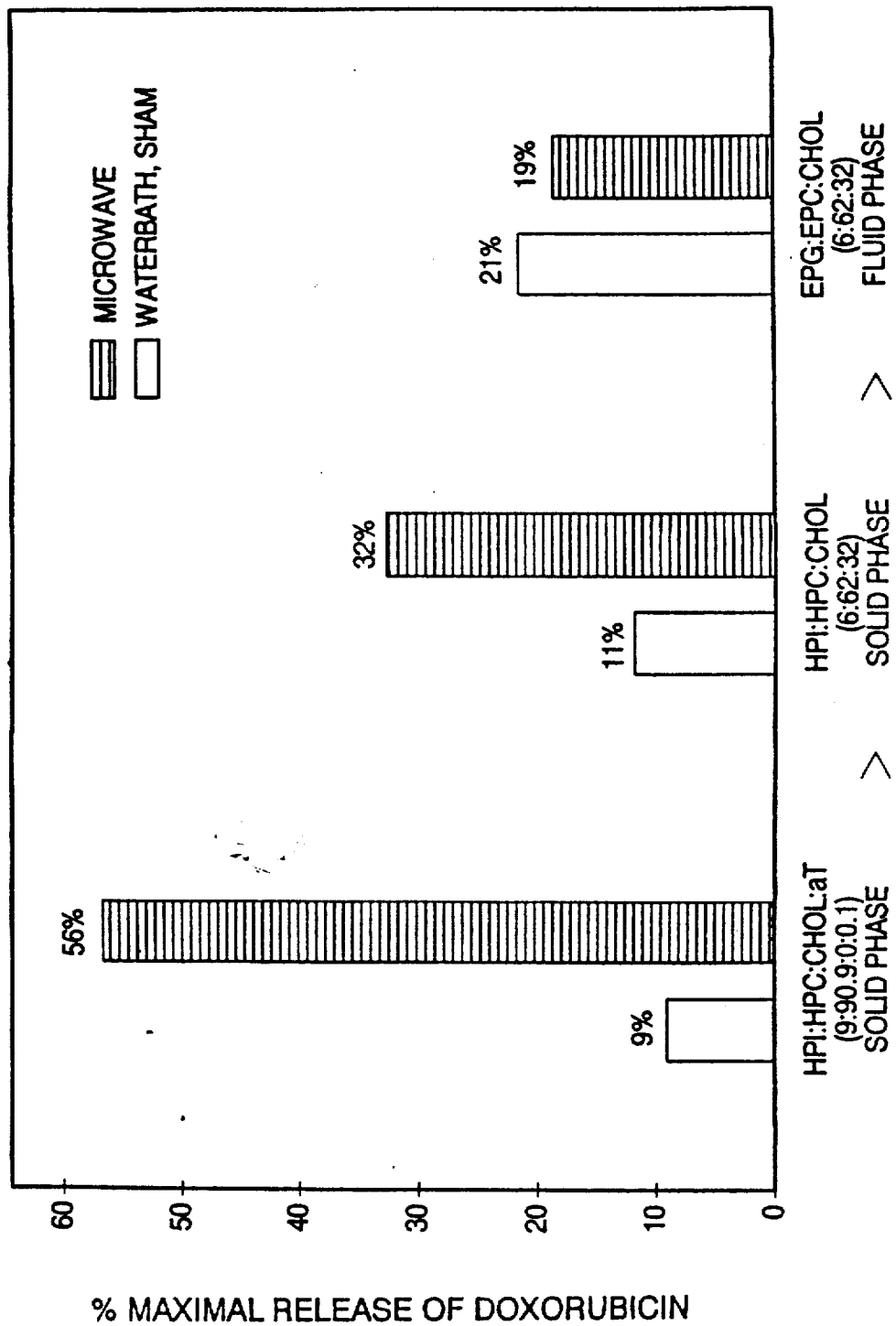

I claim:

1. A method of delivering a drug to a preselected target body site of a patient at a temperature within a specific temperature range between about 10° C. and 65° C. comprising the steps of:
   (a) administering the drug to the target body site said drug being within a liposome composition, the liposome composition having drug release characteristics that are essentially temperature insensitive within the specific temperature range and not having a phase transition temperature within the specific temperature range at which the liposome composition spontaneously releases drug and
   (b) subjecting the preselected target body site and liposome composition thereupon to a nonionizing electromagnetic field to release drug from the liposome composition at a temperature within the specific temperature range.

2. The method of claim 1 wherein the administering of the liposome composition to the target body site is accomplished by administering the composition into the patient's blood stream and allowing it to circulate to the target body site.

3. The method of claim 2 wherein the liposome composition additionally comprises an immunoactive or specific group which is capable of preferentially binding the liposome to the target body site.

4. The method of claim 3 wherein the target body site is a target cell and the immunoactive or specific group preferentially binds the liposome to the target cell so that when the drug is released, it is preferentially released into the target cell.

5. The method of claim 1 wherein the administering of the liposome composition to the target body site is accomplished by localizing a depot of the liposome composition at the target body site.

6. The method of claim 1 wherein the liposome composition is substantially devoid of free drug.

7. The method of claim 1 wherein said nonionizing field is a microwave or RF field having a frequency in the range of from about 26 MHz to about 2450 MHz.

8. The method of claim 1 wherein said nonionizing field is a static magnetic field of from about 0.01 to about 7.5 Tesla.

9. The method of claim 1 wherein step (b) is repeated.

10. The method of claim 1 wherein said liposome composition comprises at least one perturbing agent and at least one lipid component.

11. The method of claim 10 wherein at least one perturbing agent is selected from the group consisting of cholesterol, lecithin, mixtures of phosphatidylglycerol and phosphatidylcholine each having fatty acids of different chain length, proteins and mixtures thereof.

12. The method of claim 11 wherein the lipid is selected from the group consisting of dimyristoylphosphatidylcholine, dimyristoylphosphatidylglycerol, dipalmitoylphosphatidylchloine, dipalmitoylphosphatidylglycerol, egg phosphatidylcholine, hydrogenated phosphatidylinositol, hydrogenated phosphatidylcholine, phosphatidylcholine, phosphatidylglycerol, phosphatidylinositol and mixtures thereof.

13. The method of claim 12 wherein the at least one perturbing agent comprises cholesterol.

14. The method of claim 11 wherein the at least one perturbing agent comprises cholesterol and wherein the mole ratio of cholesterol to lipid is between about 32:68 and 10:90.

15. The method of claim 11 wherein the perturbing agent is selected from the group consisting of proteins having a molecular weight of between about 1,000 and 10,000,000 daltons.

16. The method of claim 15 wherein the protein is an antibody.

17. The method of claim 15 wherein the perturbing agent is an antibody which is derivatized to a hydrophobic moiety which is within the lipid bilayer.

18. The method of claim 10 wherein the mole ratio of perturbing agent to lipid is between about 32:68 and 90:10.

19. The method of claim 18 wherein the mole ratio is between about 45:55 to 55:45.

20. The method of claim 10 wherein the said liposome composition comprises cholesterol as perturbing agent, and a mixture of 4 parts by weight of 1,2-dipalmitoylphosphatidyl choline and one part by weight 1,2-dipalmitoylphosphatidyl glycerol as the lipid wherein the mole ratio of the perturbing agent to lipid is between about 32:68 and 20:80.

21. The method of claim 10 wherein the perturbing agent is selected from the group consisting of egg-phosphatidylcholine and phosphatidylglycerol.

22. The method of claim 1 wherein step (b) is carried out with the liposome composition in contact with oxygen.

23. The method of claim 1 wherein step (b) is carried out with the liposome composition in contact with added injected blood, serum, plasma, interstitional fluid, synovial fluid, cerebrospinal fluid or components thereof.

24. The method of claim 1 wherein in step (a) the liposome composition comprises at least one biologically active perturbing agent on the surface of the liposome.

25. The method of claim 1 wherein the body site is a cell.

* * * * *

UNITED STATES PATENT AND TRADEMARK OFFICE
CERTIFICATE OF CORRECTION

PATENT NO. : 5,190,761
DATED : March 2, 1993
INVENTOR(S) : Liburdy

It is certified that error appears in the above-indentified patent and that said Letters Patent is hereby corrected as shown below:

In the drawings, sheets 11, 13, 16, 25, and 29, should be deleted to be replaced with the corrected Figs. 11,13,16,25,29, as shown on the attached pages.

Signed and Sealed this

Twenty-eighth Day of December, 1993

Attest:

BRUCE LEHMAN

Attesting Officer

Commissioner of Patents and Trademarks